United States Patent
Tamada et al.

(10) Patent No.: US 12,129,291 B2
(45) Date of Patent: *Oct. 29, 2024

(54) ANTI-GPC3 ANTIBODY

(71) Applicants: Yamaguchi University, Yamaguchi (JP); National Cancer Center, Tokyo (JP); Noile-Immune Biotech, Inc., Tokyo (JP)

(72) Inventors: Koji Tamada, Yamaguchi (JP); Yukimi Sakoda, Yamaguchi (JP); Tetsuya Nakatsura, Chiba (JP); Keigo Saito, Chiba (JP)

(73) Assignees: Yamaguchi University, Yamaguchi (JP); National Cancer Center, Tokyo (JP); Noile-Immune Biotech, Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/335,477

(22) Filed: Jun. 15, 2023

(65) Prior Publication Data

US 2024/0018224 A1    Jan. 18, 2024

Related U.S. Application Data

(63) Continuation of application No. 16/472,356, filed as application No. PCT/JP2018/000257 on Jan. 10, 2018, now Pat. No. 11,718,663.

(30) Foreign Application Priority Data

Jan. 10, 2017  (JP) ................. 2017-001732

(51) Int. Cl.
  C07K 16/18    (2006.01)
  C07K 14/54    (2006.01)
  C07K 14/725   (2006.01)
  C07K 16/30    (2006.01)
  C12N 5/078    (2010.01)
  C12N 5/0783   (2010.01)
  G01N 33/68    (2006.01)

(52) U.S. Cl.
  CPC .......... C07K 16/18 (2013.01); C07K 14/5418 (2013.01); C07K 14/7051 (2013.01); C07K 16/303 (2013.01); C12N 5/0634 (2013.01); C12N 5/0636 (2013.01); G01N 33/68 (2013.01); C07K 2317/24 (2013.01); C07K 2317/565 (2013.01); C07K 2317/622 (2013.01); C07K 2319/02 (2013.01); C07K 2319/03 (2013.01)

(58) Field of Classification Search
CPC . C07K 16/18; C07K 2317/565; G01N 33/574
See application file for complete search history.

(56) References Cited

U.S. PATENT DOCUMENTS

| | | | |
|---|---|---|---|
| 10,781,249 B2* | 9/2020 | Tamada | C07K 16/18 |
| 2006/0014223 A1 | 1/2006 | Aburatani et al. | |
| 2006/0167232 A1 | 7/2006 | Aburatani et al. | |
| 2007/0190599 A1 | 8/2007 | Nakano et al. | |
| 2016/0215261 A1 | 7/2016 | Li et al. | |
| 2017/0010270 A1 | 1/2017 | Ohtomo et al. | |
| 2017/0291953 A1 | 10/2017 | Tamada et al. | |

FOREIGN PATENT DOCUMENTS

| | | |
|---|---|---|
| JP | 4011100 B2 | 9/2007 |
| JP | 2015-526387 A | 9/2015 |
| JP | 2016-523518 A | 8/2016 |
| WO | WO-2004/022739 A1 | 3/2004 |
| WO | WO-2012/145469 A1 | 10/2012 |
| WO | WO-2013/070468 A1 | 5/2013 |
| WO | WO-2013/181543 A1 | 12/2013 |
| WO | WO-2015/097928 A1 | 7/2015 |
| WO | WO-2015/179658 A2 | 11/2015 |
| WO | WO-2016/036973 A1 | 3/2016 |
| WO | WO-2016/049459 A1 | 3/2016 |
| WO | WO-2016/056228 A1 | 4/2016 |

OTHER PUBLICATIONS

Zheng et al (Novel and Promising Target for the Treatment of Hepatocellular Carcinoma. Front Oncol. Feb. 16, 2022;12:824208) (Year: 2022).*
Gao et al (Development of T cells redirected to glypican-3 for the treatment of hepatocellular carcinoma. Clin Cancer Res. Dec. 15, 2014;20(24):6418-28) (Year: 2014).*
Allison et al., Heterogeneity and Cancer, retrieved from: https://www.cancernetwork.com/view/heterogeneity-and-cancer (2014) (Year: 2014).*
American Cancer Society (Can Cancer be Cured?, American Cancer Society, retrieved from: https://www.cancer.org/cancer/understanding-cancer/can-cancer-be-cured.html)(2021) (Year: 2021).*

(Continued)

*Primary Examiner* — Elizabeth C. Kemmerer
*Assistant Examiner* — Ashley H. Gao
(74) *Attorney, Agent, or Firm* — Foley & Lardner LLP

(57) ABSTRACT

An object of the present invention is to provide: an anti-GPC3 antibody that recognizes an epitope different from that for existing antibodies (e.g., GC33 and GC199) and can specifically bind, even in the form of single chain antibody, to GPC3 localized on a cell membrane; CAR comprising the anti-GPC3 single chain antibody; an immunocompetent cell expressing the CAR; a gene of the anti-GPC3 antibody or a gene of the CAR; a vector comprising the anti-GPC3 antibody gene or the CAR gene; a host cell in which the vector has been introduced; a method for specifically detecting GPC3; and a kit for specifically detecting GPC3. An antibody comprising particular heavy chain CDR1 to CDR3 and particular light chain CDR1 to CDR3 defined in claim 1, and specifically binding to a human-derived GPC3 polypeptide specifically binds to GPC3 localized on a cell membrane. CAR-immunocompetent cells prepared on the basis of CAR comprising such single chain antibody are useful for cancer immunotherapy.

15 Claims, 7 Drawing Sheets

Specification includes a Sequence Listing.

(56) References Cited

OTHER PUBLICATIONS

Baumhoer et al (Glypican 3 expression in human nonneoplastic, preneoplastic, and neoplastic tissues: a tissue microarray analysis of 4,387 tissue samples. Am J Clin Pathol. Jun. 2008;129(6): 899-906) (Year: 2008).*
Abascal et al (TranslatorX: multiple alignment of nucleotide sequences guided by amino acids translations, Nucleic Acids Research, vol. 38, Issue suppl_2, Jul. 1, 2010, pp. W7-W13, https://doi.org/10.1093/nar/gkq291) (Year: 2010).*
Deal et al (Vectored antibody gene delivery for the prevention or treatment of HIV infection. Curr Opin HIV AIDS. May 2015;10(3):190-7) (Year: 2015).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Hippo et al., "Identification of Soluble NH2-Terminal Fragment of Glypican-3 as a Serological Marker for Early-Stage Hepatocellular Carcinoma," Cancer Research, Apr. 1, 2004, 64:2418-2423.
Li et al., "Redirecting T Cells to Glypican-3 with 4-1BB Zeta Chimeric Antigen Receptors Results in Th1 Polarization and Potent Antitumor Activity," Human Gene Therapy, Aug. 16, 2016, 28(5):437-448.
Lin et al., "Improved affinity of a chicken single-chain antibody to avian infectious bronchitis virus by site-directed mutagenesis of complementarily-determining region H3", African Journal of Biotechnology, Dec. 12, 2011, 10(79):18294-18302.
Mariuzza, R.A., "The Structural Basis of Antigen-Antibody Recognition," Ann. Rev. Biophys. Biophys. Chem., 1987, 16:139-159.
McCarthy et al., "Altering the fine specificity of an anti-Legionella single chain antibody by a single amino acid insertion," Journal of Immunological Methods, 2001, 251:137-149.
Nakano et al., "Anti-glypican 3 antibodies cause ADCC against human hepatocellular carcinoma cells," Biochemical and Biophysical Research Communications, 2009, 378:279-284.
Nakatsura, Tetsuya, "Era of cancer immunotherapy has come," Jpn. J. Clin. Immunol., 2016, 39(3):164- 171.
Phung et al., "High-affinity monoclonal antibodies to cell surface tumor antigen glypican-3 generated through a combination of peptide immunization and flow cytometry screening," MABS, Sep. 1, 2012, 4(5):592-599.
Li et al., "Abstract 2549: Development of CAR T-cell therapy targeting glypican-3 in liver cancer," Cancer Research, Aug. 1, 2018, 78(13_Supplement): 2549, 2 pages.
Li et al., "Persistent Polyfunctional Chimeric Antigen Receptor T Cells That Target Glypican 3 Eliminate Orthotopic Hepatocellular Carcinomas in Mice," Gastroenterology, Feb. 12, 2020, 158(8):2250-2285.

* cited by examiner

```
                              SEQUENCE LISTING

Sequence total quantity: 191
SEQ ID NO: 1            moltype = AA  length = 5
FEATURE                 Location/Qualifiers
REGION                  1..5
                        note = TF1413-02d028 H Chain CDR 1
REGION                  1..5
                        note = MISC_FEATURE - Inventor: TAMADA, Koji; SAKODA,
                         Yukimi; NAKATSURA, Tetsuya; SAITO , Keigo
source                  1..5
                        mol_type = protein
                        organism = synthetic construct
SEQUENCE: 1
GYNMN                                                                        5

SEQ ID NO: 2            moltype = AA  length = 17
FEATURE                 Location/Qualifiers
REGION                  1..17
                        note = TF1413-02d028 H Chain CDR 2
source                  1..17
                        mol_type = protein
                        organism = synthetic construct
SEQUENCE: 2
NIDPYYGGTS YNQKFKG                                                          17

SEQ ID NO: 3            moltype = AA  length = 10
FEATURE                 Location/Qualifiers
REGION                  1..10
                        note = TF1413-02d028 H Chain CDR 3
source                  1..10
                        mol_type = protein
                        organism = synthetic construct
SEQUENCE: 3
GDYRAYYFDY                                                                  10

SEQ ID NO: 4            moltype = AA  length = 11
FEATURE                 Location/Qualifiers
REGION                  1..11
                        note = TF1413-02d028 L Chain CDR 1
source                  1..11
                        mol_type = protein
                        organism = synthetic construct
SEQUENCE: 4
KASQNVRTAV A                                                                11

SEQ ID NO: 5            moltype = AA  length = 7
FEATURE                 Location/Qualifiers
REGION                  1..7
                        note = TF1413-02d028 L Chain CDR 2
source                  1..7
                        mol_type = protein
                        organism = synthetic construct
SEQUENCE: 5
LASNRHT                                                                      7

SEQ ID NO: 6            moltype = AA  length = 9
FEATURE                 Location/Qualifiers
REGION                  1..9
                        note = TF1413-02d028 L Chain CDR 3
source                  1..9
                        mol_type = protein
                        organism = synthetic construct
SEQUENCE: 6
LQHWNYPLT                                                                    9

SEQ ID NO: 7            moltype = AA  length = 118
FEATURE                 Location/Qualifiers
REGION                  1..118
```

-continued

```
                        note = TF1413-02d028 H Chain V Region
source                  1..118
                        mol_type = protein
                        organism = synthetic construct
SEQUENCE: 7
QVQLKESGPE LEKPGASVKI SCKASGYSFT GYNMNWVKQS NGKSLEWIGN IDPYYGGTSY    60
NQKFKGKATL TVDKSSSTAY MQLKSLTSED SAVYYCARGD YRAYYFDYWG QGTTLTVS     118

SEQ ID NO: 8            moltype = AA  length = 108
FEATURE                 Location/Qualifiers
REGION                  1..108
                        note = TF1413-02d028 L Chain V Region
source                  1..108
                        mol_type = protein
                        organism = synthetic construct
SEQUENCE: 8
DIQMTQSPKF MSTSVGDRVS ITCKASQNVR TAVAWYQQKP GQSPKALIYL ASNRHTGVPD    60
RFTGSGSGTD FTLTISNVQS EDLADYFCLQ HWNYPLTFGA GTKLELKR               108

SEQ ID NO: 9            moltype = AA  length = 449
FEATURE                 Location/Qualifiers
REGION                  1..449
                        note = TF1413-02d028 H Chain
source                  1..449
                        mol_type = protein
                        organism = synthetic construct
SEQUENCE: 9
QVQLKESGPE LEKPGASVKI SCKASGYSFT GYNMNWVKQS NGKSLEWIGN IDPYYGGTSY    60
NQKFKGKATL TVDKSSSTAY MQLKSLTSED SAVYYCARGD YRAYYFDYWG QGTTLTVSSA   120
KTTAPSVYPL APVCGDTTGS SVTLGCLVKG YFPEPVTLTW NSGSLSSGVH TFPAVLQSDL   180
YTLSSSVTVT SSTWPSQSIT CNVAHPASST KVDKKIEPRG PTIKPCPPCK CPAPNLLGGP   240
SVFIFPPKIK DVLMISLSPI VTCVVVDVSE DDPDVQISWF VNNVEVHTAQ TQTHREDYNS   300
TLRVVSALPI QHQDWMSGKE FKCKVNNKDL PAPIERTISK PKGSVRAPQV YVLPPPEEEM   360
TKKQVTLTCM VTDFMPEDIY VEWTNNGKTE LNYKNTEPVL DSDGSYFMYS KLRVEKKNWV   420
ERNSYSCSVV HEGLHNHHTT KSFSRTPGK                                    449

SEQ ID NO: 10           moltype = AA  length = 214
FEATURE                 Location/Qualifiers
REGION                  1..214
                        note = TF1413-02d028 L Chain
source                  1..214
                        mol_type = protein
                        organism = synthetic construct
SEQUENCE: 10
DIQMTQSPKF MSTSVGDRVS ITCKASQNVR TAVAWYQQKP GQSPKALIYL ASNRHTGVPD    60
RFTGSGSGTD FTLTISNVQS EDLADYFCLQ HWNYPLTFGA GTKLELKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                              214

SEQ ID NO: 11           moltype = AA  length = 5
FEATURE                 Location/Qualifiers
REGION                  1..5
                        note = TF1413-02d039 H Chain CDR 1
source                  1..5
                        mol_type = protein
                        organism = synthetic construct
SEQUENCE: 11
SYDMS                                                                5

SEQ ID NO: 12           moltype = AA  length = 17
FEATURE                 Location/Qualifiers
REGION                  1..17
                        note = TF1413-02d039 H Chain CDR 2
source                  1..17
                        mol_type = protein
                        organism = synthetic construct
SEQUENCE: 12
YISSGGGSTY YPDTVKG                                                  17

SEQ ID NO: 13           moltype = AA  length = 9
FEATURE                 Location/Qualifiers
REGION                  1..9
                        note = TF1413-02d039 H Chain CDR 3
source                  1..9
                        mol_type = protein
                        organism = synthetic construct
SEQUENCE: 13
RGLRRAMDY                                                            9
```

```
SEQ ID NO: 14             moltype = AA   length = 16
FEATURE                   Location/Qualifiers
REGION                    1..16
                          note = TF1413-02d039 L Chain CDR 1
source                    1..16
                          mol_type = protein
                          organism = synthetic construct
SEQUENCE: 14
RSSQSLVHSN GNTYLH                                                      16

SEQ ID NO: 15             moltype = AA   length = 7
FEATURE                   Location/Qualifiers
REGION                    1..7
                          note = TF1413-02d039 L Chain CDR 2
source                    1..7
                          mol_type = protein
                          organism = synthetic construct
SEQUENCE: 15
KVSNRFS                                                                7

SEQ ID NO: 16             moltype = AA   length = 9
FEATURE                   Location/Qualifiers
REGION                    1..9
                          note = TF1413-02d039 L Chain CDR 3
source                    1..9
                          mol_type = protein
                          organism = synthetic construct
SEQUENCE: 16
SQSTHVPLT                                                              9

SEQ ID NO: 17             moltype = AA   length = 117
FEATURE                   Location/Qualifiers
REGION                    1..117
                          note = TF1413-02d039 H Chain V Region
source                    1..117
                          mol_type = protein
                          organism = synthetic construct
SEQUENCE: 17
EVKLVESGGG LVKPGGSLKL SCAASGFAFS SYDMSWVRQT PEKRLEWVAY ISSGGGSTYY       60
PDTVKGRFTI SRDNAKNTLY LQMSSLKSED TAMYYCARRG LRRAMDYWGQ GTSVTVS         117

SEQ ID NO: 18             moltype = AA   length = 113
FEATURE                   Location/Qualifiers
REGION                    1..113
                          note = TF1413-02d039 L Chain V Region
source                    1..113
                          mol_type = protein
                          organism = synthetic construct
SEQUENCE: 18
DVVMTQTPLS LPVSLGDQAS ISCRSSQSLV HSNGNTYLHW YLQKPGQSPK LLIYKVSNRF       60
SGVPDRFSGS GSGTDFTLKI SRVEAEDLGV YFCSQSTHVP LTFGAGTKLE LKR             113

SEQ ID NO: 19             moltype = AA   length = 448
FEATURE                   Location/Qualifiers
REGION                    1..448
                          note = TF1413-02d039 H Chain
source                    1..448
                          mol_type = protein
                          organism = synthetic construct
SEQUENCE: 19
EVKLVESGGG LVKPGGSLKL SCAASGFAFS SYDMSWVRQT PEKRLEWVAY ISSGGGSTYY       60
PDTVKGRFTI SRDNAKNTLY LQMSSLKSED TAMYYCARRG LRRAMDYWGQ GTSVTVSSAK      120
TTAPSVYPLA PVCGDTTGSS VTLGCLVKGY FPEPVTLTWN SGSLSSGVHT FPAVLQSDLY      180
TLSSSVTVTS STWPSQSITC NVAHPASSTK VDKKIEPRGP TIKPCPPCKC PAPNLLGGPS      240
VFIFPPKIKD VLMISLSPIV TCVVVDVSED DPDVQISWFV NNVEVHTAQT QTHREDYNST      300
LRVVSALPIQ HQDWMSGKEF KCKVNNKDLP APIERTISKP KGSVRAPQVY VLPPPEEEMT      360
KKQVTLTCMV TDFMPEDIYV EWTNNGKTEL NYKNTEPVLD SDGSYFMYSK LRVEKKNWVE      420
RNSYSCSVVH EGLHNHHTTK SFSRTPGK                                        448

SEQ ID NO: 20             moltype = AA   length = 219
FEATURE                   Location/Qualifiers
REGION                    1..219
                          note = TF1413-02d039 L Chain
source                    1..219
                          mol_type = protein
                          organism = synthetic construct
SEQUENCE: 20
DVVMTQTPLS LPVSLGDQAS ISCRSSQSLV HSNGNTYLHW YLQKPGQSPK LLIYKVSNRF       60
SGVPDRFSGS GSGTDFTLKI SRVEAEDLGV YFCSQSTHVP LTFGAGTKLE LKRADAAPTV      120
```

```
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                        219

SEQ ID NO: 21              moltype = AA   length = 5
FEATURE                    Location/Qualifiers
REGION                     1..5
                           note = TF1413-02e004 H Chain CDR 1
source                     1..5
                           mol_type = protein
                           organism = synthetic construct
SEQUENCE: 21
SYWMN                                                              5

SEQ ID NO: 22              moltype = AA   length = 17
FEATURE                    Location/Qualifiers
REGION                     1..17
                           note = TF1413-02e004 H Chain CDR 2
source                     1..17
                           mol_type = protein
                           organism = synthetic construct
SEQUENCE: 22
RIDPSDSETH YNQKFKD                                                17

SEQ ID NO: 23              moltype = AA   length = 7
FEATURE                    Location/Qualifiers
REGION                     1..7
                           note = TF1413-02e004 H Chain CDR 3
source                     1..7
                           mol_type = protein
                           organism = synthetic construct
SEQUENCE: 23
GYYAMDY                                                            7

SEQ ID NO: 24              moltype = AA   length = 11
FEATURE                    Location/Qualifiers
REGION                     1..11
                           note = TF1413-02e004 L Chain CDR 1
source                     1..11
                           mol_type = protein
                           organism = synthetic construct
SEQUENCE: 24
KASQDVSTAV A                                                      11

SEQ ID NO: 25              moltype = AA   length = 7
FEATURE                    Location/Qualifiers
REGION                     1..7
                           note = TF1413-02e004 L Chain CDR 2
source                     1..7
                           mol_type = protein
                           organism = synthetic construct
SEQUENCE: 25
SASYRYT                                                            7

SEQ ID NO: 26              moltype = AA   length = 8
FEATURE                    Location/Qualifiers
REGION                     1..8
                           note = TF1413-02e004 L Chain CDR 3
source                     1..8
                           mol_type = protein
                           organism = synthetic construct
SEQUENCE: 26
QQHYSTPT                                                           8

SEQ ID NO: 27              moltype = AA   length = 115
FEATURE                    Location/Qualifiers
REGION                     1..115
                           note = TF1413-02e004 H Chain V Region
source                     1..115
                           mol_type = protein
                           organism = synthetic construct
SEQUENCE: 27
QVQLQQSGAE LVKPGAPVKL SCKASGYTFT SYWMNWVKQR PGRGLEWIGR IDPSDSETHY   60
NQKFKDEATL TVDKSSSTAY IQLSSLTSED SAVYYCARGY YAMDYWGQGT SVTVS      115

SEQ ID NO: 28              moltype = AA   length = 107
FEATURE                    Location/Qualifiers
REGION                     1..107
                           note = TF1413-02e004 L Chain V Region
source                     1..107
```

```
                              mol_type = protein
                              organism = synthetic construct
SEQUENCE: 28
DIVLTQSPKF MSTSVGDRVS ITCKASQDVS TAVAWYQQKP GQSPKLLIYS ASYRYTGVPD      60
RFTGSGSGTD FTFTISSVQA EDLAVYYCQQ HYSTPTFGGG TKLEIKR                  107

SEQ ID NO: 29                 moltype = AA   length = 446
FEATURE                       Location/Qualifiers
REGION                        1..446
                              note = TF1413-02e004 H Chain
source                        1..446
                              mol_type = protein
                              organism = synthetic construct
SEQUENCE: 29
QVQLQQSGAE LVKPGAPVKL SCKASGYTFT SYWMNWVKQR PGRGLEWIGR IDPSDSETHY      60
NQKFKDEATL TVDKSSSTAY IQLSSLTSED SAVYYCARGY YAMDYWGQGT SVTVSSAKTT     120
APSVYPLAPV CGDTTGSSVT LGCLVKGYFP EPVTLTWNSG SLSSGVHTFP AVLQSDLYTL     180
SSSVTVTSST WPSQSITCNV AHPASSTKVD KKIEPRGPTI KPCPPCKCPA PNLLGGPSVF     240
IPPPKIKDVL MISLSPIVTC VVVDVSEDDP DVQISWFVNN VEVHTAQTQT HREDYNSTLR     300
VVSALPIQHQ DWMSGKEFKC KVNNKDLPAP IERTISKPKG SVRAPQVYVL PPPEEEMTKK     360
QVTLTCMVTD FMPEDIYVEW TNNGKTELNY KNTEPVLDSD GSYFMYSKLR VEKKNWVERN     420
SYSCSVVHEG LHNHHTTKSF SRTPGK                                         446

SEQ ID NO: 30                 moltype = AA   length = 213
FEATURE                       Location/Qualifiers
REGION                        1..213
                              note = TF1413-02e004 L Chain
source                        1..213
                              mol_type = protein
                              organism = synthetic construct
SEQUENCE: 30
DIVLTQSPKF MSTSVGDRVS ITCKASQDVS TAVAWYQQKP GQSPKLLIYS ASYRYTGVPD      60
RFTGSGSGTD FTFTISSVQA EDLAVYYCQQ HYSTPTFGGG TKLEIKRADA APTVSIFPPS     120
SEQLTSGGAS VVCFLNNFYP KDINVKWKID GSERQNGVLN SWTDQDSKDS TYSMSSTLTL     180
TKDEYERHNS YTCEATHKTS TSPIVKSFNR NEC                                 213

SEQ ID NO: 31                 moltype = AA   length = 5
FEATURE                       Location/Qualifiers
REGION                        1..5
                              note = TF1413-02e014 H Chain CDR 1
source                        1..5
                              mol_type = protein
                              organism = synthetic construct
SEQUENCE: 31
DYYMH                                                                  5

SEQ ID NO: 32                 moltype = AA   length = 17
FEATURE                       Location/Qualifiers
REGION                        1..17
                              note = TF1413-02e014 H Chain CDR 2
source                        1..17
                              mol_type = protein
                              organism = synthetic construct
SEQUENCE: 32
WIDPENGDTE YAPKFQG                                                    17

SEQ ID NO: 33                 moltype = AA   length = 11
FEATURE                       Location/Qualifiers
REGION                        1..11
                              note = TF1413-02e014 H Chain CDR 3
source                        1..11
                              mol_type = protein
                              organism = synthetic construct
SEQUENCE: 33
YYDYDGYAMD Y                                                          11

SEQ ID NO: 34                 moltype = AA   length = 11
FEATURE                       Location/Qualifiers
REGION                        1..11
                              note = TF1413-02e014 L Chain CDR 1
source                        1..11
                              mol_type = protein
                              organism = synthetic construct
SEQUENCE: 34
KASQDVGTAV A                                                          11

SEQ ID NO: 35                 moltype = AA   length = 7
FEATURE                       Location/Qualifiers
REGION                        1..7
```

```
                        note = TF1413-02e014 L Chain CDR 2
source                  1..7
                        mol_type = protein
                        organism = synthetic construct
SEQUENCE: 35
WASTRHT                                                                     7

SEQ ID NO: 36           moltype = AA  length = 9
FEATURE                 Location/Qualifiers
REGION                  1..9
                        note = TF1413-02e014 L Chain CDR 3
source                  1..9
                        mol_type = protein
                        organism = synthetic construct
SEQUENCE: 36
QQYSSYPLT                                                                   9

SEQ ID NO: 37           moltype = AA  length = 120
FEATURE                 Location/Qualifiers
REGION                  1..120
                        note = TF1413-02e014 H Chain V Region
source                  1..120
                        mol_type = protein
                        organism = synthetic construct
SEQUENCE: 37
QVQLKQSGAE LVRSGASVKL SCTASGFNIK DYYMHWVKQR PEQGLEWIGW IDPENGDTEY           60
APKFQGKATM TADTSSNTAY LQLSSLTSED TAVYYCNAGY YDYDGYAMDY WGQGTSVTVS          120

SEQ ID NO: 38           moltype = AA  length = 108
FEATURE                 Location/Qualifiers
REGION                  1..108
                        note = TF1413-02e014 L Chain V Region
source                  1..108
                        mol_type = protein
                        organism = synthetic construct
SEQUENCE: 38
DIVLTQSPKF MSTSVGDRVS ITCKASQDVG TAVAWYQQKP GQSPKLLIYW ASTRHTGVPD           60
RFTGSGSGTD FTLTISNVQS EDLADYFCQQ YSSYPLTFGG GTKLEIKR                       108

SEQ ID NO: 39           moltype = AA  length = 451
FEATURE                 Location/Qualifiers
REGION                  1..451
                        note = TF1413-02e014 H Chain
source                  1..451
                        mol_type = protein
                        organism = synthetic construct
SEQUENCE: 39
QVQLKQSGAE LVRSGASVKL SCTASGFNIK DYYMHWVKQR PEQGLEWIGW IDPENGDTEY           60
APKFQGKATM TADTSSNTAY LQLSSLTSED TAVYYCNAGY YDYDGYAMDY WGQGTSVTVS          120
SAKKTAPSVY PLAPVCGDTT GSSVTLGCLV KGYFPEPVTL TWNSGSLSSG VHTFPAVLQS          180
DLYTLSSSVT VTSSTWPSQS ITCNVAHPAS STKVDKKIEP RGPTIKPCPP CKCPAPNLLG          240
GPSVFIFPPK IKDVLMISLS PIVTCVVVDV SEDDPDVQIS WFVNNVEVHT AQTQTHREDY          300
NSTLRVVSAL PIQHQDWMSG KEFKCKVNNK DLPAPIERTI SKPKGSVRAP QVYVLPPPEE          360
EMTKKQVTLT CMVTDFMPED IYVEWTNNGK TELNYKNTEP VLDSDGSYFM YSKLRVEKKN          420
WVERNSYSCS VVHEGLHNHH TTKSFSRTPG K                                         451

SEQ ID NO: 40           moltype = AA  length = 214
FEATURE                 Location/Qualifiers
REGION                  1..214
                        note = TF1413-02e014 L Chain
source                  1..214
                        mol_type = protein
                        organism = synthetic construct
SEQUENCE: 40
DIVLTQSPKF MSTSVGDRVS ITCKASQDVG TAVAWYQQKP GQSPKLLIYW ASTRHTGVPD           60
RFTGSGSGTD FTLTISNVQS EDLADYFCQQ YSSYPLTFGG GTKLEIKRAD AAPTVSIFPP          120
SSEQLTSGGA SVVCFLNNFY PKDINVKWKI DGSERQNGVL NSWTDQDSKD STYSMSSTLT          180
LTKDEYERHN SYTCEATHKT STSPIVKSFN RNEC                                      214

SEQ ID NO: 41           moltype = AA  length = 5
FEATURE                 Location/Qualifiers
REGION                  1..5
                        note = TF1413-02e030 H Chain CDR 1
source                  1..5
                        mol_type = protein
                        organism = synthetic construct
SEQUENCE: 41
DYYMH                                                                       5
```

```
SEQ ID NO: 42            moltype = AA   length = 17
FEATURE                  Location/Qualifiers
REGION                   1..17
                         note = TF1413-02e030 H Chain CDR 2
source                   1..17
                         mol_type = protein
                         organism = synthetic construct
SEQUENCE: 42
WIDPENGNTI YDPKFQG                                                    17

SEQ ID NO: 43            moltype = AA   length = 8
FEATURE                  Location/Qualifiers
REGION                   1..8
                         note = TF1413-02e030 H Chain CDR 3
source                   1..8
                         mol_type = protein
                         organism = synthetic construct
SEQUENCE: 43
TMITTLDY                                                              8

SEQ ID NO: 44            moltype = AA   length = 17
FEATURE                  Location/Qualifiers
REGION                   1..17
                         note = TF1413-02e030 L Chain CDR 1
source                   1..17
                         mol_type = protein
                         organism = synthetic construct
SEQUENCE: 44
KSSQSLLNSS NQKNYLA                                                    17

SEQ ID NO: 45            moltype = AA   length = 7
FEATURE                  Location/Qualifiers
REGION                   1..7
                         note = TF1413-02e030 L Chain CDR 2
source                   1..7
                         mol_type = protein
                         organism = synthetic construct
SEQUENCE: 45
FASTRES                                                               7

SEQ ID NO: 46            moltype = AA   length = 9
FEATURE                  Location/Qualifiers
REGION                   1..9
                         note = TF1413-02e030 L Chain CDR 3
source                   1..9
                         mol_type = protein
                         organism = synthetic construct
SEQUENCE: 46
QQHYSTPLT                                                             9

SEQ ID NO: 47            moltype = AA   length = 117
FEATURE                  Location/Qualifiers
REGION                   1..117
                         note = TF1413-02e030 H Chain V Region
source                   1..117
                         mol_type = protein
                         organism = synthetic construct
SEQUENCE: 47
EVQLQQSGAE LVRPGALVKL SCKASGFNIK DYYMHWVKQR PEQGLEWIGW IDPENGNTIY      60
DPKFQGKASI TADTSSNTAY LQLSSLTSED TAVYYCAIST MITTLDYWGQ GTTLTVS        117

SEQ ID NO: 48            moltype = AA   length = 114
FEATURE                  Location/Qualifiers
REGION                   1..114
                         note = TF1413-02e030 L Chain V Region
source                   1..114
                         mol_type = protein
                         organism = synthetic construct
SEQUENCE: 48
DIQMTQSPSS LAMSVGQKVT MSCKSSQSLL NSSNQKNYLA WYQQKPGQSP KLLVYFASTR      60
ESGVPDRFIG SGSGTDFTLT ISSVQAEDLA DYFCQQHYST PLTFGAGTKL ELKR           114

SEQ ID NO: 49            moltype = AA   length = 448
FEATURE                  Location/Qualifiers
REGION                   1..448
                         note = TF1413-02e030 H Chain
source                   1..448
                         mol_type = protein
                         organism = synthetic construct
```

```
SEQUENCE: 49
EVQLQQSGAE LVRPGALVKL SCKASGFNIK DYYMHWVKQR PEQGLEWIGW IDPENGNTIY    60
DPKFQGKASI TADTSSNTAY LQLSSLTSED TAVYYCAIST MITTLDYWGQ GTTLTVSSAK   120
TTAPSVYPLA PVCGDTTGSS VTLGCLVKGY FPEPVTLTWN SGSLSSGVHT FPAVLQSDLY   180
TLSSSVTVTS STWPSQSITC NVAHPASSTK VDKKIEPRGP TIKPCPPCKC PAPNLLGGPS   240
VFIFPPKIKD VLMISLSPIV TCVVVDVSED DPDVQISWFV NNVEVHTAQT QTHREDYNST   300
LRVVSALPIQ HQDWMSGKEF KCKVNNKDLP APIERTISKP KGSVRAPQVY VLPPPEEEMT   360
KKQVTLTCMV TDFMPEDIYV EWTNNGKTEL NYKNTEPVLD SDGSYFMYSK LRVEKKNWVE   420
RNSYSCSVVH EGLHNHHTTK SFSRTPGK                                     448

SEQ ID NO: 50            moltype = AA   length = 220
FEATURE                  Location/Qualifiers
REGION                   1..220
                         note = TF1413-02e030 L Chain
source                   1..220
                         mol_type = protein
                         organism = synthetic construct
SEQUENCE: 50
DIQMTQSPSS LAMSVGQKVT MSCKSSQSLL NSSNQKNYLA WYQQKPGQSP KLLVYFASTR    60
ESGVPDRFIG SGSGTDFTLT ISSVQAEDLA DYFCQQHYST PLTFGAGTKL ELKRADAAPT   120
VSIFPPSSEQ LTSGGASVVC FLNNFYPKDI NVKWKIDGSE RQNGVLNSWT DQDSKDSTYS   180
MSSTLTLTKD EYERHNSYTC EATHKTSTSP IVKSFNRNEC                         220

SEQ ID NO: 51            moltype = AA   length = 5
FEATURE                  Location/Qualifiers
REGION                   1..5
                         note = TF1413-02e040 H Chain CDR 1
source                   1..5
                         mol_type = protein
                         organism = synthetic construct
SEQUENCE: 51
GYTMN                                                                5

SEQ ID NO: 52            moltype = AA   length = 17
FEATURE                  Location/Qualifiers
REGION                   1..17
                         note = TF1413-02e040 H Chain CDR 2
source                   1..17
                         mol_type = protein
                         organism = synthetic construct
SEQUENCE: 52
LINPYNGGTS YNQNFKG                                                  17

SEQ ID NO: 53            moltype = AA   length = 8
FEATURE                  Location/Qualifiers
REGION                   1..8
                         note = TF1413-02e040 H Chain CDR 3
source                   1..8
                         mol_type = protein
                         organism = synthetic construct
SEQUENCE: 53
GYYGRFDY                                                             8

SEQ ID NO: 54            moltype = AA   length = 11
FEATURE                  Location/Qualifiers
REGION                   1..11
                         note = TF1413-02e040 L Chain CDR 1
source                   1..11
                         mol_type = protein
                         organism = synthetic construct
SEQUENCE: 54
KASQNVRTAV A                                                        11

SEQ ID NO: 55            moltype = AA   length = 7
FEATURE                  Location/Qualifiers
REGION                   1..7
                         note = TF1413-02e040 L Chain CDR 2
source                   1..7
                         mol_type = protein
                         organism = synthetic construct
SEQUENCE: 55
LASNRHT                                                              7

SEQ ID NO: 56            moltype = AA   length = 9
FEATURE                  Location/Qualifiers
REGION                   1..9
                         note = TF1413-02e040 L Chain CDR 3
source                   1..9
                         mol_type = protein
```

```
                            organism = synthetic construct
SEQUENCE: 56
LQHWNYPLT                                                                        9

SEQ ID NO: 57           moltype = AA   length = 116
FEATURE                 Location/Qualifiers
REGION                  1..116
                        note = TF1413-02e040 H Chain V Region
source                  1..116
                        mol_type = protein
                        organism = synthetic construct
SEQUENCE: 57
EVMLVESGPE LVKPGASMKI SCKASGYSFT GYTMNWVKQS HGKNLEWIGL INPYNGGTSY    60
NQNFKGKATL TVDKSSSTAY MELLSLTSED SAVYYCARGY YGRFDYWGQG TTLTVS        116

SEQ ID NO: 58           moltype = AA   length = 108
FEATURE                 Location/Qualifiers
REGION                  1..108
                        note = TF1413-02e040 L Chain V Region
source                  1..108
                        mol_type = protein
                        organism = synthetic construct
SEQUENCE: 58
DILLTQSPKF MSTSVGDRVS ITCKASQNVR TAVAWYQQKP GQSPKALIYL ASNRHTGVPD    60
RFTGSGSGTD FTLTISNVQS EDLADYFCLQ HWNYPLTFGA GTKLELKR                 108

SEQ ID NO: 59           moltype = AA   length = 447
FEATURE                 Location/Qualifiers
REGION                  1..447
                        note = TF1413-02e040 H Chain
source                  1..447
                        mol_type = protein
                        organism = synthetic construct
SEQUENCE: 59
EVMLVESGPE LVKPGASMKI SCKASGYSFT GYTMNWVKQS HGKNLEWIGL INPYNGGTSY    60
NQNFKGKATL TVDKSSSTAY MELLSLTSED SAVYYCARGY YGRFDYWGQG TTLTVSSAKT    120
TAPSVYPLAP VCGDTTGSSV TLGCLVKGYF PEPVTLTWNS GSLSSGVHTF PAVLQSDLYT    180
LSSSVTVTSS TWPSQSITCN VAHPASSTKV DKKIEPRGPT IKPCPPCKCP APNLLGGPSV    240
FIFPPKIKDV LMISLSPIVT CVVVDVSEDD PDVQISWFVN NVEVHTAQTQ THREDYNSTL    300
RVVSALPIQH QDWMSGKEFK CKVNNKDLPA PIERTISKPK GSVRAPQVYV LPPPEEEMTK    360
KQVTLTCMVT DFMPEDIYVE WTNNGKTELN YKNTEPVLDS DGSYFMYSKL RVEKKNWVER    420
NSYSCSVVHE GLHNHHTTKS FSRTPGK                                       447

SEQ ID NO: 60           moltype = AA   length = 214
FEATURE                 Location/Qualifiers
REGION                  1..214
                        note = TF1413-02e040 L Chain
source                  1..214
                        mol_type = protein
                        organism = synthetic construct
SEQUENCE: 60
DILLTQSPKF MSTSVGDRVS ITCKASQNVR TAVAWYQQKP GQSPKALIYL ASNRHTGVPD    60
RFTGSGSGTD FTLTISNVQS EDLADYFCLQ HWNYPLTFGA GTKLELKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 61           moltype = AA   length = 5
FEATURE                 Location/Qualifiers
REGION                  1..5
                        note = TF1413-03e001 H Chain CDR 1
source                  1..5
                        mol_type = protein
                        organism = synthetic construct
SEQUENCE: 61
GYYMH                                                                5

SEQ ID NO: 62           moltype = AA   length = 17
FEATURE                 Location/Qualifiers
REGION                  1..17
                        note = TF1413-03e001 H Chain CDR 2
source                  1..17
                        mol_type = protein
                        organism = synthetic construct
SEQUENCE: 62
RINPYNGATS YNQNFKD                                                   17

SEQ ID NO: 63           moltype = AA   length = 7
FEATURE                 Location/Qualifiers
REGION                  1..7
```

```
                            note = TF1413-03e001 H Chain CDR 3
source                      1..7
                            mol_type = protein
                            organism = synthetic construct
SEQUENCE: 63
NYGYFDY                                                                      7

SEQ ID NO: 64               moltype = AA  length = 11
FEATURE                     Location/Qualifiers
REGION                      1..11
                            note = TF1413-03e001 L Chain CDR 1
source                      1..11
                            mol_type = protein
                            organism = synthetic construct
SEQUENCE: 64
EASQNVDNNV V                                                                11

SEQ ID NO: 65               moltype = AA  length = 7
FEATURE                     Location/Qualifiers
REGION                      1..7
                            note = TF1413-03e001 L Chain CDR 2
source                      1..7
                            mol_type = protein
                            organism = synthetic construct
SEQUENCE: 65
SASYRYS                                                                      7

SEQ ID NO: 66               moltype = AA  length = 9
FEATURE                     Location/Qualifiers
REGION                      1..9
                            note = TF1413-03e001 L Chain CDR 3
source                      1..9
                            mol_type = protein
                            organism = synthetic construct
SEQUENCE: 66
QQYNSYPLT                                                                    9

SEQ ID NO: 67               moltype = AA  length = 115
FEATURE                     Location/Qualifiers
REGION                      1..115
                            note = TF1413-03e001 H Chain V Region
source                      1..115
                            mol_type = protein
                            organism = synthetic construct
SEQUENCE: 67
QVQLKQSGPE LVKPGASVKI SCKASGYSFT GYYMHWVKQS HVKSLEWIGR INPYNGATSY   60
NQNFKDKASL TVDKSSSTAY MELHSLTSED SAVYYCARNY GYFDYWGQGT TLTVS       115

SEQ ID NO: 68               moltype = AA  length = 108
FEATURE                     Location/Qualifiers
REGION                      1..108
                            note = TF1413-03e001 L Chain V Region
source                      1..108
                            mol_type = protein
                            organism = synthetic construct
SEQUENCE: 68
DIKMTQSPKF MSTSVGDRVS VTCEASQNVD NNVWYQQKP GQSPKALIYS ASYRYSGVPD   60
RFTGSGSGTD FTLTISNVQS EDLAEYFCQQ YNSYPLTFGA GTKLEIKR               108

SEQ ID NO: 69               moltype = AA  length = 446
FEATURE                     Location/Qualifiers
REGION                      1..446
                            note = TF1413-03e001 H Chain
source                      1..446
                            mol_type = protein
                            organism = synthetic construct
SEQUENCE: 69
QVQLKQSGPE LVKPGASVKI SCKASGYSFT GYYMHWVKQS HVKSLEWIGR INPYNGATSY   60
NQNFKDKASL TVDKSSSTAY MELHSLTSED SAVYYCARNY GYFDYWGQGT TLTVSSAKTT  120
APSVYPLAPV CGDTTGSSVT LGCLVKGYFP EPVTLTWNSG SLSSGVHTFP AVLQSDLYTL  180
SSSVTVTSST WPSQSITCNV AHPASSTKVD KKIEPRGPTI KPCPPCKCPA PNLLGGPSVF  240
IFPPKIKDVL MISLSPIVTC VVVDVSEDDP DVQISWFVNN VEVHTAQTQT HREDYNSTLR  300
VVSALPIQHQ DWMSGKEFKC KVNNKDLPAP IERTISKPKG SVRAPQVYVL PPPEEEMTKK  360
QVTLTCMVTD FMPEDIYVEW TNNGKTELNY KNTEPVLDSD GSYFMYSKLR VEKKNWVERN  420
SYSCSVVHEG LHNHHTTKSF SRTPGK                                        446

SEQ ID NO: 70               moltype = AA  length = 214
FEATURE                     Location/Qualifiers
REGION                      1..214
```

```
                        note = TF1413-03e001 L Chain
source                  1..214
                        mol_type = protein
                        organism = synthetic construct
SEQUENCE: 70
DIKMTQSPKF MSTSVGDRVS VTCEASQNVD NNVVWYQQKP GQSPKALIYS ASYRYSGVPD    60
RFTGSGSGTD FTLTISNVQS EDLAEYFCQQ YNSYPLTFGA GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 71           moltype = AA   length = 5
FEATURE                 Location/Qualifiers
REGION                  1..5
                        note = TF1413-03e004 H Chain CDR 1
source                  1..5
                        mol_type = protein
                        organism = synthetic construct
SEQUENCE: 71
SYWMN                                                                 5

SEQ ID NO: 72           moltype = AA   length = 17
FEATURE                 Location/Qualifiers
REGION                  1..17
                        note = TF1413-03e004 H Chain CDR 2
source                  1..17
                        mol_type = protein
                        organism = synthetic construct
SEQUENCE: 72
RIDPSDSETH YNQKFKD                                                   17

SEQ ID NO: 73           moltype = AA   length = 7
FEATURE                 Location/Qualifiers
REGION                  1..7
                        note = TF1413-03e004 H Chain CDR 3
source                  1..7
                        mol_type = protein
                        organism = synthetic construct
SEQUENCE: 73
GYYGSNY                                                               7

SEQ ID NO: 74           moltype = AA   length = 11
FEATURE                 Location/Qualifiers
REGION                  1..11
                        note = TF1413-03e004 L Chain CDR 1
source                  1..11
                        mol_type = protein
                        organism = synthetic construct
SEQUENCE: 74
KASQNVGTNV A                                                         11

SEQ ID NO: 75           moltype = AA   length = 7
FEATURE                 Location/Qualifiers
REGION                  1..7
                        note = TF1413-03e004 L Chain CDR 2
source                  1..7
                        mol_type = protein
                        organism = synthetic construct
SEQUENCE: 75
SASYRYS                                                               7

SEQ ID NO: 76           moltype = AA   length = 9
FEATURE                 Location/Qualifiers
REGION                  1..9
                        note = TF1413-03e004 L Chain CDR 3
source                  1..9
                        mol_type = protein
                        organism = synthetic construct
SEQUENCE: 76
QQYNSYPLT                                                             9

SEQ ID NO: 77           moltype = AA   length = 115
FEATURE                 Location/Qualifiers
REGION                  1..115
                        note = TF1413-03e004 H Chain V Region
source                  1..115
                        mol_type = protein
                        organism = synthetic construct
SEQUENCE: 77
QVQLKQSGAE LVKPGAPVKL SCKASGYTFT SYWMNWVKQR PGRGLEWIGR IDPSDSETHY    60
```

```
NQKFKDKATL TVDKSSSTAY IQLSSLTSED SAVYYCARGY YGSNYWGQGT TLTVS         115

SEQ ID NO: 78           moltype = AA   length = 108
FEATURE                 Location/Qualifiers
REGION                  1..108
                        note = TF1413-03e004 L Chain V Region
source                  1..108
                        mol_type = protein
                        organism = synthetic construct
SEQUENCE: 78
DIKMTQSPKF MSTSVGDRVS VTCKASQNVG TNVAWYQQKP GQSPKALIYS ASYRYSGVPD    60
RFTGSGSGTD FTLTISNVQS EDLAEYFCQQ YNSYPLTFGA GTKLELKR                 108

SEQ ID NO: 79           moltype = AA   length = 403
FEATURE                 Location/Qualifiers
REGION                  1..403
                        note = TF1413-03e004 H Chain
source                  1..403
                        mol_type = protein
                        organism = synthetic construct
SEQUENCE: 79
QVQLKQSGAE LVKPGAPVKL SCKASGYTFT SYWMNWVKQR PGRGLEWIGR IDPSDSETHY    60
NQKFKDKATL TVDKSSSTAY IQLSSLTSED SAVYYCARGY YGSNYWGQGT TLTVSSAKTT    120
APSVYPLAPV CGDTTGSSVT LGCLVKGYFP EPVTLTWNSG SLSSGVHTFP AVLQSDLYTL    180
SSSVTVTSST WPSQSITCNV AHPASSTKVD KKIEPRGPTI KPCPPCKCPA PNLLGGPSVF    240
IFPPKIKDVL MISLSPIVTC VVVDVSEDDP DVQISWFVNN VEVHTAQTQT HREDYNSTLR    300
VVSALPIQHQ DWMSGKEFKC KVNNKDLPAP IERTISKPKG SVRAPQVYVL PPPEEEMTKK    360
QVTLTCMVTD FMPEDIYVEW TNNGKTELNY KNTEPVLDSD GSY                     403

SEQ ID NO: 80           moltype = AA   length = 214
FEATURE                 Location/Qualifiers
REGION                  1..214
                        note = TF1413-03e004 L Chain
source                  1..214
                        mol_type = protein
                        organism = synthetic construct
SEQUENCE: 80
DIKMTQSPKF MSTSVGDRVS VTCKASQNVG TNVAWYQQKP GQSPKALIYS ASYRYSGVPD    60
RFTGSGSGTD FTLTISNVQS EDLAEYFCQQ YNSYPLTFGA GTKLELKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 81           moltype = AA   length = 5
FEATURE                 Location/Qualifiers
REGION                  1..5
                        note = TF1413-03e005 H Chain CDR 1
source                  1..5
                        mol_type = protein
                        organism = synthetic construct
SEQUENCE: 81
DYYMH                                                                5

SEQ ID NO: 82           moltype = AA   length = 17
FEATURE                 Location/Qualifiers
REGION                  1..17
                        note = TF1413-03e005 H Chain CDR 2
source                  1..17
                        mol_type = protein
                        organism = synthetic construct
SEQUENCE: 82
WIDPENGDTE YAPKFQG                                                   17

SEQ ID NO: 83           moltype = AA   length = 11
FEATURE                 Location/Qualifiers
REGION                  1..11
                        note = TF1413-03e005 H Chain CDR 3
source                  1..11
                        mol_type = protein
                        organism = synthetic construct
SEQUENCE: 83
YYDYDGYAMD Y                                                         11

SEQ ID NO: 84           moltype = AA   length = 11
FEATURE                 Location/Qualifiers
REGION                  1..11
                        note = TF1413-03e005 L Chain CDR 1
source                  1..11
                        mol_type = protein
                        organism = synthetic construct
```

-continued

```
SEQUENCE: 84
RASQEISGYL S                                                        11

SEQ ID NO: 85           moltype = AA  length = 7
FEATURE                 Location/Qualifiers
REGION                  1..7
                        note = TF1413-03e005 L Chain CDR 2
source                  1..7
                        mol_type = protein
                        organism = synthetic construct
SEQUENCE: 85
AASTLDS                                                             7

SEQ ID NO: 86           moltype = AA  length = 9
FEATURE                 Location/Qualifiers
REGION                  1..9
                        note = TF1413-03e005 L Chain CDR 3
source                  1..9
                        mol_type = protein
                        organism = synthetic construct
SEQUENCE: 86
LQYASYPLT                                                           9

SEQ ID NO: 87           moltype = AA  length = 120
FEATURE                 Location/Qualifiers
REGION                  1..120
                        note = TF1413-03e005 H Chain V Region
source                  1..120
                        mol_type = protein
                        organism = synthetic construct
SEQUENCE: 87
QVQLKESGAE LVRSGASVKL SCTASGFNIK DYYMHWVKQR PEQGLEWIGW IDPENGDTEY    60
APKFQGKATM TADTSSNTAY LQLSSLTSED TAVYYCNAFY YDYDGYAMDY WGQGTSVTVS    120

SEQ ID NO: 88           moltype = AA  length = 108
FEATURE                 Location/Qualifiers
REGION                  1..108
                        note = TF1413-03e005 L Chain V Region
source                  1..108
                        mol_type = protein
                        organism = synthetic construct
SEQUENCE: 88
DVVMTQTPSS LSASLGERVS LTCRASQEIS GYLSWLQQKP DGTIKRLIYA ASTLDSGVPK    60
RFSGSRSGSD YSLTISSLES EDFADYYCLQ YASYPLTFGA GTKLELKR                108

SEQ ID NO: 89           moltype = AA  length = 451
FEATURE                 Location/Qualifiers
REGION                  1..451
                        note = TF1413-03e005 H Chain
source                  1..451
                        mol_type = protein
                        organism = synthetic construct
SEQUENCE: 89
QVQLKESGAE LVRSGASVKL SCTASGFNIK DYYMHWVKQR PEQGLEWIGW IDPENGDTEY    60
APKFQGKATM TADTSSNTAY LQLSSLTSED TAVYYCNAFY YDYDGYAMDY WGQGTSVTVS    120
RAKTTAPSVY PLAPVCGDTT GSSVTLGCLV KGYFPEPVTL TWNSGSLSSG VHTFPAVLQS    180
DLYTLSSSVT VTSSTWPSQS ITCNVAHPAS STKVDKKIEP RGPTIKPCPP CKCPAPNLLG    240
GPSVFIFPPK IKDVLMISLS PIVTCVVVDV SEDDPDVQIS WFVNNVEVHT AQTQTHREDY    300
NSTLRVVSAL PIQHQDWMSG KEFKCKVNNK DLPAPIERTI SKPKGSVRAP QVYVLPPPEE    360
EMTKKQVTLT CMVTDFMPED IYVEWTNNGK TELNYKNTEP VLDSDGSYFM YSKLRVEKKN    420
WVERNSYSCS VVHEGLHNHH TTKSFSRTPG K                                  451

SEQ ID NO: 90           moltype = AA  length = 214
FEATURE                 Location/Qualifiers
REGION                  1..214
                        note = TF1413-03e005 L Chain
source                  1..214
                        mol_type = protein
                        organism = synthetic construct
SEQUENCE: 90
DVVMTQTPSS LSASLGERVS LTCRASQEIS GYLSWLQQKP DGTIKRLIYA ASTLDSGVPK    60
RFSGSRSGSD YSLTISSLES EDFADYYCLQ YASYPLTFGA GTKLELKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 91           moltype = AA  length = 5
FEATURE                 Location/Qualifiers
REGION                  1..5
                        note = TF1413-03e015 H Chain CDR 1
```

```
source                   1..5
                         mol_type = protein
                         organism = synthetic construct
SEQUENCE: 91
GYTMN                                                                    5

SEQ ID NO: 92            moltype = AA   length = 17
FEATURE                  Location/Qualifiers
REGION                   1..17
                         note = TF1413-03e015 H Chain CDR 2
source                   1..17
                         mol_type = protein
                         organism = synthetic construct
SEQUENCE: 92
LINPYNGGTS YNQKFKG                                                       17

SEQ ID NO: 93            moltype = AA   length = 11
FEATURE                  Location/Qualifiers
REGION                   1..11
                         note = TF1413-03e015 H Chain CDR 3
source                   1..11
                         mol_type = protein
                         organism = synthetic construct
SEQUENCE: 93
GDYYPPYAMD Y                                                             11

SEQ ID NO: 94            moltype = AA   length = 11
FEATURE                  Location/Qualifiers
REGION                   1..11
                         note = TF1413-03e015 L Chain CDR 1
source                   1..11
                         mol_type = protein
                         organism = synthetic construct
SEQUENCE: 94
KASQNVGTNV A                                                             11

SEQ ID NO: 95            moltype = AA   length = 7
FEATURE                  Location/Qualifiers
REGION                   1..7
                         note = TF1413-03e015 L Chain CDR 2
source                   1..7
                         mol_type = protein
                         organism = synthetic construct
SEQUENCE: 95
SASYRYS                                                                  7

SEQ ID NO: 96            moltype = AA   length = 9
FEATURE                  Location/Qualifiers
REGION                   1..9
                         note = TF1413-03e015 L Chain CDR 3
source                   1..9
                         mol_type = protein
                         organism = synthetic construct
SEQUENCE: 96
QQYNRYPLT                                                                9

SEQ ID NO: 97            moltype = AA   length = 119
FEATURE                  Location/Qualifiers
REGION                   1..119
                         note = TF1413-03e015 H Chain V Region
source                   1..119
                         mol_type = protein
                         organism = synthetic construct
SEQUENCE: 97
EVQLQQSGPE LVKPGASMKI SCKASGYSFT GYTMNWVKQS HGKNLEWIGL INPYNGGTSY         60
NQKFKGKATL TVDKSSSTAY MELLSLTSED SAVYYCARGD YYPPYAMDYW GQGTSVTVS          119

SEQ ID NO: 98            moltype = AA   length = 108
FEATURE                  Location/Qualifiers
REGION                   1..108
                         note = TF1413-03e015 L Chain V Region
source                   1..108
                         mol_type = protein
                         organism = synthetic construct
SEQUENCE: 98
DIVMSQSPKF MSTSVGDRVS VTCKASQNVG TNVAWYQQKP GQSPKPLIYS ASYRYSGVPD         60
RFTGSGSGTD FTLTISNVQS EDLAEYFCQQ YNRYPLTFGV GTKLEIKR                      108

SEQ ID NO: 99            moltype = AA   length = 450
```

```
FEATURE                 Location/Qualifiers
REGION                  1..450
                        note = TF1413-03e015 H Chain
source                  1..450
                        mol_type = protein
                        organism = synthetic construct
SEQUENCE: 99
EVQLQQSGPE LVKPGASMKI SCKASGYSFT GYTMNWVKQS HGKNLEWIGL INPYNGGTSY    60
NQKFKGKATL TVDKSSSTAY MELLSLTSED SAVYYCARGD YYPPYAMDYW GQGTSVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNLLGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LPAPIERTIS KPKGSVRAPQ VYVLPPPEEE   360
MTKKQVTLTC MVTDFMPEDI YVEWTNNGKT ELNYKNTEPV LDSDGSYFMY SKLRVEKKNW   420
VERNSYSCSV VHEGLHNHHT TKSFSRTPGK                                   450

SEQ ID NO: 100          moltype = AA  length = 214
FEATURE                 Location/Qualifiers
REGION                  1..214
                        note = TF1413-03e015 L Chain
source                  1..214
                        mol_type = protein
                        organism = synthetic construct
SEQUENCE: 100
DIVMSQSPKF MSTSVGDRVS VTCKASQNVG TNVAWYQQKP GQSPKPLIYS ASYRYSGVPD    60
RFTGSGSGTD FTLTISNVQS EDLAEYFCQQ YNRYPLTFGV GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                              214

SEQ ID NO: 101          moltype = AA  length = 5
FEATURE                 Location/Qualifiers
REGION                  1..5
                        note = TF1413-03e034 H Chain CDR 1
source                  1..5
                        mol_type = protein
                        organism = synthetic construct
SEQUENCE: 101
GYNMN                                                                5

SEQ ID NO: 102          moltype = AA  length = 17
FEATURE                 Location/Qualifiers
REGION                  1..17
                        note = TF1413-03e034 H Chain CDR 2
source                  1..17
                        mol_type = protein
                        organism = synthetic construct
SEQUENCE: 102
NIDPYYGGTS YNQKFKG                                                  17

SEQ ID NO: 103          moltype = AA  length = 10
FEATURE                 Location/Qualifiers
REGION                  1..10
                        note = TF1413-03e034 H Chain CDR 3
source                  1..10
                        mol_type = protein
                        organism = synthetic construct
SEQUENCE: 103
GNYGYYAMDY                                                          10

SEQ ID NO: 104          moltype = AA  length = 11
FEATURE                 Location/Qualifiers
REGION                  1..11
                        note = TF1413-03e034 L Chain CDR 1
source                  1..11
                        mol_type = protein
                        organism = synthetic construct
SEQUENCE: 104
KASQNVRTAV A                                                        11

SEQ ID NO: 105          moltype = AA  length = 7
FEATURE                 Location/Qualifiers
REGION                  1..7
                        note = TF1413-03e034 L Chain CDR 2
source                  1..7
                        mol_type = protein
                        organism = synthetic construct
SEQUENCE: 105
LASNRHT                                                              7
```

```
SEQ ID NO: 106            moltype = AA  length = 9
FEATURE                   Location/Qualifiers
REGION                    1..9
                          note = TF1413-03e034 L Chain CDR 3
source                    1..9
                          mol_type = protein
                          organism = synthetic construct
SEQUENCE: 106
LQHWNYPLT                                                                  9

SEQ ID NO: 107            moltype = AA  length = 118
FEATURE                   Location/Qualifiers
REGION                    1..118
                          note = TF1413-03e034 H Chain V Region
source                    1..118
                          mol_type = protein
                          organism = synthetic construct
SEQUENCE: 107
EVQLQQSGPE LEKPGASVKI SCKASGYSFT GYNMNWVKQS NGKSLEWIGN IDPYYGGTSY           60
NQKFKGKATL TVDKSSSTAY MQLKSLTSED SAVYYCARGN YGYYAMDYWG QGTSVTVS            118

SEQ ID NO: 108            moltype = AA  length = 108
FEATURE                   Location/Qualifiers
REGION                    1..108
                          note = TF1413-03e034 L Chain V Region
source                    1..108
                          mol_type = protein
                          organism = synthetic construct
SEQUENCE: 108
DIVMSQSPKF MSTSVGDRVS ITCKASQNVR TAVAWYQQKP GQSPKALIYL ASNRHTGVPD           60
RFTGSGSGTD FTLTISNVQS EDLADYFCLQ HWNYPLTFGA GTKLELKR                      108

SEQ ID NO: 109            moltype = AA  length = 449
FEATURE                   Location/Qualifiers
REGION                    1..449
                          note = TF1413-03e034 H Chain
source                    1..449
                          mol_type = protein
                          organism = synthetic construct
SEQUENCE: 109
EVQLQQSGPE LEKPGASVKI SCKASGYSFT GYNMNWVKQS NGKSLEWIGN IDPYYGGTSY           60
NQKFKGKATL TVDKSSSTAY MQLKSLTSED SAVYYCARGN YGYYAMDYWG QGTSVTVSSA          120
KTTAPSVYPL APVCGDTTGS SVTLGCLVKG YFPEPVTLTW NSGSLSSGVH TFPAVLQSDL          180
YTLSSSVTVT SSTWPSQSIT CNVAHPASST KVDKKIEPRG PTIKPCPPCK CPAPNLLGGP          240
SVFIFPPKIK DVLMISLSPI VTCVVVDVSE DDPDVQISWF VNNVEVHTAQ TQTHREDYNS          300
TLRVVSALPI QHQDWMSGKE FKCKVNNKDL PAPIERTISK PKGSVRAPQV YVLPPPEEEM          360
TKKQVTLTCM VTDFMPEDIY VEWTNNGKTE LNYKNTEPVL DSDGSYFMYS KLRVEKKNWV          420
ERNSYSCSVV HEGLHNHHTT KSFSRTPGK                                           449

SEQ ID NO: 110            moltype = AA  length = 214
FEATURE                   Location/Qualifiers
REGION                    1..214
                          note = TF1413-03e034 L Chain
source                    1..214
                          mol_type = protein
                          organism = synthetic construct
SEQUENCE: 110
DIVMSQSPKF MSTSVGDRVS ITCKASQNVR TAVAWYQQKP GQSPKALIYL ASNRHTGVPD           60
RFTGSGSGTD FTLTISNVQS EDLADYFCLQ HWNYPLTFGA GTKLELKRAD AAPTVSIFPP          120
SSEQLTSGGA SVVCFLNNFY PKDINVKWKI DGSERQNGVL NSWTDQDSKD STYSMSSTLT          180
LTKDEYERHN SYTCEATHKT STSPIVKSFN RNEC                                     214

SEQ ID NO: 111            moltype = DNA  length = 354
FEATURE                   Location/Qualifiers
misc_feature              1..354
                          note = TF1413-02d028 H Chain V Region Gene
source                    1..354
                          mol_type = other DNA
                          organism = synthetic construct
SEQUENCE: 111
caggtgcagc tgaaggagtc aggacctgag ctggagaagc ctggtgcttc agtgaagata           60
tcctgcaagg cttctggtta ctcattcact ggctacaaca tgaactgggt gaagcagagc          120
aatggaaaga gccttgagtg gattggaaat attgatcctt actatggtgg tactagctac          180
aaccagaagt tcaagggcaa ggccacattg actgtagaca aatcctccag cacagctac           240
atgcagctca agagcctgac atctgaggac tctgcagtct attactgtgc aagaggagac          300
tatagggcgt actactttga ctactggggc caaggcacca ctctcacagt ctcg               354

SEQ ID NO: 112            moltype = DNA  length = 324
FEATURE                   Location/Qualifiers
```

```
misc_feature            1..324
                        note = TF1413-02d028 L Chain V Region Gene
source                  1..324
                        mol_type = other DNA
                        organism = synthetic construct
SEQUENCE: 112
gacattcaga tgacccagtc tccaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atcctctcac gttcggtgct   300
gggaccaagc tggagctgaa acgg                                          324

SEQ ID NO: 113          moltype = DNA  length = 1347
FEATURE                 Location/Qualifiers
misc_feature            1..1347
                        note = TF1413-02d028 H Chain Gene
source                  1..1347
                        mol_type = other DNA
                        organism = synthetic construct
SEQUENCE: 113
caggtgcagc tgaaggagtc aggacctgag ctggagaagc ctggtgcttc agtgaagata    60
tcctgcaagg cttctggtta ctcattcact ggctacaaca tgaactgggt gaagcagagc   120
aatggaaaga gccttgagtg gattggaaat attgatcctt actatggtgg tactagctac   180
aaccagaagt tcaagggcaa ggccacattg actgtagaca atcctccag cacagcctac   240
atgcagctca gagcctgac atctgaggac tctgcagtct attactgtgc aagaggagac   300
tatagggcgt actactttga ctactggggc caaggcacca ctctcacagt ctcgagcgcc   360
aaaacaacag ccccatcggt ctatccactg gcccctgtgt gtggagatac aactggctcc   420
tcggtgactc taggatgcct ggtcaagggt tatttccctg agccagtgac cttgacctgg   480
aactctggat ccctgtccag tggtgtgcac accttcccag ctgtcctgca gtctgacctc   540
tacaccctca gcagctcagt gactgtaacc tcgagcacct ggcccagcca gtccatcacc   600
tgcaatgtgg cccaccggc aagcagcacc aaggtggaca gaaaattga ccccggga     660
cccacaatca gccctgtcc tccatgcaaa tgcccagcac ctaacctctt gggtggacca   720
tccgtcttca tcttccctcc aaagatcaag gtgtactca tgatctccct gagcccata    780
gtcacatgtg tggtggtgga tgtgagcgag gatgacccag atgtccagat cagctggttt   840
gtgaacaacg tggaagtaca cacagctcag acacaaaccc atagagagga ttacaacagt   900
actctccggg tggtcagtgc cctccccatc cagcaccagg actggatgag tggcaaggag   960
ttcaaatgca aggtcaacaa caaagacctc ccagcgccca tcgagagaac catctcaaaa  1020
cccaaagggt cagtaagagc tccacaggta tatgtcttgc ctccaccaga agaagagatg  1080
actaagaaac aggtcactct gacctgcatg gtcacagact tcatgcctga agacatttac  1140
gtggagtgga ccaacaacgg gaaaacagag ctaaactaca agaacactga accagtcctg  1200
gactctgatg gttcttactt catgtacagc aagctgagag tggaaagaa gaactgggtg  1260
gaaagaaata gctactcctg ttcagtggtc acgagggtc tgcacaatca ccacgact    1320
aagagcttct cccggactcc gggtaaa                                     1347

SEQ ID NO: 114          moltype = DNA  length = 642
FEATURE                 Location/Qualifiers
misc_feature            1..642
                        note = TF1413-02d028 H Chain Gene
source                  1..642
                        mol_type = other DNA
                        organism = synthetic construct
SEQUENCE: 114
gacattcaga tgacccagtc tccaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atcctctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cacccttacg   540
ttgaccaagg acgagtatga acgacataac agctatacct gtgaggccac tcacaagaca   600
tcaacttcac ccattgtcaa gagcttcaac aggaatgagt gt                     642

SEQ ID NO: 115          moltype = DNA  length = 351
FEATURE                 Location/Qualifiers
misc_feature            1..351
                        note = TF1413-02d039 H Chain V Region Gene
source                  1..351
                        mol_type = other DNA
                        organism = synthetic construct
SEQUENCE: 115
gaagtgaagc tggtggagtc tgggggaggc ttagtgaagc ctggagggtc cctgaaactc    60
tcctgtgcag cctctggatt cgctttcagt agctatgaca tgtcttggt tcgccagact   120
ccggagaaga ggctggagtg gtcgcatac attagtagtg gtggtggtag cacctactat   180
ccagacactg tgaggggccg attcaccatc tccagagaca tgccaagaa caccctgtac   240
ctgcaaatga gcagtctgaa gtctgaggac acagccatgt attactgtgc aagaaggaga   300
ttacgacgag ctatggacta ctggggtcaa ggaacctcag tcaccgtctc g           351
```

| SEQ ID NO: 116 | moltype = DNA length = 339 |
| --- | --- |
| FEATURE | Location/Qualifiers |
| misc_feature | 1..339 |
| | note = TF1413-02d039 L Chain V Region Gene |
| source | 1..339 |
| | mol_type = other DNA |
| | organism = synthetic construct |

SEQUENCE: 116
```
gatgttgtga tgacccaaac tccactctcc ctgcctgtca gtcttggaga tcaagcctcc   60
atctcttgca gatctagtca gagccttgta cacagtaatg aaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
ctcacgttcg gtgctgggac caagctggag ctgaaacgg                          339
```

| SEQ ID NO: 117 | moltype = DNA length = 1344 |
| --- | --- |
| FEATURE | Location/Qualifiers |
| misc_feature | 1..1344 |
| | note = TF1413-02d039 H Chain Gene |
| source | 1..1344 |
| | mol_type = other DNA |
| | organism = synthetic construct |

SEQUENCE: 117
```
gaagtgaagc tggtggagtc tgggggaggc ttagtgaagc ctggagggtc cctgaaactc   60
tcctgtgcag cctctggatt cgctttcagt agctatgaca tgtcttgggt tcgccagact  120
ccggagaaga ggctggagtg ggtcgcatac attagtagtg gtggtggtag cacctactat  180
ccagacactg tgaagggccg attcaccatc tccagagaca atgccaagaa caccctgtac  240
ctgcaaatga gcagtctgaa gtctgaggac acagccatgt attactgtgc aagaagagga  300
ttacgacgag ctatgactac tgggggtcaa ggaacctgca tcaccgtctc gagcgccaaa  360
acaacagccc catcggtcta tccactggcc cctgtgtgtg gagatacaac tggctcctcg  420
gtgactctag gatgcctggt caaggggtat ttccctgagc cagtgacctt gacctggaac  480
tctggatccc tgtccagtgg tgtgcacacc ttcccagctg tcctgcagtc tgacctctac  540
accctcagca gctcagtgac tgtaacctcg agcacctggc ccagccagtc catcacctgc  600
aatgtggccc accccggcaag cagcaccaag gtggacaaga aattgagcc ccggggaccc  660
acaatcaagc cctgtcctcc atgcaaatgc ccagcaccta acctcttggg tggaccatcc  720
gtcttcatct tccctccaaa gatcaaggat gtactcatga tctccctgag ccccatagtc  780
acatgtgtgg tggtggatgt gagcgaggat gacccagatg tccagatcag ctggtttgtg  840
aacaacgtgg aagtacacac agctcagaca caaacccata gcgaggatta caacagtact  900
ctccgggtgg tcagtgccct ccccatccag caccaggact ggatgagtgg caaggagttc  960
aaatgcaagg tcaacaacaa agacctccca gcgcccatcg agagaaccat ctcaaaaccc 1020
aaaggggtcag taagagctcc acaggtatat gtcttgcctc caccagaaga agagatgact 1080
aagaaacagg tcactctgac ctgcatggtc acagacttca tgcctgaaga catttacgtg 1140
gagtggacca acaacgggaa aacagagcta aactacaaga acactgaacc agtcctggac 1200
tctgatggtt cttacttcat gtacagcaag ctgagagtgg aaaagaagaa ctgggtggaa 1260
agaaatagct actcctgttc agtggtccac gagggtctgc acaatcacca cacgactaag 1320
agcttctccc ggactccggg taaa                                        1344
```

| SEQ ID NO: 118 | moltype = DNA length = 657 |
| --- | --- |
| FEATURE | Location/Qualifiers |
| misc_feature | 1..657 |
| | note = TF1413-02d039 L Chain Gene |
| source | 1..657 |
| | mol_type = other DNA |
| | organism = synthetic construct |

SEQUENCE: 118
```
gatgttgtga tgacccaaac tccactctcc ctgcctgtca gtcttggaga tcaagcctcc   60
atctcttgca gatctagtca gagccttgta cacagtaatg aaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
ctcacgttcg gtgctgggac caagctggag ctgaaacggg ctgatgctgc accaactgta  360
tccatcttcc caccatccag tgagcagtta acatctggag gtgcctcagt cgtgtgcttc  420
ttgaacaact tctaccccaa agacatcaat gtcaagtgga agattgatgg cagtgaacga  480
caaaatggcg tcctgaacag ttggactgat caggacagca aagacagcac ctacagcatg  540
agcagcaccc tcacgttgac caaggacgag tatgaacgac ataacagcta cctgtgtgag  600
gccactcaca cagacatcaac ttcacccatt gtcaagagct tcaacaggaa tgagtgt     657
```

| SEQ ID NO: 119 | moltype = DNA length = 345 |
| --- | --- |
| FEATURE | Location/Qualifiers |
| misc_feature | 1..345 |
| | note = TF1413-02e004 H Chain V Region Gene |
| source | 1..345 |
| | mol_type = other DNA |
| | organism = synthetic construct |

SEQUENCE: 119
```
caggtccagc tgcagcagtc tggggctgag cttgtgaagc ctggggctcc agtgaagctg   60
tcctgcaagg cttctggcta caccttcacc agctactgga tgaactgggt gaagcagagg  120
cctggacgag gccttgagtg gattggaagg attgatcctt ccgatagtga aactcactac  180
```

```
aatcaaaagt tcaaggacga ggccacactg actgtagaca aatcctccag cacagcctac    240
atccaactca gcagcctgac atctgaggac tctgcggtct attactgtgc aagagggtac    300
tatgctatgg actactgggg tcaaggaacc tcagtcaccg tctcg                   345
```

| SEQ ID NO: 120 | moltype = DNA  length = 321 |
|---|---|
| FEATURE | Location/Qualifiers |
| misc_feature | 1..321 |
| | note = TF1413-02e004 L Chain V Region Gene |
| source | 1..321 |
| | mol_type = other DNA |
| | organism = synthetic construct |

```
SEQUENCE: 120
gacattgtgc tgacccaatc tcccaaattc atgtccacat cagtaggaga cagggtcagc     60
atcacctgca aggccagtca ggatgtgagt actgctgtag cctggtatca acagaaacca    120
ggacaatctc ctaaactact gatttactca gcatcctacc ggtacactgg agtccctgat    180
cgcttcactg gcagtggatc tgggacggat ttcacttttca ccatcagcag tgtgcaggct    240
gaagacctgg cagtttatta ctgtcagcaa cattatagta ctccgacgtt cggtggaggc    300
accaagctgg aaatcaaacg g                                              321
```

| SEQ ID NO: 121 | moltype = DNA  length = 1338 |
|---|---|
| FEATURE | Location/Qualifiers |
| misc_feature | 1..1338 |
| | note = TF1413-02e004 H Chain Gene |
| source | 1..1338 |
| | mol_type = other DNA |
| | organism = synthetic construct |

```
SEQUENCE: 121
caggtccagc tgcagcagtc tggggctgag cttgtgaagc ctggggctcc agtgaagctg     60
tcctgcaagg cttctggcta caccttcacc agctactgga tgaactgggt gaagcagagg    120
cctggacgag gccttgagtg gattggaagg attgatcctt ccgatagtga aactcactac    180
aatcaaaagt tcaaggacga ggccacactg actgtagaca atcctccag cacagcctac     240
atccaactca gcagcctgac atctgaggac tctgcggtct attactgtgc aagagggtac    300
tatgctatgg actactgggg tcaaggaacc tcagtcaccg tctcgagcgc caaaacaaca    360
gccccatcgg tctatccact ggcccctgtg tgtggagata caactggctc ctcggtgact    420
ctaggatgcc tggtcaaggg ttatttccct gagccagtga ccttgacctg gaactctgga    480
tccctgtcca gtggtgtgca caccttccca gctgtcctgc agtctgacct ctacaccctc    540
agcagctcag tgactgtaac ctcgagcacc tggcccagcc agtccatcac ctgcaatgtg    600
gcccaccggg caagcagcac aaggtggac aagaaaattg agcccggggg acccacaatc    660
aagccctgtc ctccatgcaa atgcccagca cctaacctct tgggtggacc atccgtcttc    720
atcttccctc caaagatcaa ggatgtactc atgatctccc tgagccccat agtcacatgt    780
gtggtggtgg atgtgagcga ggatgaccca gatgtccaga tcagctggtt tgtgaacaac    840
gtggaagtac acacagctca gacacaaacc catagagagg attacaacag tactctccgg    900
gtggtcagtg ccctccccat ccagcaccag gactggatga gtggcaagga gttcaaatgc    960
aaggtcaaca acaaagacct cccagcgccc atcgagagaa ccatctcaaa acccaaaggg   1020
tcagtaagag ctccacaggt atatgtcttg cctccaccag aagaagagat gactaagaaa   1080
caggtcactc tgacctgcat ggtcacagac ttcatgcctg aagacattta cgtggagtgg   1140
accaacaacg ggaaaacaga gctaaactac aagaacactc aaccagtcct ggactctgat   1200
ggttcttact tcatgtacag caagctgaga gtgaaaaaga gaactggcct ggaaagaaat   1260
agctactcct gttcagtggt ccacgagggt ctgcacaatc accacacgac taagagcttc   1320
tcccggactc cgggtaaa                                                 1338
```

| SEQ ID NO: 122 | moltype = DNA  length = 639 |
|---|---|
| FEATURE | Location/Qualifiers |
| misc_feature | 1..639 |
| | note = TF1413-02e004 L Chain Gene |
| source | 1..639 |
| | mol_type = other DNA |
| | organism = synthetic construct |

```
SEQUENCE: 122
gacattgtgc tgacccaatc tcccaaattc atgtccacat cagtaggaga cagggtcagc     60
atcacctgca aggccagtca ggatgtgagt actgctgtag cctggtatca acagaaacca    120
ggacaatctc ctaaactact gatttactca gcatcctacc ggtacactgg agtccctgat    180
cgcttcactg gcagtggatc tgggacggat ttcactttca ccatcagcag tgtgcaggct    240
gaagacctgg cagtttatta ctgtcagcaa cattatagta ctccgacgtt cggtggaggc    300
accaagctgg aaatcaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgt                            639
```

| SEQ ID NO: 123 | moltype = DNA  length = 360 |
|---|---|
| FEATURE | Location/Qualifiers |
| misc_feature | 1..360 |
| | note = TF1413-02e014 H Chain V Region Gene |
| source | 1..360 |
| | mol_type = other DNA |
| | organism = synthetic construct |

SEQUENCE: 123

```
caggtgcagc tgaagcagtc aggggcagag cttgtgaggt caggggcctc agtcaagttg    60
tcctgcacag cttctggctt caacattaaa gactactata tgcactgggt gaagcagagg   120
cctgaacagg gcctggagtg gattggatgg attgatcctg agaatggtga tactgaatat   180
gccccgaagt tccagggcaa ggccactatg actgcagaca catcctccaa cacagcctac   240
ctgcagctca gcagcctgac atctgaggac actgccgtct attactgtaa tgcaggctac   300
tatgattacg acggctatgc tatggactac tggggtcaag aacctcagt caccgtctcg    360
```

SEQ ID NO: 124          moltype = DNA   length = 324
FEATURE                 Location/Qualifiers
misc_feature            1..324
                        note = TF1413-02e014 L Chain V Region Gene
source                  1..324
                        mol_type = other DNA
                        organism = synthetic construct
SEQUENCE: 124

```
gacattgtgc tgacacagtc tcccaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtcccgat    180
cgcttcacag gcagtggatc tgggacagat ttcactctca ccattagcaa tgtgcagtct   240
gaagacttgg cagattattt ctgtcagcaa tatagcagct atcctctgac gttcggtgga   300
ggcaccaagc tggaaatcaa acgg                                           324
```

SEQ ID NO: 125          moltype = DNA   length = 1353
FEATURE                 Location/Qualifiers
misc_feature            1..1353
                        note = TF1413-02e014 H Chain Gene
source                  1..1353
                        mol_type = other DNA
                        organism = synthetic construct
SEQUENCE: 125

```
caggtgcagc tgaagcagtc aggggcagag cttgtgaggt caggggcctc agtcaagttg    60
tcctgcacag cttctggctt caacattaaa gactactata tgcactgggt gaagcagagg   120
cctgaacagg gcctggagtg gattggatgg attgatcctg agaatggtga tactgaatat   180
gccccgaagt tccagggcaa ggccactatg actgcagaca catcctccaa cacagcctac   240
ctgcagctca gcagcctgac atctgaggac actgccgtct attactgtaa tgcaggctac   300
tatgattacg acggctatgc tatggactac tggggtcaag aacctcagt caccgtctcg    360
agcgccaaaa aaacagcccc atcggtctat ccactggccc ctgtgtgtgg agatacaact   420
ggctcctcgg tgactctagg atgcctggtc aagggttatt tccctgagcc agtgaccttg   480
acctggaact ctggatccct gtccagtggt gtgcacactt tcccagctgt cctgcagtct   540
gacctctaca ccctcagcag ctcagtgact gtaacctcga gcacctggcc cagccagtcc   600
atcacctgca atgtggccca cccggcaagc agtaccaagg tggacaagaa aattgagccc   660
cggggaccca caatcaagcc ctgtcctcca tgcaaatgcc cagcacctaa cctcttgggt   720
ggaccatccg tcttcatctt ccctccaaag atcaaggatg tactcatgat ctcccctgag   780
cccatagtca catgtgtggt ggtgatgtg agcgaggatg acccagatgt ccagatcagc   840
tggtttgtga acaacgtgga agtacacaca gctcagacac aaaccatag agaggattac    900
aacagtactc tccgggtggt cagtgccctc cccatccagc accaggactg gatgagtggc   960
aaggagttca aatgcaaggt caacaacaaa gaccteccg cgcccatcga gagaaccatc  1020
tcaaaaccca aagggtcagt aagagctcca caggtatatg tcttgcctcc accagaagaa  1080
gagatgacta agaaacaggt cactctgacc tgcatggtca cagacttcat gcctgaagac  1140
atttacgtgg agtggaccaa caacgggaaa acagagctaa actacaagaa cactgaacca  1200
gtcctggact ctgatggttc ttacttcatg tacagcaagc tgagagtgga aaagaagaac  1260
tgggtggaaa gaaatagcta ctcctgttca gtggtccacg agggtctgca caatcaccac  1320
acgactaaga gcttctcccg gactccgggt aaa                              1353
```

SEQ ID NO: 126          moltype = DNA   length = 642
FEATURE                 Location/Qualifiers
misc_feature            1..642
                        note = TF1413-02e014 L Chain Gene
source                  1..642
                        mol_type = other DNA
                        organism = synthetic construct
SEQUENCE: 126

```
gacattgtgc tgacacagtc tcccaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtcccgat    180
cgcttcacag gcagtggatc tgggacagat ttcactctca ccattagcaa tgtgcagtct   240
gaagacttgg cagattattt ctgtcagcaa tatagcagct atcctctgac gttcggtgga   300
ggcaccaagc tggaaatcaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                       642
```

SEQ ID NO: 127          moltype = DNA   length = 351
FEATURE                 Location/Qualifiers
misc_feature            1..351
                        note = TF1413-02e030 H Chain V Region Gene
source                  1..351

```
                         mol_type = other DNA
                         organism = synthetic construct
SEQUENCE: 127
gaggttcagc ttcagcagtc tggggctgag cttgtgaggc caggggcctt agtcaagttg    60
tcctgcaaag cttctggctt caacattaaa gactactata tgcactgggt gaagcagagg   120
cctgaacagg gcctggagtg gattggatgg attgatcctg agaatggtaa cactatatat   180
gacccgaagt tccagggcaa ggccagtata acagcagaca catcctccaa cacagcctac   240
ctgcagctca gcagcctgac atctgaggac actgccgtct attactgtgc tatatctact   300
atgattacga cccttgacta ctggggccaa ggcaccactc tcacagtctc g            351

SEQ ID NO: 128          moltype = DNA  length = 342
FEATURE                 Location/Qualifiers
misc_feature            1..342
                         note = TF1413-02e030 L Chain V Region Gene
source                  1..342
                         mol_type = other DNA
                         organism = synthetic construct
SEQUENCE: 128
gacatccaga tgacccagtc tccatcctcc ctggctatgt cagtagggca gaaggtcact    60
atgagctgca agtccagtca gagcctttta aatagtagca tcaaaagaa ctatttggcc   120
tggtaccagc agaaaccagg acagtctcct aaacttctgg tatactttgc atccactagg   180
gaatctgggg tccctgatcg cttcataggc agtggatctg gacagattt cactcttacc   240
atcagcagtg tgcaggctga agacctggca gattacttct gtcagcaaca ttatagcact   300
ccgctcacgt tcggtgctgg gaccaagctg gagctgaaac gg                     342

SEQ ID NO: 129          moltype = DNA  length = 1344
FEATURE                 Location/Qualifiers
misc_feature            1..1344
                         note = TF1413-02e030 H Chain Gene
source                  1..1344
                         mol_type = other DNA
                         organism = synthetic construct
SEQUENCE: 129
gaggttcagc ttcagcagtc tggggctgag cttgtgaggc caggggcctt agtcaagttg    60
tcctgcaaag cttctggctt caacattaaa gactactata tgcactgggt gaagcagagg   120
cctgaacagg gcctggagtg gattggatgg attgatcctg agaatggtaa cactatatat   180
gacccgaagt tccagggcaa ggccagtata acagcagaca catcctccaa cacagcctac   240
ctgcagctca gcagcctgac atctgaggac actgccgtct attactgtgc tatatctact   300
atgattacga cccttgacta ctggggccaa ggcaccactc tcacagtctc gagcgccaaa   360
acaacagccc catcggtcta tccactggcc cctgtgtgtg agatacaac tggctcctcg    420
gtgactctag gatgcctggt caagggttat tccctgagc cagtgacctt gacctggaac   480
tctggatccc tgtccagtgg tgtgcacacc ttcccagctc ctgcagtc tgacctctac     540
accctccagca gctcagtgac tgtaacctcg agcacctgc tcagcagtc catcacctgc   600
aatgtggccc accccggcaag cagcaccaag gtggacaaga aaattgagcc ccggggaccc   660
acaatcaagc cctgtcctcc atgcaaatgc ccagcccta acttctggg tggaccatcc    720
gtcttcatct tccctccaaa gatcaaggat gtactcatga tctccctgag ccccatagtc   780
acatgtgtgg tggtggatgt gagcgaggat gaccagatg tccagatcag ctggtttgtg   840
aacaacgtgg aagtacacac agctcagaca caaacccata gagaggatta acagtact     900
ctccgggtgg tcagtgccct ccccatccag caccaggact ggatgagtgg caaggagttc   960
aaatgcaagg tcaacaacaa agacctccca gcgcccatcg agaaccat ctcaaaaccc    1020
aaagggtcag taagagctcc acaggtatat gtcttgcctc caccagaaga gagatgact   1080
aagaaacagg tcactctgac ctgcatggtc acagacttca tgcctgaaga catttacgtg   1140
gagtggacca caacgggaa acagagcta aactacaaga cactgaacc agtcctggac    1200
tctgatggtt cttacttcat gtacagcaag ctgagagtgg aaaagaagaa ctgggtgaaa   1260
agaaatagct actcctgttc agtggtccac gagggtctgc acaatcacca cacgactaag   1320
agcttctccc ggactccggg taaa                                           1344

SEQ ID NO: 130          moltype = DNA  length = 660
FEATURE                 Location/Qualifiers
misc_feature            1..660
                         note = TF1413-02e030 L Chain Gene
source                  1..660
                         mol_type = other DNA
                         organism = synthetic construct
SEQUENCE: 130
gacatccaga tgacccagtc tccatcctcc ctggctatgt cagtagggca gaaggtcact    60
atgagctgca agtccagtca gagcctttta aatagtagca tcaaaagaa ctatttggcc   120
tggtaccagc agaaaccagg acagtctcct aaacttctgg tatactttgc atccactagg   180
gaatctgggg tccctgatcg cttcataggc agtggatctg gacagattt cactcttacc   240
atcagcagtg tgcaggctga agacctggca gattacttct gtcagcaaca ttatagcact   300
ccgctcacgt tcggtgctgg gaccaagctg gagctgaaac gggctgatgc tgcaccaact   360
gtatccatct tcccaccatc cagtgagcag ttaacatctg aggtgcctc agtcgtgtgc   420
ttcttgaaca acttctaccc caaagacatc aatgtcaagt ggaagattga tggcagtgaa   480
cgacaaaatg gcgtcctgaa cagttggact gatcaggaca gcaaagacag cacctacagc   540
atgagcagca ccctcacgtt gaccaaggac gagtatgaac acataacag ctataccgt    600
gaggccactc acaagacatc aacttccccc attgtcaaga gcttcaacag gaatgagtgt   660

SEQ ID NO: 131          moltype = DNA  length = 348
FEATURE                 Location/Qualifiers
```

```
misc_feature            1..348
                        note = TF1413-02e040 H Chain V Region Gene
source                  1..348
                        mol_type = other DNA
                        organism = synthetic construct
SEQUENCE: 131
gaagtgatgc tggtggagtc tggacctgag ctggtgaagc ctggagcttc aatgaagata    60
tcctgcaagg cttctggtta ctcattcact ggctacacca tgaactgggt gaagcagagc   120
catggaaaga accttgagtg gattggactt attaatcctt acaatggtgg tactagctac   180
aaccagaatt ttaagggcaa ggccacatta actgtagaca agtcatccag cacagcctac   240
atggagctcc tcagtctgac atctgaggac tctgcagtct attactgtgc aagagggtac   300
tacggtcgct ttgactactg gggccaaggc accactctca cagtctcg                348

SEQ ID NO: 132          moltype = DNA   length = 324
FEATURE                 Location/Qualifiers
misc_feature            1..324
                        note = TF1413-02e040 L Chain V Region Gene
source                  1..324
                        mol_type = other DNA
                        organism = synthetic construct
SEQUENCE: 132
gacatcttgc tgactcagtc tccaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atcctctcac gttcggtgct   300
gggaccaagc tggagctgaa acgg                                          324

SEQ ID NO: 133          moltype = DNA   length = 1341
FEATURE                 Location/Qualifiers
misc_feature            1..1341
                        note = TF1413-02e040 H Chain Gene
source                  1..1341
                        mol_type = other DNA
                        organism = synthetic construct
SEQUENCE: 133
gaagtgatgc tggtggagtc tggacctgag ctggtgaagc ctggagcttc aatgaagata    60
tcctgcaagg cttctggtta ctcattcact ggctacacca tgaactgggt gaagcagagc   120
catggaaaga accttgagtg gattggactt attaatcctt acaatggtgg tactagctac   180
aaccagaatt ttaagggcaa ggccacatta actgtagaca agtcatccag cacagcctac   240
atggagctcc tcagtctgac atctgaggac tctgcagtct attactgtgc aagagggtac   300
tacggtcgct ttgactactg gggccaaggc accactctca cagtctcgag cgccaaaaca   360
acagccccat cggtctatcc actggccccc tgtgtgtgga caactggtcc tcctcggtg   420
actctaggat gcctggtcaa gggttatttc cctgagccag tgaccttgac ctggaactct   480
ggatccctgt ccagtggtgt gcacaccttc ccagctgtcc tgcagtctga cctctacacc   540
ctcagcagct cagtgactgt aacctcgagc acctggccca gccagtccat cacctgcaat   600
gtggcccacc cggcaagcag caccaaggtg gacaagaaaa ttgagcccg gggaccacca   660
atcaagccct gtcctccatg caaatgccca gcacctaacc tcttgggtgg accatccgtc   720
ttcatcttcc ctccaaagat caaggatgta ctcatgatct ccctgagccc catagtcaca   780
tgtgtggtgg tggatgtgag cgaggatgac ccagatgtcc agatcagctg gtttgtgaac   840
aacgtggaag tacacacagc tcagacacaa acccataagg aggattacaa cagtactctc   900
cgggtggtca gtgccctccc catccagcac caggactgga tgagtggcaa ggagttcaaa   960
tgcaaggtca acaacaaaga cctcccagcg cccatcgaga aaccatctc aaaacccaaa   1020
gggtcagtaa gagctccaca ggtatatgtc ttgcctccac cagaagaaga gatgactaag   1080
aaacaggtca ctctgacctg catggtcaca gacttcatgc ctgaagacat ttacgtggag   1140
tggaccaaca acgggaaaac agagctaaac tacaagaaca ctgaaccagt cctggactct   1200
gatggttctt acttcatgta cagcaagctg agagtggaaa agaagaactg gtggaaaga   1260
aatagctact cctgttcagt ggtccacgag ggtctgcaca atcaccacac gactaagagc   1320
ttctccggga ctccgggtaa a                                             1341

SEQ ID NO: 134          moltype = DNA   length = 642
FEATURE                 Location/Qualifiers
misc_feature            1..642
                        note = TF1413-02e040 L Chain Gene
source                  1..642
                        mol_type = other DNA
                        organism = synthetic construct
SEQUENCE: 134
gacatcttgc tgactcagtc tccaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atcctctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cacccctacg   540
ttgaccaagg acgagtatga acgacataac agctatacct gtgaggccac tcacaagaca   600
tcaacttcac ccattgtcaa gagcttcaac aggaatgagt gt                      642
```

```
SEQ ID NO: 135          moltype = DNA   length = 345
FEATURE                 Location/Qualifiers
misc_feature            1..345
                        note = TF1413-03e001 H Chain V Region Gene
source                  1..345
                        mol_type = other DNA
                        organism = synthetic construct
SEQUENCE: 135
caggtgcagc tgaagcagtc aggacctgag ctggtgaagc ctggggcttc agtgaagata    60
tcctgcaagg cttctggtta ctcattcact ggctactaca tgcactgggt gaagcaaagc   120
catgtaaaga gccttgagtg gattggacgt attaatcctt acaatggtgc tactagctac   180
aaccagaatt tcaaggacaa ggccagcttg actgtagata gtcctccag cacagcctac    240
atggagctcc acagcctgac atctgaggac tctgcagtct attactgtgc aagaaactac   300
ggctactttg actactgggg ccaaggcacc actctcacag tctcg                   345

SEQ ID NO: 136          moltype = DNA   length = 324
FEATURE                 Location/Qualifiers
misc_feature            1..324
                        note = TF1413-03e001 L Chain V Region Gene
source                  1..324
                        mol_type = other DNA
                        organism = synthetic construct
SEQUENCE: 136
gacatcaaga tgacccagtc tccaaaattc atgtccacat cagtaggaga cagggtcagc    60
gtcacctgcg aggccagtca gaatgtggat aataatgtag tctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atcctctcac gttcggtgct   300
gggaccaagt tggaaataaa acgg                                          324

SEQ ID NO: 137          moltype = DNA   length = 1338
FEATURE                 Location/Qualifiers
misc_feature            1..1338
                        note = TF1413-03e001 H Chain Gene
source                  1..1338
                        mol_type = other DNA
                        organism = synthetic construct
SEQUENCE: 137
caggtgcagc tgaagcagtc aggacctgag ctggtgaagc ctggggcttc agtgaagata    60
tcctgcaagg cttctggtta ctcattcact ggctactaca tgcactgggt gaagcaaagc   120
catgtaaaga gccttgagtg gattggacgt attaatcctt acaatggtgc tactagctac   180
aaccagaatt tcaaggacaa ggccagcttg actgtagata gtcctccag cacagcctac    240
atggagctcc acagcctgac atctgaggac tctgcagtct attactgtgc aagaaactac   300
ggctactttg actactgggg ccaaggcacc actctcacag tctcgagcgc caaaacaaca   360
gccccatcgg tctatccact ggcccctgtg tgtggagata caactggctc ctcggtgact   420
ctaggatgcc tggtcaaggg ttatttccct gagccagtga ccttgacctg gaactctgga   480
tccctgtcca gtggtgtgca cacctttcca gctgtcctgc agtctgacct ctacaccctc   540
agcagctcag tgactgtaac ctcgagcacc tggcccagcc agtccatcac ctgcaatgtg   600
gcccaccccg caagcagcac caaggtggac aagaaaattg agcccgggg acccacaatc    660
aagccctgtc ctccatgcaa atgcccagca cctaacctct gggtggaca tccgtcttc     720
atcttccctc caaagatcaa ggatgtactc atgatctccc tgagccccat agtcacatgt   780
gtggtggtgg atgtgagcga ggatgaccca gatgtccaga tcagctggtt tgtgaacaac   840
gtggaagtac acacagctca gacacaaacc catagagagg attacaacag tactctccgg   900
gtggtcagtg ccctcccat ccagcaccag gactggatga gtggcaagga gttcaaatgc    960
aaggtcaaca acaaagacct cccagcgccc atcgagagaa ccatctcaaa acccaaaggg   1020
tcagtaagag ctccacaggt atatgtcttg cctccaccag aagaagagat gactaagaaa   1080
caggtcactc tgacctgcat ggtcacagac ttcatgcctg aagacattta cgtggagtgg   1140
accaacaacg ggaaaacaga gctaaactac aagaacactg aaccagtcct ggactctgat   1200
ggttcttact tcatgtacag caagctgaga gtggaaaaga gaactgggg agaaagaaat    1260
agctactcct gttcagtggt ccacgagggt ctgcacaatc accacgac taagagcttc    1320
tcccggactc cgggtaaa                                                 1338

SEQ ID NO: 138          moltype = DNA   length = 642
FEATURE                 Location/Qualifiers
misc_feature            1..642
                        note = TF1413-03e001 L Chain Gene
source                  1..642
                        mol_type = other DNA
                        organism = synthetic construct
SEQUENCE: 138
gacatcaaga tgacccagtc tccaaaattc atgtccacat cagtaggaga cagggtcagc    60
gtcacctgcg aggccagtca gaatgtggat aataatgtag tctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atcctctcac gttcggtgct   300
gggaccaagt tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
```

```
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

SEQ ID NO: 139           moltype = DNA   length = 345
FEATURE                  Location/Qualifiers
misc_feature             1..345
                         note = TF1413-03e004 H Chain V Region Gene
source                   1..345
                         mol_type = other DNA
                         organism = synthetic construct
SEQUENCE: 139
caggtgcagc tgaagcagtc aggggctgag cttgtgaagc ctggggctcc agtgaagctg     60
tcctgcaagg cttctggcta caccttcacc agctactgga tgaactgggt gaagcagagg    120
cctggacgag gcctcgagtg gattggaagg attgatcctt ccgatagtga aactcactac    180
aatcaaaagt tcaaggacaa ggccacactg actgtagaca atcctccag cacagcctac    240
atccaactca gcagcctgac atctgaggac tctgcggtct attactgtgc aagagggtac    300
tacggtagta actactgggg ccaaggcacc actctcacag tctcg                    345

SEQ ID NO: 140           moltype = DNA   length = 324
FEATURE                  Location/Qualifiers
misc_feature             1..324
                         note = TF1413-03e004 L Chain V Region Gene
source                   1..324
                         mol_type = other DNA
                         organism = synthetic construct
SEQUENCE: 140
gacatcaaga tgacccagtc tccaaaattc atgtccacat cagtaggaga cagggtcagc     60
gtcacctgca aggccagtca gaatgtgggt actaatgtag cctggtatca acagaaacca    120
gggcaatctc ctaaagcact gatttactcg gcatccaccg gtacagtgg agtccctgat    180
cgcttcacag gcagtggatc tgggacagat ttcactctca ccatcagcaa tgtgcagtct    240
gaagacttgg cagagtattt ctgtcagcaa tataacagct atcctctcac gttcggtgct    300
gggaccaagc tggagctgaa acgg                                           324

SEQ ID NO: 141           moltype = DNA   length = 1338
FEATURE                  Location/Qualifiers
misc_feature             1..1338
                         note = TF1413-03e004 H Chain Gene
source                   1..1338
                         mol_type = other DNA
                         organism = synthetic construct
SEQUENCE: 141
caggtgcagc tgaagcagtc aggggctgag cttgtgaagc ctggggctcc agtgaagctg     60
tcctgcaagg cttctggcta caccttcacc agctactgga tgaactgggt gaagcagagg    120
cctggacgag gcctcgagtg gattggaagg attgatcctt ccgatagtga aactcactac    180
aatcaaaagt tcaaggacaa ggccacactg actgtagaca atcctccag cacagcctac    240
atccaactca gcagcctgac atctgaggac tctgcggtct attactgtgc aagagggtac    300
tacggtagta actactgggg ccaaggcacc actctcacag tctcgagcgc caaaacaaca    360
gccccatcgg tctatccact ggcccctgtg tgtggagata caactggctc ctcggtgact    420
ctaggatgcc tggtcaaggg ttatttccct gagccagtga ccttgacctg gaactctgga    480
tccctgtcca gtggtgtgca caccttccca gctgtcctga gtctgacct ctacacctcc    540
agcagctcag tgactgtaac ctcgagcacc tggcccagcc agtccatcac ctgcaatgtg    600
gcccaccgg caagcagcac caaggtggac aagaaaattg agcccgggg acccacaatc    660
aagccctgtc ctccatgcaa atgcccagca cctaacctct gggtggacc atccgtcttc    720
atcttccctc caaagatcaa ggatgtactc atgatctcc tgagcccat agtcacatgt    780
gtggtggtgg atgtgagcga ggatgaccca gatgtccaga tcagctggtt tgtgaacaac    840
gtggaagtac acacagctca gacacaaacc catagagagg attacaacag tactctccgg    900
gtggtcagtg ccctccccat ccagcaccag gactggatga gtggcaagga gttcaaatgc    960
aaggtcaaca acaaagacct cccagcgccc atcgagagaa ccatctcaaa acccaaaggg   1020
tcagtaagag ctccacaggt atatgtcttg cctccaccag aagaagagat gactaagaa   1080
caggtcactc tgacctgcat ggtcacagac ttcatgcctg aagacattta cgtggagtgg   1140
accaacaacg ggaaaacaga gctaaactac aagaacactg aaccagtcct ggactctgat   1200
ggttcttact tcatgtacag caagctgaga gtggaaaaga gaactgggt ggaaagaaat   1260
agctactcct gttcagtggt ccacgagggt ctgcacaatc accacgac taagagcttc    1320
tcccgactc cgggtaaa                                                  1338

SEQ ID NO: 142           moltype = DNA   length = 642
FEATURE                  Location/Qualifiers
misc_feature             1..642
                         note = TF1413-03e004 L Chain Gene
source                   1..642
                         mol_type = other DNA
                         organism = synthetic construct
SEQUENCE: 142
gacatcaaga tgacccagtc tccaaaattc atgtccacat cagtaggaga cagggtcagc     60
gtcacctgca aggccagtca gaatgtgggt actaatgtag cctggtatca acagaaacca    120
gggcaatctc ctaaagcact gatttactcg gcatcctacc ggtacagtgg agtccctgat    180
cgcttcacag gcagtggatc tgggacagat ttcactctca ccatcagcaa tgtgcagtct    240
gaagacttgg cagagtattt ctgtcagcaa tataacagct atcctctcac gttcggtgct    300
```

```
gggaccaagc tggagctgaa acgggctgat gctgcaccaa ctgtatccat cttcccacca   360
tccagtgagc agttaacatc tggaggagcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642

SEQ ID NO: 143          moltype = DNA   length = 360
FEATURE                 Location/Qualifiers
misc_feature            1..360
                        note = TF1413-03e005 H Chain V Region Gene
source                  1..360
                        mol_type = other DNA
                        organism = synthetic construct
SEQUENCE: 143
caggtgcagc tgaaggagtc aggggcagag cttgtgaggt caggggcctc agtcaagttg    60
tcctgcacag cttctggctt caacattaaa gactactata tgcactgggt gaagcagagg   120
cctgaacagg gcctggagtg gattggatgg attgatcctg agaatggtga tactgaatat   180
gccccgaagt tccagggcaa ggccactatg actgcagaca catcctccaa cacagcctac   240
ctgcagctca gcagcctgac atctgaggac actgccgtct attactgtaa tgccttctac   300
tatgattacg acgggtatgc tatggactac tggggtcaag gaacctcagt caccgtctcg   360

SEQ ID NO: 144          moltype = DNA   length = 324
FEATURE                 Location/Qualifiers
misc_feature            1..324
                        note = TF1413-03e005 L Chain V Region Gene
source                  1..324
                        mol_type = other DNA
                        organism = synthetic construct
SEQUENCE: 144
gatgttgtga tgacccaaac tccatcctcc ttatctgcct ctctgggaga aagagtcagt    60
ctcacttgtc gggcaagtca ggaaattagt ggttacttaa gctggcttca gcagaaacca   120
gatggaacta ttaaacgcct gatctacgcc gcatccactt tagattctgg tgtcccaaaa   180
aggttcagtg gcagtaggtc tgggtcagat tattctctca ccatcagcag ccttgagtct   240
gaagattttg cagactatta ctgtctacaa tatgctagtt atccgctcac gttcggtgct   300
gggaccaagc tggagctgaa acgg                                          324

SEQ ID NO: 145          moltype = DNA   length = 1353
FEATURE                 Location/Qualifiers
misc_feature            1..1353
                        note = TF1413-03e005 H Chain Gene
source                  1..1353
                        mol_type = other DNA
                        organism = synthetic construct
SEQUENCE: 145
caggtgcagc tgaaggagtc aggggcagag cttgtgaggt caggggcctc agtcaagttg    60
tcctgcacag cttctggctt caacattaaa gactactata tgcactgggt gaagcagagg   120
cctgaacagg gcctggagtg gattggatgg attgatcctg agaatggtga tactgaatat   180
gccccgaagt tccagggcaa ggccactatg actgcagaca catcctccaa cacagcctac   240
ctgcagctca gcagcctgac atctgaggac actgccgtct attactgtaa tgccttctac   300
tatgattacg acgggtatgc tatggactac tggggtcaag gaacctcagt caccgtctcg   360
agggccaaaa caacagcccc atcggtctat ccactggccc ctgtgtgtgg agatacaact   420
ggctcctcgg tgactctagg atgcctggtc aaggggtatt tccctgagcc agtgaccttg   480
acctggaact ctgatcccct gtccagtggt gtgcacacct tcccagctgt cctgcagtct   540
gacctctaca cccctcagcag ctcagtgact gtaacctgca gccagtcc               600
atcacctgca atgtgcccca cccggcaagc agcaccaagg tggacaagaa aattgagccc   660
cggggaccca caatcaagcc ctgtcctcca tgcaaatgcc cagcacctaa cctcttgggt   720
ggaccatccg tcttcatctt ccctccaaag atcaaggatg tactcatgat ctccctgagc   780
cccatagtca catgtgtggt ggtggatgtg agcgaggatg acccagatca gtgtgtgtg   840
tggtttgtga acaacgtgga agtacacaca gctcagacac aaaccatag agaggattac   900
aacagtactc tccgggtggt cagtgccctc cccatccagc accaggactg gatgagtggc   960
aaggagttca atgcaaggt caacaacaaa gacctcccag cgcccatcga gaaaccatc   1020
tcaaaaccca aagggtcagt aagagctcca caggtatatg tcttgcctcc accagaagaa  1080
gagatgacta agaaacaggt cactctgacc tgcatggtca cagactcat gcctgaagac  1140
atttacgtgg agtggaccaa caacgggaaa acagagctaa actacaagaa cactgaacca  1200
gtcctggact ctgatggttc ttacttcatg tacagcaagc tgagtggaaa agaagaaga  1260
tgggtggaaa gaaatagcta ctcctgttca gtggtccacg agggtctgca caatcaccac  1320
acgactaaga gcttctcccg gactccgggt aaa                               1353

SEQ ID NO: 146          moltype = DNA   length = 642
FEATURE                 Location/Qualifiers
misc_feature            1..642
                        note = TF1413-03e005 L Chain Gene
source                  1..642
                        mol_type = other DNA
                        organism = synthetic construct
SEQUENCE: 146
gatgttgtga tgacccaaac tccatcctcc ttatctgcct ctctgggaga aagagtcagt    60
ctcacttgtc gggcaagtca ggaaattagt ggttacttaa gctggcttca gcagaaacca   120
```

```
gatggaacta ttaaacgcct gatctacgcc gcatccactt tagattctgg tgtcccaaaa    180
aggttcagtg gcagtaggtc tgggtcagat tattctctca ccatcagcag ccttgagtct    240
gaagattttg cagactatta ctgtctacaa tatgctagtt atccgctcac gttcggtgct    300
gggaccaagc tggagctgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

SEQ ID NO: 147          moltype = DNA   length = 357
FEATURE                 Location/Qualifiers
misc_feature            1..357
                        note = TF1413-03e015 H Chain V Region Gene
source                  1..357
                        mol_type = other DNA
                        organism = synthetic construct
SEQUENCE: 147
gaggtccagc tgcagcagtc tggacctgag ctggtgaagc ctggagcttc aatgaagata    60
tcctgcaagg cttctggtta ctcattcact ggctacacca tgaactgggt gaagcagagc    120
catggaaaga accttgagtg gattggactt attaatcctt acaatggtgg tactagctac    180
aaccagaagt tcaagggcaa ggccacatta actgtagaca agtcatccag cacagcctac    240
atggagctcc tcagtctgac atctgaggac tctgcagtct attactgcgc aagaggggat    300
tactacccc cctatgctat ggactactgg ggtcaaggaa cctcagtcac cgtctcg       357

SEQ ID NO: 148          moltype = DNA   length = 324
FEATURE                 Location/Qualifiers
misc_feature            1..324
                        note = TF1413-03e015 L Chain V Region Gene
source                  1..324
                        mol_type = other DNA
                        organism = synthetic construct
SEQUENCE: 148
gacattgtga tgtcacagtc tccaaaattc atgtccacat cagtaggaga cagggtcagc    60
gtcacctgca aggccagtca gaatgtgggt actaatgtag cctggtatca acagaaaccg    120
gggcaatctc ctaaaccact gatttattcg cgcgtcctacc ggtatagtgg agtccctgat    180
cgcttcacag gcagtggatc tgggacagat ttcactctca ccatcagcaa tgtgcagtct    240
gaagacttgg cagagtattt ctgtcagcaa tataacagat atcctctcac gttcggtgtt    300
gggaccaagc tggaaatcaa acgg                                           324

SEQ ID NO: 149          moltype = DNA   length = 1350
FEATURE                 Location/Qualifiers
misc_feature            1..1350
                        note = TF1413-03e015 H Chain Gene
source                  1..1350
                        mol_type = other DNA
                        organism = synthetic construct
SEQUENCE: 149
gaggtccagc tgcagcagtc tggacctgag ctggtgaagc ctggagcttc aatgaagata    60
tcctgcaagg cttctggtta ctcattcact ggctacacca tgaactgggt gaagcagagc    120
catggaaaga accttgagtg gattggactt attaatcctt acaatggtgg tactagctac    180
aaccagaagt tcaagggcaa ggccacatta actgtagaca agtcatccag cacagcctac    240
atggagctcc tcagtctgac atctgaggac tctgcagtct attactgcgc aagaggggat    300
tactacccc cctatgctat ggactactgg ggtcaaggaa cctcagtcac cgtctcgagc    360
gccaaaacaa cagccccatc ggtctatcca ctggccccta tgtgtggaga tacaactggc    420
tcctcggtga ctctaggatg cctggtcaag ggttatttcc ctgagccagt gaccttgacc    480
tggaactctg gatccctgtc cagtggtgtg cacaccttcc cagctgtcct gcagtctgac    540
ctctacaccc tcagcagctc agtgactgta acctcgagca cctggcccag ccagtccatc    600
acctgcaatg tggcccaccc ggcaagcagc accaaggtgg acaagaaaat tgagcccggg    660
ggacccacaa tcaagccctg tcctccatgc aaatgcccag cacctaacct cttgggtgga    720
ccatccgtct tcatcttccc tccaaagatc aaggatgtac tcatgatctc cctgagcccc    780
atagtcacat gtgtggtggt ggatgtgagc gaggatgacc cagatgtcca gatcagctgg    840
tttgtgaaca acgtggaagt acacacagct cagacacaaa cccatagaga ggattacaac    900
agtactctcc gggtggtcag tgccctcccc atccagcacc aggactggat gagtggcaag    960
gagttcaaat gcaaggtcaa caacaaagac ctcccagcgc ccatcgagag aaccatctca    1020
aaacccaaag ggtcagtaag agctccacag gtatatgtct tgcctccacc agaagaagag    1080
atgactaaga acaggtcac tctgacctgc atggtcacag acttcatgcc tgaagacatt    1140
tacgtggagt ggaccaacaa cgggaaaaca gagctaaact acaagaacac tgaaccagtc    1200
ctggactctg atggttctta cttcatgtac agcaagctga gagtggaaaa gaagaactgg    1260
gtggaaagaa atagctactc ctgttcagtg gtccacgagg gtctgcacaa tcaccacacg    1320
actaagagct ctcccggac tccgggtaaa                                      1350

SEQ ID NO: 150          moltype = DNA   length = 642
FEATURE                 Location/Qualifiers
misc_feature            1..642
                        note = TF1413-03e015 L Chain Gene
source                  1..642
                        mol_type = other DNA
                        organism = synthetic construct
```

```
SEQUENCE: 150
gacattgtga tgtcacagtc tccaaaattc atgtccacat cagtaggaga cagggtcagc    60
gtcacctgca aggccagtca gaatgtgggt actaatgtag cctggtatca acagaaaccg   120
gggcaatctc ctaaaccact gatttattcg gcgtcctacc ggtatagtgg agtccctgat   180
cgcttcacag gcagtggatc tgggacagat ttcactctca ccatcagcaa tgtgcagtct   240
gaagacttgg cagagtattt ctgtcagcaa tataacagat atcctctcac gttcggtgtt   300
gggaccaagc tggaaatcaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctataccctgtgaggccac tcacaagaca  600
tcaacttcac ccattgtcaa gagcttcaac aggaatgagt gt                      642

SEQ ID NO: 151          moltype = DNA  length = 354
FEATURE                 Location/Qualifiers
misc_feature            1..354
                        note = TF1413-03e034 H Chain V Region Gene
source                  1..354
                        mol_type = other DNA
                        organism = synthetic construct
SEQUENCE: 151
gaggtccagc tgcagcagtc tggacctgag ctggagaagc ctggcgcttc agtgaagata    60
tcctgcaagg cttctggtta ctcattcact ggctacaaca tgaactgggt gaagcagagc   120
aatggaaaga gccttgagtg gattggaaat attgatcctt actatggtgg tactagctac   180
aaccagaagt tcaagggcaa ggccacattg actgtagaca atcctccag cacagcctac    240
atgcagctca gagcctgac atctgaggac tctgcagtct attactgtgc aagagggaac    300
tacgggtact atgctatgga ctactgggt caaggaacct cagtcaccgt ctcg           354

SEQ ID NO: 152          moltype = DNA  length = 324
FEATURE                 Location/Qualifiers
misc_feature            1..324
                        note = TF1413-03e034 L Chain V Region Gene
source                  1..324
                        mol_type = other DNA
                        organism = synthetic construct
SEQUENCE: 152
gacattgtga tgtcacagtc tccaaaattc atgtccacat cagtaggaga cagggtcagc    60
atcacctgca aggccagtca gaatgttcgt actgctgtag cctggtatca acagaaacca   120
gggcaatctc ctaaagcact gatttacttg gcatccaagc ggcacactgg agtccctgat   180
cgcttcacag gcagtggatc tgggacagat ttcactctca ccattagcaa tgtgcaatct   240
gaagacctgg cagattattt ctgtctgcaa cattggaatt atccgctcac gttcggtgct   300
gggaccaagc tggagctgaa acgg                                           324

SEQ ID NO: 153          moltype = DNA  length = 1347
FEATURE                 Location/Qualifiers
misc_feature            1..1347
                        note = TF1413-03e034 H Chain Gene
source                  1..1347
                        mol_type = other DNA
                        organism = synthetic construct
SEQUENCE: 153
gaggtccagc tgcagcagtc tggacctgag ctggagaagc ctggcgcttc agtgaagata    60
tcctgcaagg cttctggtta ctcattcact ggctacaaca tgaactgggt gaagcagagc   120
aatggaaaga gccttgagtg gattggaaat attgatcctt actatggtgg tactagctac   180
aaccagaagt tcaagggcaa ggccacattg actgtagaca atcctccag cacagcctac    240
atgcagctca gagcctgac atctgaggac tctgcagtct attactgtgc aagagggaac    300
tacgggtact atgctatgga ctactgggt caaggaacct cagtcaccgt ctcgagcgcc    360
aaaacaacag ccccatcggt ctatccactg gcccctgtgt gtggagatac aactggctcc   420
tcggtgactc taggatgcct ggtcaagggt tatttccctg agccagtgac cttgacctgg   480
aactctggat ccctgtccag tggtgtgcac accttcccag ctgtcctgca gtctgacctc   540
tacaccctca gcagctcagt gactgtaacc tcgagcacct ggcccagcca gtccatcacc   600
tgcaatgtgg cccaccggc aagcagcacc aaggtggaca gaaaattga gccccgggga    660
cccacaatca agccctgtcc tccatgcaaa tgcccagcac ctaacctctt gggtggacca   720
tccgtcttca tcttccctcc aaagatcaag gatgtactca tgatctccct gagcccatta   780
gtcacatgtg tggtggtgga tgtgagcgag gatgaccag atgtccagat cagctggttt   840
gtgaacaacg tggaagtaca cacagctcag acacaaaccc atagagagga ttacaacagt   900
actctccggg tggtcagtgc cctccccatc agcaccagg actggatgag tggcaaggag   960
ttcaaatgca aggtcaacaa caaagacctc ccagcgccca tcgagagaac catctcaaaa   1020
cccaaagggt cagtaagagc tccacaggta tatgtcttgc ctccaccaga agaagagatg   1080
actaagaaac aggtcactct gacctgcatg gtcacagact tcatgcctga agacatttac   1140
gtggagtgga ccaacaacgg gaaaacagag ctaaactaca agaacactga accagtcctg   1200
gactctgatg gttcttactt catgtacagc aagctgagag tggaaagaa gaactgggtg    1260
gaaagaaata gctactcctg ttcagtggtc acgaggggtc tgcacaatca ccacgcgact   1320
aagagcttct cccggactcc gggtaaa                                       1347

SEQ ID NO: 154          moltype = DNA  length = 642
FEATURE                 Location/Qualifiers
misc_feature            1..642
                        note = TF1413-03e034 L Chain Gene
```

```
source                  1..642
                        mol_type = other DNA
                        organism = synthetic construct
SEQUENCE: 154
gacattgtga tgtcacagtc tccaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atccgctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cacccctcacg  540
ttgaccaagg acgagtatga acgacataac agctatacct gtgaggccac tcacaagaca   600
tcaacttcac ccattgtcaa gagcttcaac aggaatgagt gt                      642

SEQ ID NO: 155          moltype = AA   length = 440
FEATURE                 Location/Qualifiers
REGION                  1..440
                        note = MISC_FEATURE - Human GPC3 N Terminal Fragment
source                  1..440
                        mol_type = protein
                        organism = Homo sapiens
SEQUENCE: 155
DATCHQVRSF FQRLQPGLKW VPETPVPGSD LQVCLPKGPT CCSRKMEEKY QLTARLNMEQ    60
LLQSASMELK FLIIQNAAVF QEAFEIVVRH AKNYTNAMFK NNYPSLTPQA FEFVGEFFTD   120
VSLYILGSDI NVDDMVNELF DSLFPVIYTL MNPGLPDSA LDINECLRGA RRDLKVFGNF    180
PKLIMTQVSK SLQVTRIFLQ ALNLGIEVIN TTDHLKFSKD CGRMLTRMWY CSYCQGLMMV   240
KPCGGYCNVV MQGCMAGVVE IDKYWREYIL SLEELVNGMY RIYDMENVLL GLFSTIHDSI   300
QYVQKNAGKL TTTIGKLCAH SQQRQYRSAY YPEDLFIDKK VLKVAHVEHE ETLSSRRREL   360
IQKLKSFISF YSALPGYICS HSPVAENDTL CWNGQELVER YSQKAARNGM KNQFNLHELK   420
MKGPEPVVSQ IIDKLKHINQ                                               440

SEQ ID NO: 156          moltype = AA   length = 109
FEATURE                 Location/Qualifiers
REGION                  1..109
                        note = MISC_FEATURE - Human GPC3 C Terminal Fragment
source                  1..109
                        mol_type = protein
                        organism = Homo sapiens
SEQUENCE: 156
LLRTMSMPKG RVLDKNLDEE GFESGDCGDD EDECIGGSGD GMIKVKNQLR FLAELAYDLD    60
VDDAPGNSQQ ATPKDNEIST FHNLGNVHSP LKLLTSMAIS VVCFFFLVH               109

SEQ ID NO: 157          moltype = AA   length = 580
FEATURE                 Location/Qualifiers
REGION                  1..580
                        note = MISC_FEATURE - Human GPC3
source                  1..580
                        mol_type = protein
                        organism = Homo sapiens
SEQUENCE: 157
MAGTVRTACL VVAMLLSLDF PGQAQPPPPP PDATCHQVRS FFQRLQPGLK WVPETPVPGS    60
DLQVCLPKGP TCCSRKMEEK YQLTARLNME QLLQSASMEL KFLIIQNAAV FQEAFEIVVR   120
HAKNYTNAMF KNNYPSLTPQ AFEFVGEFFT DVSLYILGSD INVDDMVNEL FDSLFPVIYT   180
QLMNPGLPDS ALDINECLRG ARRDLKVFGN FPKLIMTQVS KSLQVTRIFL QALNLGIEVI   240
NTTDHLKFSK DCGRMLTRMW YCSYCQGLMM VKPCGGYCNV VMQGCMAGVV EIDKYWREYI   300
LSLEELVNGM YRIYDMENVL LGLFSTIHDS IQYVQKNAGK LTTTIGKLCA HSQQRQYRSA   360
YYPEDLFIDK KVLKVAHVEH EETLSSRRRE LIQKLKSFIS FYSALPGYIC SHSPVAENDT   420
LCWNGQELVE RYSQKAARNG MKNQFNLHEL KMKGPEPVVS QIIDKLKHIN QLLRTMSMPK   480
GRVLDKNLDE EGFESGDCGD DEDECIGGSG DGMIKVKNQL RFLAELAYDL DVDDAPGNSQ   540
QATPKDNEIS TFHNLGNVHS PLKLLTSMAI SVVCFFFLVH                         580

SEQ ID NO: 158          moltype = DNA   length = 1320
FEATURE                 Location/Qualifiers
misc_feature            1..1320
                        note = Human GPC3 N Terminal Fragment Gene
source                  1..1320
                        mol_type = unassigned DNA
                        organism = Homo sapiens
SEQUENCE: 158
gacgccacct gtcaccaagt ccgctccttc ttccagagac tgcagcccgg actcaagtgg    60
gtgccagaaa ctcccgtgcc aggatcagat ttgcaagtat gtctccctaa gggcccaaca   120
tgctgtcaa gaaagatgga agaaaaatac caactagctga cacgattgaa catgaacag   180
ctgcttcagt ctgcaagtat ggagctcaag ttcttaatta ttcagaatgc tgcggttttc   240
caagaggcct ttgaaattgt tgttcgccat gccaagaact acaccaatgc catgttcaag   300
aacaactacc caagcctgac tccacaagct tttgagtttg tggtgaatt tttcacagat   360
gtgtctctct acatcttggg ttctgacatc aatgtagat acatggtcaa tgaattgttt   420
gacagcctgt ttcagtcat ctatacccag ctaatgaacc caggcctgcc tgattcagcc   480
```

```
ttggacatca atgagtgcct ccgaggagca agacgtgacc tgaaagtatt tgggaatttc    540
cccaagctta ttatgaccca ggtttccaag tcactgcaag tcactaggat cttccttcag    600
gctctgaatc ttggaattga agtgatcaac acaactgatc acctgaagtt cagtaaggac    660
tgtggccgaa tgctcaccag aatgtggtac tgctcttact gccagggact gatgatggtt    720
aaaccctgtg gcggttactg caatgtggtc atgcaaggct gtatggcagg tgtggtggag    780
attgacaagt actggagaga atacattctg tcccttgaag aacttgtgaa tggcatgtac    840
agaatctatg acatggagaa cgtactgctt ggtctctttt caacaatcca tgattctatc    900
cagtatgtcc agaagaatgc aggaaagctg accaccacta ttggcaagtt atgtgcccat    960
tctcaacaac gccaatatag atctgcttat tatcctgaag atctcttttat tgacaagaaa   1020
gtattaaaag ttgctcatgt agaacatgaa gaaaccttat ccagccgaag aagggaacta   1080
attcagaagt tgaagtcttt catcagcttc tatagtgctt tgcctggcta catctgcagc   1140
catagccctg tggcggaaaa cgacacccct tgctggaatg acaagaact cgtggagaga   1200
tacagccaaa aggcagcaag gaatggaatg aaaaaccagt tcaatctcca tgagctgaaa   1260
atgaagggcc tgagccagt ggtcagtcaa attattgaca aactgaagca cattaaccag   1320

SEQ ID NO: 159          moltype = DNA   length = 327
FEATURE                 Location/Qualifiers
misc_feature            1..327
                        note = Human GPC3 C Terminal Fragment Gene
source                  1..327
                        mol_type = unassigned DNA
                        organism = Homo sapiens
SEQUENCE: 159
ctcctgagaa ccatgtctat gcccaaaggt agagttctgg ataaaaacct ggatgaggaa     60
gggtttgaaa gtgagactg cggtgatgat gaagatgagt gcattggagg ctctggtgat    120
ggaatgataa aagtgaagaa tcagctccgc ttccttggaa aactggccta tgatctggat    180
gtggatgatg cgcctggaaa cagtcagcag gcaactccga aggacaacga gataagcacc    240
tttcacaacc tcgggaacgt tcattccccg ctgaagcttc tcaccagcat ggccatctcg    300
gtggtgtgct tcttcttcct ggtgcac                                         327

SEQ ID NO: 160          moltype = DNA   length = 1743
FEATURE                 Location/Qualifiers
source                  1..1743
                        mol_type = unassigned DNA
                        organism = Homo sapiens
SEQUENCE: 160
atggccggga ccgtgcgcac cgcgtgcttg gtggtggcga tgctgctcag cttggacttc     60
ccgggacagg cgcagccccc gccgccgccg cggacgccca cctgtcacca gtccgctcc    120
ttcttccaga gactgcagcc cggactcaag tgggtgccaa aaactcccgt gccaggatca    180
gatttgcaag tatgtctccc taagggccca acatgctgct caagaaagat ggaagaaaaa    240
taccaactaa cagcacgatt gaacatggaa cagctgcttc agtctgcaag tatggagctc    300
aagttcttaa ttattcagaa tgctgcggtt ttccaagagg cctttgaaat tgttgttcgc    360
catgccaaga actacaccaa tgccatgttc aagaacaact acccaagcct gactccacaa    420
gcttttgagt ttgtgggtga attttcaca gatgtgtctc tctacatctt gggttctgac    480
atcaatgtag atgacatggt caatgaattg tttgacagcc tgtttccagt catctatacc    540
cagctaatga acccaggcct gcctgattca gccttgaca tcaatgagtg cctccgagga    600
gcaagacgtg acctgaaagt atttgggaat ttccccagac ttattatgac ccaggtttcc    660
aagtcactgc aagtcactag gatcttcctt caggctctga atcttggaat tgaagtgatc    720
aacacaactg atcacctgaa gttcagtaag gactgtggcc gaatgctcac cagaatgtgg    780
tactgctctt actgccaggg actgatgatg gttaaaccct gtggcggtta ctgcaatgtg    840
gtcatgcaag gctgtatggc aggtgtggtg gagattgaca gtactggag agaatacatt    900
ctgtcccttg aagaacttgt gaatggcatg tacagaatct atgacatgga gaacgtactg    960
cttggtctct tttcaacaat ccatgattct atccagtatg tccagaagaa tgcaggaaag   1020
ctgaccacca ctattggcaa gttatgtgcc cattctcaac aacgccaata tagatctgct   1080
tattatcctg aagatctctt tattgacaag aaagtattaa aagttgctca tgtagaacat   1140
gaagaaaccct tatccagccg aagaagggaa ctaattcaga agttgaagtc tttcatcagc   1200
ttctatagtg ctttgcctgg ctacatctgc agccatagcc ctgtggcgga aaacgacacc   1260
cttgctggaa tggacaagaa actcgtggag agatacagcc aaaaggcagc aaggaatgga   1320
atgaaaaaacc agttcaatct ccatgagctg aaaatgaagg ggcctgagcc agtggtcagt   1380
caaattattg acaaactgaa gcacattaac cagctcctga gaaccatgtc tatgcccaaa   1440
ggtagagttc tggataaaaa cctggatgag gaagggtttg aaagtggaga ctgcggtgat   1500
gatgaagatg agtgcattgg aggctctggt gatggaatga taaaagtgaa gaatcagctc   1560
cgcttccttg gaaaactggc ctatgatctg gatgtggatg atgcgcctgg aaacagtcag   1620
caggcaactc cgaaggacaa cgagataagc acctttcaca acctcgggaa cgttcattcc   1680
ccgctgaagc ttctcaccag catggccatc tcggtggtgt gcttcttctt cctggtgcac   1740
tga                                                                 1743

SEQ ID NO: 161          moltype = DNA   length = 33
FEATURE                 Location/Qualifiers
misc_feature            1..33
                        note = F-1 Primer
source                  1..33
                        mol_type = other DNA
                        organism = synthetic construct
SEQUENCE: 161
tcccccgggg gacgccacct gtcaccaagt ccg                                  33

SEQ ID NO: 162          moltype = DNA   length = 33
FEATURE                 Location/Qualifiers
```

```
misc_feature            1..33
                        note = R-7 Primer
source                  1..33
                        mol_type = other DNA
                        organism = synthetic construct
SEQUENCE: 162
tccccgcggc tggttaatgt gcttcagttt gtc                                 33

SEQ ID NO: 163          moltype = DNA  length = 28
FEATURE                 Location/Qualifiers
misc_feature            1..28
                        note = F-8 Primer
source                  1..28
                        mol_type = other DNA
                        organism = synthetic construct
SEQUENCE: 163
tcccccggg ctcctgagaa ccatgtct                                        28

SEQ ID NO: 164          moltype = DNA  length = 33
FEATURE                 Location/Qualifiers
misc_feature            1..33
                        note = R-9 Primer
source                  1..33
                        mol_type = other DNA
                        organism = synthetic construct
SEQUENCE: 164
tcccgcggg tgcaccagga agaagaagca cac                                  33

SEQ ID NO: 165          moltype = AA  length = 241
FEATURE                 Location/Qualifiers
REGION                  1..241
                        note = TF1413-02d028 scFv
source                  1..241
                        mol_type = protein
                        organism = synthetic construct
SEQUENCE: 165
QVQLKESGPE LEKPGASVKI SCKASGYSFT GYNMNWVKQS NGKSLEWIGN IDPYYGGTSY    60
NQKFKGKATL TVDKSSSTAY MQLKSLTSED SAVYYCARGD YRAYYFDYWG QGTTLTVSGG   120
GGSGGGGSGG GGSDIQMTQS PKFMSTSVGD RVSITCKASQ NVRTAVAWYQ QKPGQSPKAL   180
IYLASNRHTG VPDRFTGSGS GTDFTLTISN VQSEDLADYF CLQHWNYPLT FGAGTKLELK   240
R                                                                  241

SEQ ID NO: 166          moltype = AA  length = 245
FEATURE                 Location/Qualifiers
REGION                  1..245
                        note = TF1413-02d039 scFv
source                  1..245
                        mol_type = protein
                        organism = synthetic construct
SEQUENCE: 166
EVKLVESGGG LVKPGGSLKL SCAASGFAFS SYDMSWVRQT PEKRLEWVAY ISSGGGSTYY    60
PDTVKGRFTI SRDNAKNTLY LQMSSLKSED TAMYYCARRG LRRAMDYWGQ GTSVTVSGGG   120
GSGGGGSGGG GSDVVMTQTP LSLPVSLGDQ ASISCRSSQS LVHSNGNTYL HWYLQKPGQS   180
PKLLIYKVSN RFSGVPDRFS GSGSGTDFTL KISRVEAEDL GVYFCSQSTH VPLTFGAGTK   240
LELKR                                                              245

SEQ ID NO: 167          moltype = AA  length = 237
FEATURE                 Location/Qualifiers
REGION                  1..237
                        note = TF1413-02e004 scFv
source                  1..237
                        mol_type = protein
                        organism = synthetic construct
SEQUENCE: 167
QVQLQQSGAE LVKPGAPVKL SCKASGYTFT SYWMNWVKQR PGRGLEWIGR IDPSDSETHY    60
NQKFKDEATL TVDKSSSTAY IQLSSLTSED SAVYYCARGY YAMDYWGQGT SVTVSGGGS    120
GGGGSGGGGS DIVLTQSPKF MSTSVGDRVS ITCKASQDVS TAVAWYQQKP GQSPKLLIYS   180
ASYRYTGVPD RFTGSGSGTD FTFTISSVQA EDLAVYYCQQ HYSTPTFGGG TKLEIKR      237

SEQ ID NO: 168          moltype = AA  length = 243
FEATURE                 Location/Qualifiers
REGION                  1..243
                        note = TF1413-02e014 scFv
source                  1..243
                        mol_type = protein
                        organism = synthetic construct
SEQUENCE: 168
QVQLKQSGAE LVRSGASVKL SCTASGFNIK DYYMHWVKQR PEQGLEWIGW IDPENGDTEY    60
APKFQGKATM TADTSSNTAY LQLSSLTSED TAVYYCNAGY YDYDGYAMDY WGQGTSVTVS   120
```

```
                    GGGGSGGGGS GGGGSDIVLT QSPKFMSTSV GDRVSITCKA SQDVGTAVAW YQQKPGQSPK   180
                    LLIYWASTRH TGVPDRFTGS GSGTDFTLTI SNVQSEDLAD YFCQQYSSYP LTFGGGTKLE   240
                    IKR                                                                243

SEQ ID NO: 169      moltype = AA  length = 246
FEATURE             Location/Qualifiers
REGION              1..246
                    note = TF1413-02e030 scFv
source              1..246
                    mol_type = protein
                    organism = synthetic construct
SEQUENCE: 169
EVQLQQSGAE LVRPGALVKL SCKASGFNIK DYYMHWVKQR PEQGLEWIGW IDPENGNTIY   60
DPKFQGKASI TADTSSNTAY LQLSSLTSED TAVYYCAIST MITTLDYWGQ GTTLTVSGGG   120
GSGGGGSGGG GSDIQMTQSP SSLAMSVGQK VTMSCKSSQS LLNSSNQKNY LAWYQQKPGQ   180
SPKLLVYFAS TRESGVPDRF IGSGSGTDFT LTISSVQAED LADYFCQQHY STPLTFGAGT   240
KLELKR                                                             246

SEQ ID NO: 170      moltype = AA  length = 239
FEATURE             Location/Qualifiers
REGION              1..239
                    note = TF1413-02e040 scFv
source              1..239
                    mol_type = protein
                    organism = synthetic construct
SEQUENCE: 170
EVMLVESGPE LVKPGASMKI SCKASGYSFT GYTMNWVKQS HGKNLEWIGL INPYNGGTSY   60
NQNFKGKATL TVDKSSSTAY MELLSLTSED SAVYYCARGY YGRFDYWGQG TTLTVSGGGG   120
SGGGGSGGGG SDILLTQSPK FMSTSVGDRV SITCKASQNV RTAVAWYQQK PGQSPKALIY   180
LASNRHTGVP DRFTGSGSGT DFTLTISNVQ SEDLADYFCL QHWNYPLTFG AGTKLELKR   239

SEQ ID NO: 171      moltype = AA  length = 238
FEATURE             Location/Qualifiers
REGION              1..238
                    note = TF1413-03e001 scFv
source              1..238
                    mol_type = protein
                    organism = synthetic construct
SEQUENCE: 171
QVQLKQSGPE LVKPGASVKI SCKASGYSFT GYYMHWVKQS HVKSLEWIGR INPYNGATSY   60
NQNFKDKASL TVDKSSSTAY MELHSLTSED SAVYYCARNY GYFDYWGQGT TLTVSGGGGS   120
GGGGSGGGGS DIKMTQSPKF MSTSVGDRVS VTCEASQNVD NNVVWYQQKP GQSPKALIYS   180
ASYRYSGVPD RFTGSGSGTD FTLTISNVQS EDLAEYFCQQ YNSYPLTFGA GTKLEIKR    238

SEQ ID NO: 172      moltype = AA  length = 238
FEATURE             Location/Qualifiers
REGION              1..238
                    note = TF1413-03e004 scFv
source              1..238
                    mol_type = protein
                    organism = synthetic construct
SEQUENCE: 172
QVQLKQSGAE LVKPGAPVKL SCKASGYTFT SYWMNWVKQR PGRGLEWIGR IDPSDSETHY   60
NQKFKDKATL TVDKSSSTAY IQLSSLTSED SAVYYCARGY YGSNYWGQGT TLTVSGGGGS   120
GGGGSGGGGS DIKMTQSPKF MSTSVGDRVS VTCKASQNVG TNVAWYQQKP GQSPKALIYS   180
ASYRYSGVPD RFTGSGSGTD FTLTISNVQS EDLAEYFCQQ YNSYPLTFGA GTKLELKR    238

SEQ ID NO: 173      moltype = AA  length = 243
FEATURE             Location/Qualifiers
REGION              1..243
                    note = TF1413-03e005 scFv
source              1..243
                    mol_type = protein
                    organism = synthetic construct
SEQUENCE: 173
QVQLKESGAE LVRSGASVKL SCTASGFNIK DYYMHWVKQR PEQGLEWIGW IDPENGDTEY   60
APKFQGKATM TADTSSNTAY LQLSSLTSED TAVYYCNAFY YDYDGYAMDY WGQGTSVTVS   120
GGGGSGGGGS GGGGSDVVMT QTPSSLSASL GERVSLTCRA SQEISGYLSW LQQKPDGTIK   180
RLIYAASTLD SGVPKRFSGS RSGSDYSLTI SSLESEDFAD YYCLQYASYP LTFGAGTKLE   240
LKR                                                                243

SEQ ID NO: 174      moltype = AA  length = 242
FEATURE             Location/Qualifiers
REGION              1..242
                    note = TF1413-03e015 scFv
source              1..242
                    mol_type = protein
                    organism = synthetic construct
SEQUENCE: 174
```

```
EVQLQQSGPE LVKPGASMKI SCKASGYSFT GYTMNWVKQS HGKNLEWIGL INPYNGGTSY    60
NQKFKGKATL TVDKSSSTAY MELLSLTSED SAVYYCARGD YYPPYAMDYW GQGTSVTVSG   120
GGGSGGGGSG GGGSDIVMSQ SPKFMSTSVG DRVSVTCKAS QNVGTNVAWY QQKPGQSPKP   180
LIYSASYRYS GVPDRFTGSG SGTDFTLTIS NVQSEDLAEY FCQQYNRYPL TFGVGTKLEI   240
KR                                                                  242

SEQ ID NO: 175          moltype = AA  length = 241
FEATURE                 Location/Qualifiers
REGION                  1..241
                        note = TF1413-03e034 scFv
source                  1..241
                        mol_type = protein
                        organism = synthetic construct
SEQUENCE: 175
EVQLQQSGPE LEKPGASVKI SCKASGYSFT GYNMNWVKQS NGKSLEWIGN IDPYYGGTSY    60
NQKFKGKATL TVDKSSSTAY MQLKSLTSED SAVYYCARGN YGYYAMDYWG QGTSVTVSGG   120
GGSGGGGSGG GGSDIVMSQS PKFMSTSVGD RVSITCKASQ NVRTAVAWYQ QKPGQSPKAL   180
IYLASNRHTG VPDRFTGSGS GTDFTLTISN VQSEDLADYF CLQHWNYPLT FGAGTKLELK   240
R                                                                   241

SEQ ID NO: 176          moltype = DNA  length = 20
FEATURE                 Location/Qualifiers
misc_feature            1..20
                        note = T7 primer
source                  1..20
                        mol_type = other DNA
                        organism = synthetic construct
SEQUENCE: 176
taatacgact cactataggg                                                20

SEQ ID NO: 177          moltype = DNA  length = 21
FEATURE                 Location/Qualifiers
misc_feature            1..21
                        note = cp3R primer
source                  1..21
                        mol_type = other DNA
                        organism = synthetic construct
SEQUENCE: 177
gccagcattg acaggaggtt g                                              21

SEQ ID NO: 178          moltype = AA  length = 241
FEATURE                 Location/Qualifiers
REGION                  1..241
                        note = #5 VH1-15-VL1
source                  1..241
                        mol_type = protein
                        organism = synthetic construct
SEQUENCE: 178
QVQLVQSGAE VKKPGASVKV SCKASGYSFT GYNMNWVRQA PGQGLEWIGN IDPYYGGTSY    60
NQKFKGRATL TVDTSTSTAY MELRSLRSDD TAVYYCARGD YRAYYFDYWG QGTTVTVSSG   120
GGGSGGGGSG GGSDIQMTQ SPSSLSASVG DRVTITCKAS QNVRTAVAWY QQKPGKAPKA   180
LIYLASNRHT GVPSRFSGSG SGTDFTLTIS SLQPEDFATY YCLQHWNYPL TFGGGTKVEI   240
K                                                                   241

SEQ ID NO: 179          moltype = AA  length = 241
FEATURE                 Location/Qualifiers
REGION                  1..241
                        note = #5 VH2-15-VL1
source                  1..241
                        mol_type = protein
                        organism = synthetic construct
SEQUENCE: 179
QVQLVQSGAE VKKPGASVKV SCKASGYSFT GYNMNWVRQA PGQGLEWIGN IDPYYGGTSY    60
NQKFKGRVTL TVDTSTSTAY MELRSLRSDD TAVYYCARGD YRAYYFDYWG QGTTVTVSSG   120
GGGSGGGGSG GGSDIQMTQ SPSSLSASVG DRVTITCKAS QNVRTAVAWY QQKPGKAPKA   180
LIYLASNRHT GVPSRFSGSG SGTDFTLTIS SLQPEDFATY YCLQHWNYPL TFGGGTKVEI   240
K                                                                   241

SEQ ID NO: 180          moltype = AA  length = 241
FEATURE                 Location/Qualifiers
REGION                  1..241
                        note = #5 VH3-15-VL1
source                  1..241
                        mol_type = protein
                        organism = synthetic construct
SEQUENCE: 180
QVQLVQSGAE VKKPGASVKV SCKASGYTFT GYNMNWVRQA PGQGLEWIGN IDPYYGGTSY    60
NQKFKGRVTL TVDTSTSTAY MELRSLRSDD TAVYYCARGD YRAYYFDYWG QGTTVTVSSG   120
GGGSGGGGSG GGSDIQMTQ SPSSLSASVG DRVTITCKAS QNVRTAVAWY QQKPGKAPKA   180
```

```
LIYLASNRHT GVPSRFSGSG SGTDFTLTIS SLQPEDFATY YCLQHWNYPL TFGGGTKVEI    240
K                                                                  241

SEQ ID NO: 181          moltype = AA  length = 245
FEATURE                 Location/Qualifiers
REGION                  1..245
                        note = #6 VH1-15-VL1
source                  1..245
                        mol_type = protein
                        organism = synthetic construct
SEQUENCE: 181
EVQLVESGGG LVQPGGSLRL SCAASGFAFS SYDMSWVRQA PGKGLEWVAY ISSGGGSTYY    60
PDTVKGRFTI SRDNAKNSLY LQMNSLRAED TAVYYCARRG LRRAMDYWGQ GTMVTVSSGG    120
GGSGGGGSGG GGSDIVMTQS PLSLPVTPGE PASISCRSSQ SLVHSNGNTY LHWYLQKPGQ    180
SPQLLIYKVS NRFSGVPDRF SGSGSGTDFT LKISRVEAED VGVYYCSQST HVPLTFGGGT    240
KVEIK                                                              245

SEQ ID NO: 182          moltype = AA  length = 245
FEATURE                 Location/Qualifiers
REGION                  1..245
                        note = #6 VH1-15-VL2
source                  1..245
                        mol_type = protein
                        organism = synthetic construct
SEQUENCE: 182
EVQLVESGGG LVQPGGSLRL SCAASGFAFS SYDMSWVRQA PGKGLEWVAY ISSGGGSTYY    60
PDTVKGRFTI SRDNAKNSLY LQMNSLRAED TAVYYCARRG LRRAMDYWGQ GTMVTVSSGG    120
GGSGGGGSGG GGSDIVMTQS PLSLPVTPGE PASISCRSSQ SLVHSSGNTY LHWYLQKPGQ    180
SPQLLIYKVS NRFSGVPDRF SGSGSGTDFT LKISRVEAED VGVYYCSQST HVPLTFGGGT    240
KVEIK                                                              245

SEQ ID NO: 183          moltype = AA  length = 245
FEATURE                 Location/Qualifiers
REGION                  1..245
                        note = #6 VH2-15-VL1
source                  1..245
                        mol_type = protein
                        organism = synthetic construct
SEQUENCE: 183
EVQLVESGGG LVQPGGSLRL SCAASGFAFS SYDMSWVRQA PGKRLEWVAY ISSGGGSTYY    60
PDTVKGRFTI SRDNAKNSLY LQMNSLRAED TAVYYCARRG LRRAMDYWGQ GTMVTVSSGG    120
GGSGGGGSGG GGSDIVMTQS PLSLPVTPGE PASISCRSSQ SLVHSNGNTY LHWYLQKPGQ    180
SPQLLIYKVS NRFSGVPDRF SGSGSGTDFT LKISRVEAED VGVYYCSQST HVPLTFGGGT    240
KVEIK                                                              245

SEQ ID NO: 184          moltype = AA  length = 245
FEATURE                 Location/Qualifiers
REGION                  1..245
                        note = #6 VH2-15-VL2
source                  1..245
                        mol_type = protein
                        organism = synthetic construct
SEQUENCE: 184
EVQLVESGGG LVQPGGSLRL SCAASGFAFS SYDMSWVRQA PGKRLEWVAY ISSGGGSTYY    60
PDTVKGRFTI SRDNAKNSLY LQMNSLRAED TAVYYCARRG LRRAMDYWGQ GTMVTVSSGG    120
GGSGGGGSGG GGSDIVMTQS PLSLPVTPGE PASISCRSSQ SLVHSSGNTY LHWYLQKPGQ    180
SPQLLIYKVS NRFSGVPDRF SGSGSGTDFT LKISRVEAED VGVYYCSQST HVPLTFGGGT    240
KVEIK                                                              245

SEQ ID NO: 185          moltype = AA  length = 283
FEATURE                 Location/Qualifiers
REGION                  1..283
                        note = hCD8-hCD28-h4-1BB-hCD3
source                  1..283
                        mol_type = protein
                        organism = synthetic construct
SEQUENCE: 185
FVPVFLPAKP TTTPAPRPPT PAPTIASQPL SLRPEACRPA AGGAVHTRGL DFACDIYIWA    60
PLAGTCGVLL LSLVITLYCN HRNRSKRSRL LHSDYMNMTP RRPGPTRKHY QPYAPPRDFA    120
AYRSRFSVVK RGRKKLLYIF KQPFMRPVQT TQEEDGCSCR FPEEEEGGCE LRVKFSRSAD    180
APAYQQGQNQ LYNELNLGRR EEYDVLDKRR GRDPEMGGKP RRKNPQEGLY NELQKDKMAE    240
AYSEIGMKGE RRRGKGHDGL YQGLSTATKD TYDALHMQAL PPR                    283

SEQ ID NO: 186          moltype = AA  length = 277
FEATURE                 Location/Qualifiers
REGION                  1..277
                        note = hCD8-hCD28-h4-1BB-hCD3
source                  1..277
                        mol_type = protein
```

```
                           organism = synthetic construct
SEQUENCE: 186
FVPVFLPAKP TTTPAPRPPT PAPTIASQPL SLRPEACRPA AGGAVHTRGL DFACDIYIWA   60
PLAGTCGVLL LSLVITLRSK RSRLLHSDYM NMTPRRPGPT RKHYQPYAPP RDFAAYRSRF  120
SVVKRGRKKL LYIFKQPFMR PVQTTQEEDG CSCRFPEEEE GGCELRVKFS RSADAPAYQQ  180
GQNQLYNELN LGRREEYDVL DKRRGRDPEM GGKPRRKNPQ EGLYNELQKD KMAEAYSEIG  240
MKGERRRGKG HDGLYQGLST ATKDTYDALH MQALPPR                          277

SEQ ID NO: 187             moltype = AA  length = 276
FEATURE                    Location/Qualifiers
REGION                     1..276
                           note = hCD8-hCD28-h4-1BB-hCD3
source                     1..276
                           mol_type = protein
                           organism = synthetic construct
SEQUENCE: 187
FVPVFLPAKP TTTPAPRPPT PAPTIASQPL SLRPEACRPA AGGAVHTRGL DFACDIYIWA   60
PLAGTCGVLL LSLVITRSKR SRLLHSDYMN MTPRRPGPTR KHYQPYAPPR DFAAYRSRFS  120
VVKRGRKKLL YIFKQPFMRP VQTTQEEDGC SCRFPEEEEG GCELRVKFSR SADAPAYQQG  180
QNQLYNELNL GRREEYDVLD KRRGRDPEMG GKPRRKNPQE GLYNELQKDK MAEAYSEIGM  240
KGERRRGKGH DGLYQGLSTA TKDTYDALHM QALPPR                           276

SEQ ID NO: 188             moltype = AA  length = 19
FEATURE                    Location/Qualifiers
source                     1..19
                           mol_type = protein
                           organism = Homo sapiens
SEQUENCE: 188
MDWTWRILFL VAAATGAHS                                               19

SEQ ID NO: 189             moltype = AA  length = 15
FEATURE                    Location/Qualifiers
source                     1..15
                           mol_type = protein
                           organism = synthetic construct
VARIANT                    1..4
                           note = This region may encompass 1-4 residues
VARIANT                    6..9
                           note = This region may encompass 1-4 residues
VARIANT                    11..14
                           note = This region may encompass 1-4 residues
SEQUENCE: 189
GGGGSGGGGS GGGGS                                                   15

SEQ ID NO: 190             moltype = AA  length = 6
FEATURE                    Location/Qualifiers
source                     1..6
                           mol_type = protein
                           organism = synthetic construct
SEQUENCE: 190
HHHHHH                                                              6

SEQ ID NO: 191             moltype = AA  length = 15
FEATURE                    Location/Qualifiers
source                     1..15
                           mol_type = protein
                           organism = synthetic construct
SEQUENCE: 191
GGGGSGGGGS GGGGS                                                   15
```

ANTI-GPC3 ANTIBODY

CROSS-REFERENCE TO RELATED APPLICATIONS

This application is a Continuation of U.S. application Ser. No. 16/472,356, which is the U.S. National Stage of PCT/JP2018/000257, filed Jan. 10, 2018, which claims priority to JP 2017-001732, filed Jan. 10, 2017.

The instant application contains a Sequence Listing which has been submitted in XML format via Patent Center and is hereby incorporated by reference in its entirety. Said XML copy, created on May 30, 2023, is named 122882-0105_SL.xml and is 288,299 bytes.

TECHNICAL FIELD

The present invention relates to: an antibody specifically binding to GPC3 (glypican-3) (anti-GPC3 antibody); a chimeric antigen receptor (hereinafter, also referred to as "CAR") comprising anti-GPC3 single chain antibody, a transmembrane region fused with a carboxyl (C) terminus of the anti-GPC3 single chain antibody, and an immunocompetent cell activation signal transduction region fused with a C terminus of the transmembrane region; an immunocompetent cell expressing the CAR; an anti-GPC3 antibody gene or a CAR gene; a vector comprising the anti-GPC3 antibody gene or the CAR gene; a host cell in which the vector has been introduced; a method for detecting GPC3; and a kit for detecting GPC3.

BACKGROUND ART

Glypican-3 (GPC3) is an extracellular matrix protein that is expressed in embryonic tissues, particularly, the liver or the kidney, and associated with organogenesis. The expression of GPC3 is not observed in human adult tissues except for placenta, but is observed in tissues of various cancers such as hepatocellular carcinoma, melanoma, ovarian clear cell adenocarcinoma, and lung squamous cell carcinoma. Thus, GPC3 is a protein that is expressed in embryonic tissues, as in proteins such as α-fetoprotein (AFP) and carcinoembryonic antigen (CEA), and is therefore classified into embryonal carcinoma antigens. Specifically, GPC3 is useful as a target molecule of cancer treatment, a tumor marker and a diagnostic marker, because its feature is that the protein is not expressed in normal tissue cells, but is specifically expressed in cancer cells.

GPC3 is a member of the proteoglycan family that functions as extracellular matrix in cell adhesion in organogenesis or as a receptor of a cell growth factor. A GPI (glycosylphosphatidylinositol) anchor is added to serine at position 560 located on the carboxyl (C)-terminal side of GPC3. The GPI anchor plays a role in localizing GPC3 on cell surface through covalent binding to cell membrane lipid. Also, serine at position 495 and serine at position 509 of GPC3 are modified with a heparan sulfate chain (HS chain). The HS chain is known to regulate a plurality of growth signal transduction pathways such as Wnt signal, FGF signal, and BMP signal transduction pathways. A growth signal transduction pathway involved is known to differ among the types of cancers. For example, in hepatocellular carcinoma (HCC), cells grow by the stimulation of the Wnt signal pathway. A common feature of the glypican family is the number of cysteine as abundant as 16 in an extracellular region, and these cysteine residues are considered to contribute to the stable formation of a conformation by forming a plurality of intramolecular disulfide bonds. The possibility has been reported that GPC3 on cell membrane surface is cleaved between arginine (R) at position 358 and serine (S) at position 359 (R358/S359) by furin convertase. However, since an amino (N)-terminal subunit of GPC3 is cross-linked through intramolecular disulfide bonds, GPC3, even when cleaved into two subunits, an N-terminal subunit and a C-terminal subunit, by furin convertase may probably retain its full-length structure without dissociating these subunits. The structure of soluble GPC3 remains a controversial subject. Thus, there are many unclear points as to the conformation of GPC3 localized on a cell membrane, also including the structures of isoforms of GPC3.

GPC3 on a cell membrane has a complicated structure. Therefore, for preparing an antibody against GPC3, it has been considered desirable that the simplest structural region is an epitope. A representative existing anti-GPC3 antibody includes a monoclonal antibody 1G12 which is distributed by BioMosaics, Inc. This antibody is an antibody obtained by immunizing Balb/c mice with an antigen (C-terminal 70-residue polypeptide of GPC3) designed so as to circumvent the complicated structure or localization of GPC3, to prepare hybridomas, and screening the hybridomas using the antigen. Antibodies GC33 and GC199 developed by a Japanese pharmaceutical manufacturer are also monoclonal antibodies established on the basis of the same concept as above and are antibodies obtained with the C-terminal partial fragment of GPC3 as an antigen (patent document 1).

PRIOR ART DOCUMENT

Patent Document

Patent document 1: Japanese Patent No. 4011100

SUMMARY OF THE INVENTION

Object to be Solved by the Invention

An object of the present invention is to provide: an anti-GPC3 antibody that recognizes an epitope different from that for existing antibodies (e.g., GC33 and GC199) and can specifically bind, even in the form of single chain antibody, to GPC3 localized on a cell membrane; CAR comprising the anti-GPC3 single chain antibody; an immunocompetent cell expressing the CAR; a gene of the anti-GPC3 antibody or a gene of the CAR; a vector comprising the anti-GPC3 antibody gene or the CAR gene; a host cell in which the vector has been introduced; a method for specifically detecting GPC3; and a kit for specifically detecting GPC3.

Means to Solve the Object

The present inventors are continuing diligent studies to attain the object. In the course of the studies, the present inventors have prepared a novel anti-GPC3 antibody by a phage display method which is an approach different from conventional monoclonal antibody preparation methods involving establishing hybridomas. Specifically, an immune library of antibody genes was synthesized using B cells derived from mice immunized with full-length human GPC3, and the genes were reconstituted into a single chain antibody (scFv) library, which was then incorporated into a phage display and expressed on phage surface, followed by biopanning using recombinant full-length human GPC3 and the GPC3-expressing cell line, and further, if necessary, a competitor C-terminal polypeptide of GPC3 serving as an epitope for the existing antibodies, to prepare an anti-GPC3 antibody. The prepared anti-GPC3 antibody has also been confirmed to be useful for cancer immunotherapy using T cells expressing a chimeric antigen receptor (CAR) (hereinafter, also referred to as "CAR-T cells"). The present invention has been completed on the basis of these findings.

Specifically, the present invention is as follows.

[1] An antibody specifically binding to a human GPC3 (glypican-3)-derived polypeptide consisting of the amino acid sequence represented by SEQ ID NO: 155 (hereinafter, also referred to as the "present antibody"), wherein the antibody

- (1-1) comprises a heavy chain complementarity determining region (CDR) 1 consisting of the amino acid sequence represented by SEQ ID NO: 1, a heavy chain CDR2 consisting of the amino acid sequence represented by SEQ ID NO: 2, and a heavy chain CDR3 consisting of the amino acid sequence represented by SEQ ID NO: 3, and
a light chain CDR1 consisting of the amino acid sequence represented by SEQ ID NO: 4, a light chain CDR2 consisting of the amino acid sequence represented by SEQ ID NO: 5, and a light chain CDR3 consisting of the amino acid sequence represented by SEQ ID NO: 6; or
- (2-1) comprises a heavy chain CDR1 consisting of the amino acid sequence represented by SEQ ID NO: 11, a heavy chain CDR2 consisting of the amino acid sequence represented by SEQ ID NO: 12, and a heavy chain CDR3 consisting of the amino acid sequence represented by SEQ ID NO: 13, and
a light chain CDR1 consisting of the amino acid sequence represented by SEQ ID NO: 14, a light chain CDR2 consisting of the amino acid sequence represented by SEQ ID NO: 15, and a light chain CDR3 consisting of the amino acid sequence represented by SEQ ID NO: 16; or
- (3-1) comprises a heavy chain CDR1 consisting of the amino acid sequence represented by SEQ ID NO: 21, a heavy chain CDR2 consisting of the amino acid sequence represented by SEQ ID NO: 22, and a heavy chain CDR3 consisting of the amino acid sequence represented by SEQ ID NO: 23, and
a light chain CDR1 consisting of the amino acid sequence represented by SEQ ID NO: 24, a light chain CDR2 consisting of the amino acid sequence represented by SEQ ID NO: 25, and a light chain CDR3 consisting of the amino acid sequence represented by SEQ ID NO: 26; or
- (4-1) comprises a heavy chain CDR1 consisting of the amino acid sequence represented by SEQ ID NO: 31, a heavy chain CDR2 consisting of the amino acid sequence represented by SEQ ID NO: 32, and a heavy chain CDR3 consisting of the amino acid sequence represented by SEQ ID NO: 33, and
a light chain CDR1 consisting of the amino acid sequence represented by SEQ ID NO: 34, a light chain CDR2 consisting of the amino acid sequence represented by SEQ ID NO: 35, and a light chain CDR3 consisting of the amino acid sequence represented by SEQ ID NO: 36; or
- (5-1) comprises a heavy chain CDR1 consisting of the amino acid sequence represented by SEQ ID NO: 41, a heavy chain CDR2 consisting of the amino acid sequence represented by SEQ ID NO: 42, and a heavy chain CDR3 consisting of the amino acid sequence represented by SEQ ID NO: 43, and
a light chain CDR1 consisting of the amino acid sequence represented by SEQ ID NO: 44, a light chain CDR2 consisting of the amino acid sequence represented by SEQ ID NO: 45, and a light chain CDR3 consisting of the amino acid sequence represented by SEQ ID NO: 46; or
- (6-1) comprises a heavy chain CDR1 consisting of the amino acid sequence represented by SEQ ID NO: 51, a heavy chain CDR2 consisting of the amino acid sequence represented by SEQ ID NO: 52, and a heavy chain CDR3 consisting of the amino acid sequence represented by SEQ ID NO: 53, and
a light chain CDR1 consisting of the amino acid sequence represented by SEQ ID NO: 54, a light chain CDR2 consisting of the amino acid sequence represented by SEQ ID NO: 55, and a light chain CDR3 consisting of the amino acid sequence represented by SEQ ID NO: 56; or
- (7-1) comprises a heavy chain CDR1 consisting of the amino acid sequence represented by SEQ ID NO: 61, a heavy chain CDR2 consisting of the amino acid sequence represented by SEQ ID NO: 62, and a heavy chain CDR3 consisting of the amino acid sequence represented by SEQ ID NO: 63, and
a light chain CDR1 consisting of the amino acid sequence represented by SEQ ID NO: 64, a light chain CDR2 consisting of the amino acid sequence represented by SEQ ID NO: 65, and a light chain CDR3 consisting of the amino acid sequence represented by SEQ ID NO: 66; or
- (8-1) comprises heavy chain CDR1 consisting of the amino acid sequence represented by SEQ ID NO: 71, a heavy chain CDR2 consisting of the amino acid sequence represented by SEQ ID NO: 72, and a heavy chain CDR3 consisting of the amino acid sequence represented by SEQ ID NO: 73, and
a light chain CDR1 consisting of the amino acid sequence represented by SEQ ID NO: 74, a light chain CDR2 consisting of the amino acid sequence represented by SEQ ID NO: 75, and a light chain CDR3 consisting of the amino acid sequence represented by SEQ ID NO: 76; or
- (9-1) comprises a heavy chain CDR1 consisting of the amino acid sequence represented by SEQ ID NO: 81, a heavy chain CDR2 consisting of the amino acid sequence represented by SEQ ID NO: 82, and a heavy chain CDR3 consisting of the amino acid sequence represented by SEQ ID NO: 83, and
a light chain CDR1 consisting of the amino acid sequence represented by SEQ ID NO: 84, a light chain CDR2 consisting of the amino acid sequence represented by SEQ ID NO: 85, and a light chain CDR3 consisting of the amino acid sequence represented by SEQ ID NO: 86; or
- (10-1) comprises a heavy chain CDR1 consisting of the amino acid sequence represented by SEQ ID NO: 91, a heavy chain CDR2 consisting of the amino acid sequence represented by SEQ ID NO: 92, and a heavy chain CDR3 consisting of the amino acid sequence represented by SEQ ID NO: 93, and
a light chain CDR1 consisting of the amino acid sequence represented by SEQ ID NO: 94, a light chain CDR2 consisting of the amino acid sequence represented by SEQ ID NO: 95, and a light chain CDR3 consisting of the amino acid sequence represented by SEQ ID NO: 96; or
(11-1) comprises a heavy chain CDR1 consisting of the amino acid sequence represented by SEQ ID NO: 101, a heavy chain CDR2 consisting of the amino acid sequence represented by SEQ ID NO: 102, and a heavy chain CDR3 consisting of the amino acid sequence represented by SEQ ID NO: 103, and
a light chain CDR1 consisting of the amino acid sequence represented by SEQ ID NO: 104, a light chain CDR2 consisting of the amino acid sequence represented by SEQ ID NO: 105, and a light chain CDR3 consisting of the amino acid sequence represented by SEQ ID NO: 106.

[2] The antibody according to [1], wherein the antibody
(1-2) comprises a heavy chain variable region consisting of an amino acid sequence having at least 80% or higher sequence identity to the amino acid sequence represented by SEQ ID NO: 7, and a light chain variable region consisting of an amino acid sequence having at least 80% or higher sequence identity to the amino acid sequence represented by SEQ ID NO: 8; or
(2-2) comprises a heavy chain variable region consisting of an amino acid sequence having at least 80% or higher sequence identity to the amino acid sequence represented by SEQ ID NO: 17, and a light chain variable region consisting of an amino acid sequence having at least 80% or higher sequence identity to the amino acid sequence represented by SEQ ID NO: 18; or
(3-2) comprises a heavy chain variable region consisting of an amino acid sequence having at least 80% or higher sequence identity to the amino acid sequence represented by SEQ ID NO: 27, and a light chain variable region consisting of an amino acid sequence having at least 80% or higher sequence identity to the amino acid sequence represented by SEQ ID NO: 28; or
(4-2) comprises a heavy chain variable region consisting of an amino acid sequence having at least 80% or higher sequence identity to the amino acid sequence represented by SEQ ID NO: 37, and a light chain variable region consisting of an amino acid sequence having at least 80% or higher sequence identity to the amino acid sequence represented by SEQ ID NO: 38; or
(5-2) comprises a heavy chain variable region consisting of an amino acid sequence having at least 80% or higher sequence identity to the amino acid sequence represented by SEQ ID NO: 47, and a light chain variable region consisting of an amino acid sequence having at least 80% or higher sequence identity to the amino acid sequence represented by SEQ ID NO: 48; or
(6-2) comprises a heavy chain variable region consisting of an amino acid sequence having at least 80% or higher sequence identity to the amino acid sequence represented by SEQ ID NO: 57, and a light chain variable region consisting of an amino acid sequence having at least 80% or higher sequence identity to the amino acid sequence represented by SEQ ID NO: 58; or
(7-2) comprises a heavy chain variable region consisting of an amino acid sequence having at least 80% or higher sequence identity to the amino acid sequence represented by SEQ ID NO: 67, and a light chain variable region consisting of an amino acid sequence having at least 80% or higher sequence identity to the amino acid sequence represented by SEQ ID NO: 68; or
(8-2) comprises a heavy chain variable region consisting of an amino acid sequence having at least 80% or higher sequence identity to the amino acid sequence represented by SEQ ID NO: 77, and a light chain variable region consisting of an amino acid sequence having at least 80% or higher sequence identity to the amino acid sequence represented by SEQ ID NO: 78; or
(9-2) comprises a heavy chain variable region consisting of an amino acid sequence having at least 80% or higher sequence identity to the amino acid sequence represented by SEQ ID NO: 87, and a light chain variable region consisting of an amino acid sequence having at least 80% or higher sequence identity to the amino acid sequence represented by SEQ ID NO: 88; or
(10-2) comprises a heavy chain variable region consisting of an amino acid sequence having at least 80% or higher sequence identity to the amino acid sequence represented by SEQ ID NO: 97, and a light chain variable region consisting of an amino acid sequence having at least 80% or higher sequence identity to the amino acid sequence represented by SEQ ID NO: 98; or
(11-2) comprises a heavy chain variable region consisting of an amino acid sequence having at least 80% or higher sequence identity to the amino acid sequence represented by SEQ ID NO: 107, and a light chain variable region consisting of an amino acid sequence having at least 80% or higher sequence identity to the amino acid sequence represented by SEQ ID NO: 108.

[3] The antibody according to [1] or [2], wherein the antibody is single chain antibody.
[4] The antibody according to [3], wherein the single chain antibody
(1-3) comprises an amino acid sequence having at least 80% or higher sequence identity to the amino acid sequence represented by SEQ ID NO: 165; or
(2-3) comprises an amino acid sequence having at least 80% or higher sequence identity to the amino acid sequence represented by SEQ ID NO: 166; or
(3-3) comprises an amino acid sequence having at least 80% or higher sequence identity to the amino acid sequence represented by SEQ ID NO: 167; or
(4-3) comprises an amino acid sequence having at least 80% or higher sequence identity to the amino acid sequence represented by SEQ ID NO: 168; or
(5-3) comprises an amino acid sequence having at least 80% or higher sequence identity to the amino acid sequence represented by SEQ ID NO: 169; or
(6-3) comprises an amino acid sequence having at least 80% or higher sequence identity to the amino acid sequence represented by SEQ ID NO: 170; or
(7-3) comprises an amino acid sequence having at least 80% or higher sequence identity to the amino acid sequence represented by SEQ ID NO: 171; or
(8-3) comprises an amino acid sequence having at least 80% or higher sequence identity to the amino acid sequence represented by SEQ ID NO: 172; or
(9-3) comprises an amino acid sequence having at least 80% or higher sequence identity to the amino acid sequence represented by SEQ ID NO: 173; or (10-3) comprises an amino acid sequence having at least 80% or higher sequence identity to the amino acid sequence represented by SEQ ID NO: 174; or
(11-3) comprises an amino acid sequence having at least 80% or higher sequence identity to the amino acid sequence represented by SEQ ID NO: 175.

[5] The antibody according to [3], wherein the single chain antibody
(1-3'-1) comprises an amino acid sequence having at least 80% or higher sequence identity to the amino acid sequence represented by SEQ ID NO: 178; or
(1-3'-2) comprises an amino acid sequence having at least 80% or higher sequence identity to the amino acid sequence represented by SEQ ID NO: 179; or
(1-3'-3) comprises an amino acid sequence having at least 80% or higher sequence identity to the amino acid sequence represented by SEQ ID NO: 180; or
(2-3'-1) comprises an amino acid sequence having at least 80% or higher sequence identity to the amino acid sequence represented by SEQ ID NO: 181; or
(2-3'-2) comprises an amino acid sequence having at least 80% or higher sequence identity to the amino acid sequence represented by SEQ ID NO: 182; or
(2-3'-3) comprises an amino acid sequence having at least 80% or higher sequence identity to the amino acid sequence represented by SEQ ID NO: 183; or
(2-3'-4) comprises an amino acid sequence having at least 80% or higher sequence identity to the amino acid sequence represented by SEQ ID NO: 184.

[6] The antibody according to [1] or [2], wherein the antibody
(1-4) comprises a heavy chain consisting of an amino acid sequence having at least 80% or higher sequence identity to the amino acid sequence represented by SEQ ID NO: 9, and a light chain consisting of an amino acid sequence having at least 80% or higher sequence identity to the amino acid sequence represented by SEQ ID NO: 10; or
(2-4) comprises a heavy chain consisting of an amino acid sequence having at least 80% or higher sequence identity to the amino acid sequence represented by SEQ ID NO: 19, and a light chain consisting of an amino acid sequence having at least 80% or higher sequence identity to the amino acid sequence represented by SEQ ID NO: 20; or
(3-4) comprises a heavy chain consisting of an amino acid sequence having at least 80% or higher sequence identity to the amino acid sequence represented by SEQ ID NO: 29, and a light chain consisting of an amino acid sequence having at least 80% or higher sequence identity to the amino acid sequence represented by SEQ ID NO: 30; or
(4-4) comprises a heavy chain consisting of an amino acid sequence having at least 80% or higher sequence identity to the amino acid sequence represented by SEQ ID NO: 39, and a light chain consisting of an amino acid sequence having at least 80% or higher sequence identity to the amino acid sequence represented by SEQ ID NO: 40; or
(5-4) comprises a heavy chain consisting of an amino acid sequence having at least 80% or higher sequence identity to the amino acid sequence represented by SEQ ID NO: 49, and a light chain consisting of an amino acid sequence having at least 80% or higher sequence identity to the amino acid sequence represented by SEQ ID NO: 50; or
(6-4) comprises a heavy chain consisting of an amino acid sequence having at least 80% or higher sequence identity to the amino acid sequence represented by SEQ ID NO: 59, and a light chain consisting of an amino acid sequence having at least 80% or higher sequence identity to the amino acid sequence represented by SEQ ID NO: 60; or
(7-4) comprises a heavy chain consisting of an amino acid sequence having at least 80% or higher sequence identity to the amino acid sequence represented by SEQ ID NO: 69, and a light chain consisting of an amino acid sequence having at least 80% or higher sequence identity to the amino acid sequence represented by SEQ ID NO: 70; or
(8-4) comprises a heavy chain consisting of an amino acid sequence having at least 80% or higher sequence identity to the amino acid sequence represented by SEQ ID NO: 79, and a light chain consisting of an amino acid sequence having at least 80% or higher sequence identity to the amino acid sequence represented by SEQ ID NO: 80; or
(9-4) comprises a heavy chain consisting of an amino acid sequence having at least 80% or higher sequence identity to the amino acid sequence represented by SEQ ID NO: 89, and a light chain consisting of an amino acid sequence having at least 80% or higher sequence identity to the amino acid sequence represented by SEQ ID NO: 90; or
(10-4) comprises a heavy chain consisting of an amino acid sequence having at least 80% or higher sequence identity to the amino acid sequence represented by SEQ ID NO: 99, and a light chain consisting of an amino acid sequence having at least 80% or higher sequence identity to the amino acid sequence represented by SEQ ID NO: 100; or
(11-4) comprises a heavy chain consisting of an amino acid sequence having at least 80% or higher sequence identity to the amino acid sequence represented by SEQ ID NO: 109, and a light chain consisting of an amino acid sequence having at least 80% or higher sequence identity to the amino acid sequence represented by SEQ ID NO: 110.

[7] CAR comprising the antibody according to any one of [3] to [5] (hereinafter, also referred to as the "present single chain antibody"), a transmembrane region fused with a carboxyl terminus of the present single chain antibody, and an immunocompetent cell activation signal transduction region fused with a carboxyl terminus of the transmembrane region (hereinafter, also referred to as the "present CAR").

[8] The CAR according to [7], comprising the amino acid sequence represented by any of SEQ ID NOs: 185 to 187.

[9] An immunocompetent cell expressing the CAR according to [7] or [8] (hereinafter, also referred to as the "present immunocompetent cell").

[10] The immunocompetent cell according to [9], further expressing interleukin 7 (IL-7) and chemokine ligand 19 (CCL19).

[11] An antibody gene encoding the antibody according to any one of [1] to [6] (hereinafter, also referred to as the "present antibody gene"), or a CAR gene encoding the CAR according to [7] or [8] (hereinafter, also referred to as the "present CAR gene").

[12] An antibody gene encoding the antibody according to any one of [1] to [4] and [6].

[13] A vector comprising a promoter, and the antibody gene according to [11] or the CAR gene encoding the CAR according to [11] operably linked downstream of the promoter (hereinafter, also referred to as the "present vector").

[14] A vector comprising a promoter, and the antibody gene according to operably linked downstream of the promoter.

[15] A host cell in which the vector according to or [14] has been introduced (hereinafter, also referred to as the "present host cell").

[16] A method for detecting GPC3 (glypican-3), comprising the step of detecting GPC3 using the antibody according to any one of [1] to [6] (hereinafter, also referred to as the "present detection method").

[17] A kit for the detection of GPC3 (glypican-3), comprising the antibody according to any one of [1] to [6], or a labeled form thereof (hereinafter, also referred to as the "present kit for detection").

Examples of other embodiments of the present invention can include the present antibody for use in the detection of GPC3, and a method for producing the present antibody, comprising the steps of: immunizing nonhuman animals (e.g., mice and rats) with full-length human GPC3 consisting of the amino acid sequence represented by SEQ ID NO: 157; synthesizing cDNA by reverse transcription reaction from total RNA of B cells derived from the immunized nonhuman animals, and amplifying antibody genes to prepare an antibody gene library; and constructing a scFv phage library from the antibody gene library, and infecting *E. coli* with the library so that cells express scFv, followed by biopanning using the full-length human GPC3 and the GPC3-expressing cell line, and further, if necessary, a competitor C-terminal polypeptide of GPC3 (human-derived GPC3 polypeptide consisting of the amino acid sequence represented by SEQ ID NO: 156).

Effect of the Invention

The present antibody is an antibody specifically binding to GPC3 localized on a cell membrane not only in the form of IgG but in the form of scFv. CAR-T cells using the present antibody as scFv in CAR have excellent cytotoxic activity and the ability to produce IFN-γ. Hence, the present antibody is useful for cancer immunotherapy.

MODE OF CARRYING OUT THE INVENTION

Figure 1:
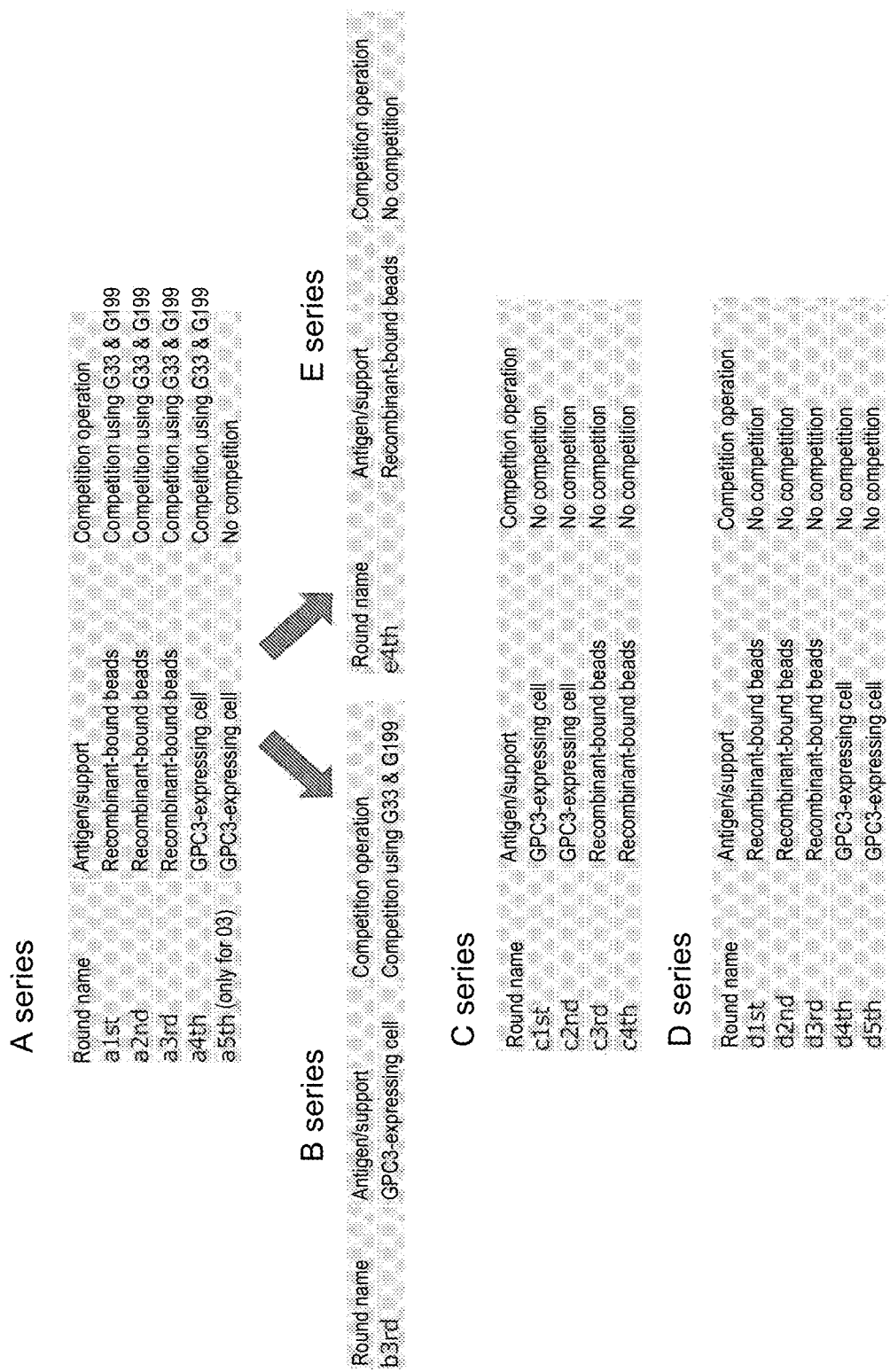
FIG. 1 is a diagram showing each round (step) of biopanning consisting of 5 types of series (A to E series). A series involves performing 3 rounds of biopanning with recombinant GPC3 immobilized on magnetic beads as a bait, and performing biopanning in rounds 4 and with a GPC3-expressing cell line as a bait (round 5 was carried out only for 1413 #3). In rounds 1 to 4, existing anti-GPC3 antibodies (GC33 and GC199) were added as competitive antibodies. B series involves performing biopanning with GPC3-expressing cells as a bait in the presence of the competitive antibodies after round 2 of A series. E series involves performing biopanning with recombinant GPC3 immobilized on magnetic beads as a bait under conditions of no competitive antibody after round 3 of A series. In C series, 4 rounds in total of biopanning with a GPC3-expressing cell line as a bait in 2 rounds and recombinant GPC3 immobilized on magnetic beads as a bait in 2 rounds were performed in the absence of the competitive antibodies. D series involves performing the same biopanning as that of A series in the absence of the competitive antibodies.

The present antibody is an antibody comprising the heavy (H) chain and light (L) chain CDR1 to CDR3 described above in any of (1-1) to (11-1), and specifically binding to, as an epitope, at least a portion (usually within the range of 3 to 30 amino acid residues, preferably 4 to 20 amino acid residues, more preferably 5 to 15 amino acid residues) of a human-derived GPC3 polypeptide consisting of the amino acid sequence represented by SEQ ID NO: 155 (amino

[N]-terminal polypeptide consisting of amino acid residues 32 to 471 [exons 1 to 7] of human-derived full-length GPC3 consisting of the amino acid sequence represented by SEQ ID NO: 157). This antibody specifically binds not only in the form of IgG but in the form of scFv to GPC3 localized on a cell membrane, and usually comprises a H chain variable region comprising the H chain CDR1 to CDR3 described above in any of (1-1) to (11-1), and a L chain variable region comprising the L chain CDR1 to CDR3 described above in any of (1-1) to (11-1). In this context, the phrase "specifically binding" means that the antibody recognizes and binds to the polypeptide consisting of the amino acid sequence represented by SEQ ID NO: 155 through a recognition mechanism with high antigen-antibody specificity. Thus, the present antibody does not specifically bind to a human-derived GPC3 polypeptide consisting of the amino acid sequence represented by SEQ ID NO: 156 (carboxyl [C]-terminal polypeptide consisting of amino acid residues 472 to 580 [exons 8 and 9] of human-derived full-length GPC3 consisting of the amino acid sequence represented by SEQ ID NO: 157).

The present antibody is not particularly limited by its origin, type, class, morphology, etc. The present antibody includes, for example: a human-derived antibody; an antibody derived from a nonhuman animal such as a mouse or a rat; a polyclonal antibody, an oligoclonal antibody (mixture of several to several tens of antibodies), and a monoclonal antibody; and a chimeric antibody or a humanized antibody in which a partial region (e.g., constant regions) of an antibody has been substituted by a region derived from a different organism species, an antibody fragment such as a F(ab') 2 antibody fragment obtained by digesting a monoclonal antibody with pepsin, a Fab' antibody fragment obtained by reducing a F(ab')2 antibody fragment, and Fab obtained by digesting a monoclonal antibody with papain, and a recombinant antibody such as scFv containing an antibody heavy (H) chain variable region and an antibody light (H) chain variable region linked through amino acid cross-links. In the case of using the present antibody as CAR, scFv is preferred.

The present antibody is preferably in a separated form. In this context, the term "separated" means that the antibody is present in a state different from the state where the antibody is originally present in such a way that the antibody is taken out of an environment originally involving the antibody or expressed in an environment different from the environment originally involving the antibody by an artificial operation. Specifically, the "separated antibody" does not include an antibody that is derived from a certain individual and is in a state contained in the body of the individual without an external operation (artificial operation) or in a tissue or a body fluid (blood, plasma, serum, etc.) derived from the body. The present antibody is preferably an antibody prepared by an artificial operation (e.g., the recombinant antibody described above). Such an "antibody derived from a cell prepared by an artificial operation or an antibody produced from the cell" does not include an antibody that is not subjected to an artificial operation, for example, an antibody produced from a naturally occurring B cell.

In the present antibody, a framework region (FR) is usually linked to the N terminus and/or C terminus of each of H chain and L chain CDR1 to CDR3 regions. Among such FRs, examples of the H chain FRs can include H chain FR1 linked to the N terminus of H chain CDR1, H chain FR2 linked to the C terminus of H chain CDR1 (N terminus of H chain CDR2), H chain FR3 linked to the C terminus of H chain CDR2 (N terminus of H chain CDR3), and H chain FR4 linked to the C terminus of H chain CDR3. Among the FRs, examples of the L chain FRs can include L chain FR1 linked to the N terminus of L chain CDR1, L chain FR2 linked to the C terminus of L chain CDR1 (N terminus of L chain CDR2), L chain FR3 linked to the C terminus of L chain CDR2 (N terminus of L chain CDR3), and L chain FR4 linked to the C terminus of L chain CDR3.

Examples of the H chain FR1 can specifically include: (1-HFR1) a polypeptide consisting of amino acid residues 1 to 30 of the amino acid sequence represented by SEQ ID NO: 7, or a polypeptide consisting of an amino acid sequence having at least 80% or higher sequence identity to the amino acid sequence of the polypeptide; (2-HFR1) a polypeptide consisting of amino acid residues 1 to 30 of the amino acid sequence represented by SEQ ID NO: 17, or a polypeptide consisting of an amino acid sequence having at least 80% or higher sequence identity to the amino acid sequence of the polypeptide; (3-HFR1) a polypeptide consisting of amino acid residues 1 to 30 of the amino acid sequence represented by SEQ ID NO: 27, or a polypeptide consisting of an amino acid sequence having at least 80% or higher sequence identity to the amino acid sequence of the polypeptide; (4-HFR1) a polypeptide consisting of amino acid residues 1 to 30 of the amino acid sequence represented by SEQ ID NO: 37, or a polypeptide consisting of an amino acid sequence having at least 80% or higher sequence identity to the amino acid sequence of the polypeptide; (5-HFR1) a polypeptide consisting of amino acid residues 1 to 30 of the amino acid sequence represented by SEQ ID NO: 47, or a polypeptide consisting of an amino acid sequence having at least 80% or higher sequence identity to the amino acid sequence of the polypeptide; (6-HFR1) a polypeptide consisting of amino acid residues 1 to 30 of the amino acid sequence represented by SEQ ID NO: 57, or a polypeptide consisting of an amino acid sequence having at least 80% or higher sequence identity to the amino acid sequence of the polypeptide; (7-HFR1) a polypeptide consisting of amino acid residues 1 to 30 of the amino acid sequence represented by SEQ ID NO: 67, or a polypeptide consisting of an amino acid sequence having at least 80% or higher sequence identity to the amino acid sequence of the polypeptide; (8-HFR1) a polypeptide consisting of amino acid residues 1 to 30 of the amino acid sequence represented by SEQ ID NO: 77, or a polypeptide consisting of an amino acid sequence having at least 80% or higher sequence identity to the amino acid sequence of the polypeptide; (9-HFR1) a polypeptide consisting of amino acid residues 1 to 30 of the amino acid sequence represented by SEQ ID NO: 87, or a polypeptide consisting of an amino acid sequence having at least 80% or higher sequence identity to the amino acid sequence of the polypeptide; (10-HFR1) a polypeptide consisting of amino acid residues 1 to 30 of the amino acid sequence represented by SEQ ID NO: 97, or a polypeptide consisting of an amino acid sequence having at least 80% or higher sequence identity to the amino acid sequence of the polypeptide; and (11-HFR1) a polypeptide consisting of amino acid residues 1 to 30 of the amino acid sequence represented by SEQ ID NO: 107, or a polypeptide consisting of an amino acid sequence having at least 80% or higher sequence identity to the amino acid sequence of the polypeptide.

Examples of the H chain FR2 can specifically include: (1-HFR2) a polypeptide consisting of amino acid residues 36 to 49 of the amino acid sequence represented by SEQ ID NO: 7, or a polypeptide consisting of an amino acid sequence having at least 80% or higher sequence identity to the amino acid sequence of the polypeptide; (2-HFR2) a polypeptide consisting of amino acid residues 36 to 49 of the amino acid sequence represented by SEQ ID NO: 17, or a polypeptide consisting of an amino acid sequence having at least 80% or higher sequence identity to the amino acid sequence of the polypeptide; (3-HFR2) a polypeptide consisting of amino acid residues 36 to 49 of the amino acid sequence represented by SEQ ID NO: 27, or a polypeptide consisting of an amino acid sequence having at least 80% or higher sequence identity to the amino acid sequence of the polypeptide; (4-HFR2) a polypeptide consisting of amino acid residues 36 to 49 of the amino acid sequence represented by SEQ ID NO: 37, or a polypeptide consisting of an amino acid sequence having at least 80% or higher sequence identity to the amino acid sequence of the polypeptide; (5-HFR2) a polypeptide consisting of amino acid residues 36 to 49 of the amino acid sequence represented by SEQ ID NO: 47, or a polypeptide consisting of an amino acid sequence having at least 80% or higher sequence identity to the amino acid sequence of the polypeptide; (6-HFR2) a polypeptide consisting of amino acid residues 36 to 49 of the amino acid sequence represented by SEQ ID NO: 57, or a polypeptide consisting of an amino acid sequence having at least 80% or higher sequence identity to the amino acid sequence of the polypeptide; (7-HFR2) a polypeptide consisting of amino acid residues 36 to 49 of the amino acid sequence represented by SEQ ID NO: 67, or a polypeptide consisting of an amino acid sequence having at least 80% or higher sequence identity to the amino acid sequence of the polypeptide; (8-HFR2) a polypeptide consisting of amino acid residues 36 to 49 of the amino acid sequence represented by SEQ ID NO: 77, or a polypeptide consisting of an amino acid sequence having at least 80% or higher sequence identity to the amino acid sequence of the polypeptide; (9-HFR2) a polypeptide consisting of amino acid residues 36 to 49 of the amino acid sequence represented by SEQ ID NO: 87, or a polypeptide consisting of an amino acid sequence having at least 80% or higher sequence identity to the amino acid sequence of the polypeptide; (10-HFR2) a polypeptide consisting of amino acid residues 36 to 49 of the amino acid sequence represented by SEQ ID NO: 97, or a polypeptide consisting of an amino acid sequence having at least 80% or higher sequence identity to the amino acid sequence of the polypeptide; and (11-HFR2) a polypeptide consisting of amino acid residues 36 to 49 of the amino acid sequence represented by SEQ ID NO: 107, or a polypeptide consisting of an amino acid sequence having at least 80% or higher sequence identity to the amino acid sequence of the polypeptide.

Examples of the H chain FR3 can specifically include: (1-HFR3) a polypeptide consisting of amino acid residues 67 to 98 of the amino acid sequence represented by SEQ ID NO: 7, or a polypeptide consisting of an amino acid sequence having at least 80% or higher sequence identity to the amino acid sequence of the polypeptide; (2-HFR3) a polypeptide consisting of amino acid residues 67 to 98 of the amino acid sequence represented by SEQ ID NO: 17, or a polypeptide consisting of an amino acid sequence having at least 80% or higher sequence identity to the amino acid sequence of the polypeptide; (3-HFR3) a polypeptide consisting of amino acid residues 67 to 98 of the amino acid sequence represented by SEQ ID NO: 27, or a polypeptide consisting of an amino acid sequence having at least 80% or higher sequence identity to the amino acid sequence of the polypeptide; (4-HFR3) a polypeptide consisting of amino acid residues 67 to 99 of the amino acid sequence represented by SEQ ID NO: 37, or a polypeptide consisting of an amino acid sequence having at least 80% or higher sequence identity to the amino acid sequence of the polypeptide; (5-HFR3) a polypeptide consisting of amino acid residues 67 to 99 of the amino acid sequence represented by SEQ ID NO: 47, or a polypeptide consisting of an amino acid sequence having at least 80% or higher sequence identity to the amino acid sequence of the polypeptide; (6-HFR3) a polypeptide consisting of amino acid residues 67 to 98 of the amino acid sequence represented by SEQ ID NO: 57, or a polypeptide consisting of an amino acid sequence having at least 80% or higher sequence identity to the amino acid sequence of the polypeptide; (7-HFR3) a polypeptide consisting of amino acid residues 67 to 98 of the amino acid sequence represented by SEQ ID NO: 67, or a polypeptide consisting of an amino acid sequence having at least 80% or higher sequence identity to the amino acid sequence of the polypeptide; (8-HFR3) a polypeptide consisting of amino acid residues 67 to 98 of the amino acid sequence represented by SEQ ID NO: 77, or a polypeptide consisting of an amino acid sequence having at least 80% or higher sequence identity to the amino acid sequence of the polypeptide; (9-HFR3) a polypeptide consisting of amino acid residues 67 to 99 of the amino acid sequence represented by SEQ ID NO: 87, or a polypeptide consisting of an amino acid sequence having at least 80% or higher sequence identity to the amino acid sequence of the polypeptide; (10-HFR3) a polypeptide consisting of amino acid residues 67 to 98 of the amino acid sequence represented by SEQ ID NO: 97, or a polypeptide consisting of an amino acid sequence having at least 80% or higher sequence identity to the amino acid sequence of the polypeptide; and (11-HFR3) a polypeptide consisting of amino acid residues 67 to 98 of the amino acid sequence represented by SEQ ID NO: 107, or a polypeptide consisting of an amino acid sequence having at least 80% or higher sequence identity to the amino acid sequence of the polypeptide.

Examples of the H chain FR4 can specifically include: (1-HFR4) a polypeptide consisting of amino acid residues 109 to 118 of the amino acid sequence represented by SEQ ID NO: 7, or a polypeptide consisting of an amino acid sequence having at least 80% or higher sequence identity to the amino acid sequence of the polypeptide; (2-HFR4) a polypeptide consisting of amino acid residues 108 to 117 of the amino acid sequence represented by SEQ ID NO: 17, or a polypeptide consisting of an amino acid sequence having at least 80% or higher sequence identity to the amino acid sequence of the polypeptide; (3-HFR4) a polypeptide consisting of amino acid residues 106 to 115 of the amino acid sequence represented by SEQ ID NO: 27, or a polypeptide consisting of an amino acid sequence having at least 80% or higher sequence identity to the amino acid sequence of the polypeptide; (4-HFR4) a polypeptide consisting of amino acid residues 111 to 120 of the amino acid sequence represented by SEQ ID NO: 37, or a polypeptide consisting of an amino acid sequence having at least 80% or higher sequence identity to the amino acid sequence of the polypeptide; (5-HFR4) a polypeptide consisting of amino acid residues 108 to 117 of the amino acid sequence represented by SEQ ID NO: 47, or a polypeptide consisting of an amino acid sequence having at least 80% or higher sequence identity to the amino acid sequence of the polypeptide; (6-HFR4) a polypeptide consisting of amino acid residues 107 to 116 of the amino acid sequence represented by SEQ ID NO: 57, or a polypeptide consisting of an amino acid sequence having at least 80% or higher sequence identity to the amino acid sequence of the polypeptide; (7-HFR4) a polypeptide consisting of amino acid residues 106 to 115 of the amino acid sequence represented by SEQ ID NO: 67, or a polypeptide consisting of an amino acid sequence having at least 80% or higher sequence identity to the amino acid sequence of the polypeptide; (8-HFR4) a polypeptide consisting of amino acid residues 106 to 115 of the amino acid sequence represented by SEQ ID NO: 77, or a polypeptide consisting of an amino acid sequence having at least 80% or higher sequence identity to the amino acid sequence of the polypeptide; (9-HFR4) a polypeptide consisting of amino acid residues 111 to 120 of the amino acid sequence represented by SEQ ID NO: 87, or a polypeptide consisting of an amino acid sequence having at least 80% or higher sequence identity to the amino acid sequence of the polypeptide; (10-HFR4) a polypeptide consisting of amino acid residues 110 to 119 of the amino acid sequence represented by SEQ ID NO: 97, or a polypeptide consisting of an amino acid sequence having at least 80% or higher sequence identity to the amino acid sequence of the polypeptide; and (11-HFR4) a polypeptide consisting of amino acid residues 109 to 118 of the amino acid sequence represented by SEQ ID NO: 107, or a polypeptide consisting of an amino acid sequence having at least 80% or higher sequence identity to the amino acid sequence of the polypeptide.

Examples of the L chain FR1 can specifically include: (1-LFR1) a polypeptide consisting of amino acid residues 1 to 23 of the amino acid sequence represented by SEQ ID NO: 8, or a polypeptide consisting of an amino acid sequence having at least 80% or higher sequence identity to the amino acid sequence of the polypeptide; (2-LFR1) a polypeptide consisting of amino acid residues 1 to 23 of the amino acid sequence represented by SEQ ID NO: 18, or a polypeptide consisting of an amino acid sequence having at least 80% or higher sequence identity to the amino acid sequence of the polypeptide; (3-LFR1) a polypeptide consisting of amino acid residues 1 to 23 of the amino acid sequence represented by SEQ ID NO: 28, or a polypeptide consisting of an amino acid sequence having at least 80% or higher sequence identity to the amino acid sequence of the polypeptide; (4-LFR1) a polypeptide consisting of amino acid residues 1 to 23 of the amino acid sequence represented by SEQ ID NO: 38, or a polypeptide consisting of an amino acid sequence having at least 80% or higher sequence identity to the amino acid sequence of the polypeptide; (5-LFR1) a polypeptide consisting of amino acid residues 1 to 23 of the amino acid sequence represented by SEQ ID NO: 48, or a polypeptide consisting of an amino acid sequence having at least 80% or higher sequence identity to the amino acid sequence of the polypeptide; (6-LFR1) a polypeptide consisting of amino acid residues 1 to 23 of the amino acid sequence represented by SEQ ID NO: 58, or a polypeptide consisting of an amino acid sequence having at least 80% or higher sequence identity to the amino acid sequence of the polypeptide; (7-LFR1) a polypeptide consisting of amino acid residues 1 to 23 of the amino acid sequence represented by SEQ ID NO: 68, or a polypeptide consisting of an amino acid sequence having at least 80% or higher sequence identity to the amino acid sequence of the polypeptide; (8-LFR1) a polypeptide consisting of amino acid residues 1 to 23 of the amino acid sequence represented by SEQ ID NO: 78, or a polypeptide consisting of an amino acid sequence having at least 80% or higher sequence identity to the amino acid sequence of the polypeptide; (9-LFR1) a polypeptide consisting of amino acid residues 1 to 23 of the amino acid sequence represented by SEQ ID NO: 88, or a polypeptide consisting of an amino acid sequence having at least 80% or higher sequence identity to the amino acid sequence of the polypeptide; (10-LFR1) a polypeptide consisting of amino acid residues 1 to 23 of the amino acid sequence represented by SEQ ID NO: 98, or a polypeptide consisting of an amino acid sequence having at least 80% or higher sequence identity to the amino acid sequence of the polypeptide; and (11-LFR1) a polypeptide consisting of amino acid residues 1 to 23 of the amino acid sequence represented by SEQ ID NO: 108, or a polypeptide consisting of an amino acid sequence having at least 80% or higher sequence identity to the amino acid sequence of the polypeptide.

Examples of the L chain FR2 can specifically include: (1-LFR2) a polypeptide consisting of amino acid residues 35 to 49 of the amino acid sequence represented by SEQ ID NO: 8, or a polypeptide consisting of an amino acid sequence having at least 80% or higher sequence identity to the amino acid sequence of the polypeptide; (2-LFR2) a polypeptide consisting of amino acid residues to 54 of the amino acid sequence represented by SEQ ID NO: 18, or a polypeptide consisting of an amino acid sequence having at least 80% or higher sequence identity to the amino acid sequence of the polypeptide; (3-LFR2) a polypeptide consisting of amino acid residues 35 to 49 of the amino acid sequence represented by SEQ ID NO: 28, or a polypeptide consisting of an amino acid sequence having at least 80% or higher sequence identity to the amino acid sequence of the polypeptide; (4-LFR2) a polypeptide consisting of amino acid residues 35 to 49 of the amino acid sequence represented by SEQ ID NO: 38, or a polypeptide consisting of an amino acid sequence having at least 80% or higher sequence identity to the amino acid sequence of the polypeptide; (5-LFR2) a polypeptide consisting of amino acid residues 41 to 55 of the amino acid sequence represented by SEQ ID NO: 48, or a polypeptide consisting of an amino acid sequence having at least 80% or higher sequence identity to the amino acid sequence of the polypeptide; (6-LFR2) a polypeptide consisting of amino acid residues 35 to 49 of the amino acid sequence represented by SEQ ID NO: 58, or a polypeptide consisting of an amino acid sequence having at least 80% or higher sequence identity to the amino acid sequence of the polypeptide; (7-LFR2) a polypeptide consisting of amino acid residues 35 to 49 of the amino acid sequence represented by SEQ ID NO: 68, or a polypeptide consisting of an amino acid sequence having at least 80% or higher sequence identity to the amino acid sequence of the polypeptide; (8-LFR2) a polypeptide consisting of amino acid residues 35 to 49 of the amino acid sequence represented by SEQ ID NO: 78, or a polypeptide consisting of an amino acid sequence having at least 80% or higher sequence identity to the amino acid sequence of the polypeptide; (9-LFR2) a polypeptide consisting of amino acid residues 35 to 49 of the amino acid sequence represented by SEQ ID NO: 88, or a polypeptide consisting of an amino acid sequence having at least 80% or higher sequence identity to the amino acid sequence of the polypeptide; (10-LFR2) a polypeptide consisting of amino acid residues 35 to 49 of the amino acid sequence represented by SEQ ID NO: 98, or a polypeptide consisting of an amino acid sequence having at least 80% or higher sequence identity to the amino acid sequence of the polypeptide; and (11-LFR2) a polypeptide consisting of amino acid residues 35 to 49 of the amino acid sequence represented by SEQ ID NO: 108, or a polypeptide consisting of an amino acid sequence having at least 80% or higher sequence identity to the amino acid sequence of the polypeptide.

Examples of the L chain FR3 can specifically include: (1-LFR3) a polypeptide consisting of amino acid residues 57 to 88 of the amino acid sequence represented by SEQ ID NO: 8, or a polypeptide consisting of an amino acid sequence having at least 80% or higher sequence identity to the amino acid sequence of the polypeptide; (2-LFR3) a polypeptide consisting of amino acid residues 62 to 93 of the amino acid sequence represented by SEQ ID NO: 18, or a polypeptide consisting of an amino acid sequence having at least 80% or higher sequence identity to the amino acid sequence of the polypeptide; (3-LFR3) a polypeptide consisting of amino acid residues 57 to 88 of the amino acid sequence represented by SEQ ID NO: 28, or a polypeptide consisting of an amino acid sequence having at least 80% or higher sequence identity to the amino acid sequence of the polypeptide; (4-LFR3) a polypeptide consisting of amino acid residues 57 to 88 of the amino acid sequence represented by SEQ ID NO: 38, or a polypeptide consisting of an amino acid sequence having at least 80% or higher sequence identity to the amino acid sequence of the polypeptide; (5-LFR3) a polypeptide consisting of amino acid residues 63 to 94 of the amino acid sequence represented by SEQ ID NO: 48, or a polypeptide consisting of an amino acid sequence having at least 80% or higher sequence identity to the amino acid sequence of the polypeptide; (6-LFR3) a polypeptide consisting of amino acid residues 57 to 88 of the amino acid sequence represented by SEQ ID NO: 58, or a polypeptide consisting of an amino acid sequence having at least 80% or higher sequence identity to the amino acid sequence of the polypeptide; (7-LFR3) a polypeptide consisting of amino acid residues 57 to 88 of the amino acid sequence represented by SEQ ID NO: 68, or a polypeptide consisting of an amino acid sequence having at least 80% or higher sequence identity to the amino acid sequence of the polypeptide; (8-LFR3) a polypeptide consisting of amino acid residues 57 to 88 of the amino acid sequence represented by SEQ ID NO: 78, or a polypeptide consisting of an amino acid sequence having at least 80% or higher sequence identity to the amino acid sequence of the polypeptide; (9-LFR3) a polypeptide consisting of amino acid residues 57 to 88 of the amino acid sequence represented by SEQ ID NO: 88, or a polypeptide consisting of an amino acid sequence having at least 80% or higher sequence identity to the amino acid sequence of the polypeptide; (10-LFR3) a polypeptide consisting of amino acid residues 57 to 88 of the amino acid sequence represented by SEQ ID NO: 98, or a polypeptide consisting of an amino acid sequence having at least 80% or higher sequence identity to the amino acid sequence of the polypeptide; and (11-LFR3) a polypeptide consisting of amino acid residues 57 to 88 of the amino acid sequence represented by SEQ ID NO: 108, or a polypeptide consisting of an amino acid sequence having at least 80% or higher sequence identity to the amino acid sequence of the polypeptide.

Examples of the L chain FR4 can specifically include: (1-LFR4) a polypeptide consisting of amino acid residues 98 to 108 of the amino acid sequence represented by SEQ ID NO: 8, or a polypeptide consisting of an amino acid sequence having at least 80% or higher sequence identity to the amino acid sequence of the polypeptide; (2-LFR4) a polypeptide consisting of amino acid residues 103 to 113 of the amino acid sequence represented by SEQ ID NO: 18, or a polypeptide consisting of an amino acid sequence having at least 80% or higher sequence identity to the amino acid sequence of the polypeptide; (3-LFR4) a polypeptide consisting of amino acid residues 97 to 107 of the amino acid sequence represented by SEQ ID NO: 28, or a polypeptide consisting of an amino acid sequence having at least 80% or higher sequence identity to the amino acid sequence of the polypeptide; (4-LFR4) a polypeptide consisting of amino acid residues 98 to 108 of the amino acid sequence represented by SEQ ID NO: 38, or a polypeptide consisting of an amino acid sequence having at least 80% or higher sequence identity to the amino acid sequence of the polypeptide; (5-LFR4) a polypeptide consisting of amino acid residues 104 to 114 of the amino acid sequence represented by SEQ ID NO: 48, or a polypeptide consisting of an amino acid sequence having at least 80% or higher sequence identity to the amino acid sequence of the polypeptide; (6-LFR4) a polypeptide consisting of amino acid residues 98 to 108 of the amino acid sequence represented by SEQ ID NO: 58, or a polypeptide consisting of an amino acid sequence having at least 80% or higher sequence identity to the amino acid sequence of the polypeptide; (7-LFR4) a polypeptide consisting of amino acid residues 98 to 108 of the amino acid sequence represented by SEQ ID NO: 68, or a polypeptide consisting of an amino acid sequence having at least 80% or higher sequence identity to the amino acid sequence of the polypeptide; (8-LFR4) a polypeptide consisting of amino acid residues 98 to 108 of the amino acid sequence represented by SEQ ID NO: 78, or a polypeptide consisting of an amino acid sequence having at least 80% or higher sequence identity to the amino acid sequence of the polypeptide; (9-LFR4) a polypeptide consisting of amino acid residues 98 to 108 of the amino acid sequence represented by SEQ ID NO: 88, or a polypeptide consisting of an amino acid sequence having at least 80% or higher sequence identity to the amino acid sequence of the polypeptide; (10-LFR4) a polypeptide consisting of amino acid residues 98 to 108 of the amino acid sequence represented by SEQ ID NO: 98, or a polypeptide consisting of an amino acid sequence having at least 80% or higher sequence identity to the amino acid sequence of the polypeptide; and (11-LFR4) a polypeptide consisting of amino acid residues 98 to 108 of the amino acid sequence represented by SEQ ID NO: 108, or a polypeptide consisting of an amino acid sequence having at least 80% or higher sequence identity to the amino acid sequence of the polypeptide.

The FRs of the present antibody are preferably FRs of a known human antibody. Examples of such "FRs of a known human antibody" can include FRs of a human antibody registered in a sequence database known in the art such as GenBank, and FRs selected from a common sequence (human most homologous consensus sequence; Kabat, E. A. et al., Sequences of Proteins of Immunological Interest, US Dept. Health and Human Services, 1991) derived from each subgroup of a human antibody.

The H chain CDR1 in the present antibody usually resides at positions H31 to H35 based on Kabat numbering (see the document "Kabat, E. A. et al., (1991) NIH Publication No. 91-3242, sequences of proteins of immunological interest"). The H chain CDR2 in the present antibody usually resides at positions H50 to H52, H52A, and H53 to H65 based on Kabat numbering. The H chain CDR3 in the present antibody usually resides at positions H95 to H100, H100A, H100B, H101, and H102 based on Kabat numbering. The L chain CDR1 in the present antibody usually resides at positions L24 to L34 based on Kabat numbering. The L chain CDR2 in the present antibody usually resides at positions L50 to L56 based on Kabat numbering. The L chain CDR3 in the present antibody usually resides at positions L89 to L97 based on Kabat numbering.

Examples of the antibody comprising the H chain and L chain CDR1 to CDR3 described above in (1-1) as the present antibody can include an antibody comprising the H chain and L chain variable (V) regions described above in (1-2) and can specifically include: the single chain antibody described above in (1-3); the single chain antibody described above in (1-3'-1), the single chain antibody described above in (1-3'-2), and the single chain antibody described above in (1-3'-3); and an antibody comprising the H chain and the L chain described above in (1-4). Examples of the antibody comprising the H chain and L chain CDR1 to CDR3 described above in (2-1) can include an antibody comprising the H chain and L chain V regions described above in (2-2) and can specifically include: the single chain antibody described above in (2-3); the single chain antibody described above in (2-3'-1), the single chain antibody described above in (2-3'-2), the single chain antibody described above in (2-3'-3), and the single chain antibody described above in (2-3'-4); and an antibody comprising the H chain and the L chain described above in (2-4). Examples of the antibody comprising the H chain and L chain CDR1 to CDR3 described above in (3-1) can include an antibody comprising the H chain and L chain V regions described above in (3-2) and can specifically include: the single chain antibody described above in (3-3); and an antibody comprising the H chain and the L chain described above in (3-4). Examples of the antibody comprising the H chain and L chain CDR1 to CDR3 described above in (4-1) can include an antibody comprising the H chain and L chain V regions described above in (4-2) and can specifically include: the single chain antibody described above in (4-3); and an antibody comprising the H chain and the L chain described above in (4-4). Examples of the antibody comprising the H chain and L chain CDR1 to CDR3 described above in (5-1) can include an antibody comprising the H chain and L chain V regions described above in (5-2) and can specifically include: the single chain antibody described above in (5-3); and an antibody comprising the H chain and the L chain described above in (5-4). Examples of the antibody comprising the H chain and L chain CDR1 to CDR3 described above in (6-1) can include an antibody comprising the H chain and L chain V regions described above in (6-2) and can specifically include: the single chain antibody described above in (6-3); and an antibody comprising the H chain and the L chain described above in (6-4). Examples of the antibody comprising the H chain and L chain CDR1 to CDR3 described above in (7-1) can include an antibody comprising the H chain and L chain V regions described above in (7-2) and can specifically include: the single chain antibody described above in (7-3); and an antibody comprising the H chain and the L chain described above in (7-4). Examples of the antibody comprising the H chain and L chain CDR1 to CDR3 described above in (8-1) can include an antibody comprising the H chain and L chain V regions described above in (8-2) and can specifically include: the single chain antibody described above in (8-3); and an antibody comprising the H chain and the L chain described above in (8-4). Examples of the antibody comprising the H chain and L chain CDR1 to CDR3 described above in (9-1) can include an antibody comprising the H chain and L chain V regions described above in (9-2) and can specifically include: the single chain antibody described above in (9-3); and an antibody comprising the H chain and the L chain described above in (9-4). Examples of the antibody comprising the H chain and L chain CDR1 to CDR3 described above in (10-1) can include an antibody comprising the H chain and L chain V regions described above in (10-2) and can specifically include: the single chain antibody described above in (10-3); and an antibody comprising the H chain and the L chain described above in (10-4). Examples of the antibody comprising the H chain and L chain CDR1 to CDR3 described above in (11-1) can include an antibody comprising the H chain and L chain V regions described above in (11-2) and can specifically include: the single chain antibody described above in (11-3); and an antibody comprising the H chain and the L chain described above in (11-4). The heavy chain variable region and the light chain variable region in the single chain antibody are usually bound via a peptide linker.

The present CAR can comprise the present single chain antibody, a transmembrane region fused with the C terminus of the present single chain antibody, and an immunocompetent cell activation signal transduction region fused with the C terminus of the transmembrane region. In this context, the fusion between the present single chain antibody and the transmembrane region, or between the transmembrane region and the immunocompetent cell activation signal transduction region may be mediated by a peptide linker or an IgG4 hinge region.

Examples of the length of the peptide linker in the present antibody can include 1 to 100 amino acid residues, preferably 10 to 50 amino acid residues. Examples of the peptide linker in the present antibody can specifically include a consecutive linkage of 3 amino acid sequences each consisting of 1 to 4 glycine residues and 1 serine residue (SEQ ID NO: 189).

The transmembrane region can be any peptide that can penetrate a cell membrane. Examples thereof can include a transmembrane region derived from CD8, a T cell receptor α or β chain, CD3ζ, CD28, CD3E, CD45, CD4, CD5, CD8, CD9, CD16, CD22, CD33, CD37, CD64, CD80, CD86, CD134, CD137, ICOS, CD154, EGFR (epidermal growth factor receptor), or GITR and can specifically include a human CD8 transmembrane region consisting of amino acid residues 1 to 83 of the amino acid sequence represented by SEQ ID NO: 185. Alternatively, the transmembrane region may be derived from a peptide that can penetrate cell membrane by the truncation of C-terminal 1 to 10 amino acid residues, preferably 6 or 7 amino acid residues. Examples thereof can include engineered form 1 of the human CD8 transmembrane region consisting of amino acid residues 1 to 77 of the amino acid sequence represented by SEQ ID NO: 186, and engineered form 2 of the human CD8 transmembrane region consisting of amino acid residues 1 to 76 of the amino acid sequence represented by SEQ ID NO: 187.

The immunocompetent cell activation signal transduction region can be any region capable of transducing a signal into immunocompetent cells upon binding of the present single chain antibody to human GPC3. The immunocompetent cell activation signal transduction region preferably comprises at least one or more members selected from polypeptides of the intracellular regions of CD28, 4-1BB (CD137), GITR, CD27, OX40, HVEM, CD3ζ, and Fc receptor-associated γ chain, and more preferably comprises three polypeptides of the intracellular regions of CD28, 4-1BB, and CD3ζ. Examples of such a polypeptide of the intracellular region of CD28 can specifically include a polypeptide of the intracellular region of human CD28 consisting of amino acid residues 85 to 124 of the amino acid sequence represented by SEQ ID NO: 185. Examples of the "polypeptide of the intracellular region of 4-1BB" can specifically include a polypeptide of the intracellular region of human 4-1BB consisting of amino acid residues 125 to 170 of the amino acid sequence represented by SEQ ID NO: 185. Examples of the polypeptide of the intracellular region of CD3ζ can specifically include a polypeptide of the intracellular region of human CD3ζ consisting of amino acid residues 172 to 283 of the amino acid sequence represented by SEQ ID NO: 185.

Arginine (Arg) at position 84 of the amino acid sequence represented by SEQ ID NO: 185, arginine at position 78 of the amino acid sequence represented by SEQ ID NO: 186, and arginine at position 77 of the amino acid sequence represented by SEQ ID NO: 187 are a common sequence between the polypeptide of the transmembrane region derived from human CD8 and the polypeptide of the intracellular region of human CD28. Leucine (Leu) at position 171 of the amino acid sequence represented by SEQ ID NO: 185, leucine at position 165 of the amino acid sequence represented by SEQ ID NO: 186, and leucine at position 164 of the amino acid sequence represented by SEQ ID NO: 187 are a common sequence between the polypeptide of the intracellular region of human 4-1BB and the polypeptide of the intracellular region of human CD3.

In the present specification, the "immunocompetent cell" means a cell responsible for immune functions in a living body. Examples of the immunocompetent cell can include: a lymphoid cell such as a T cell, a natural killer cell (NK cell), and a B cell; an antigen-presenting cell such as a monocyte, a macrophage, and a dendritic cell; and a granulocyte such as a neutrophil, an eosinophil, a basophil, and a mast cell. Specific examples thereof can preferably include a T cell derived from a mammal such as a human, a dog, a cat, a pig, or a mouse, preferably a human-derived T cell. The T cell can be obtained by isolation or purification from an immunocompetent cell infiltrating a body fluid such as blood or bone marrow fluid, a tissue of the spleen, the thymus, lymph node or the like, or a cancer tissue of primary tumor, metastatic tumor, cancerous ascites or the like. Alternatively, a T cell prepared from an ES cell or an iPS cell may be utilized. Examples of such a T cell can include an alpha-beta T cell, a gamma-delta T cell, a $CD8^+$ T cell, a $CD4^+$ T cell, a tumor-infiltrating T cell, a memory T cell, a naive T cell, and a NKT cell. The origin of the immunocompetent cell may be the same as or different from an administration subject. When the administration subject is a human, an autologous cell collected from a patient as the administration subject may be used as the immunocompetent cell, or any of other cells collected from a person other than the administration subject may be used as the immunocompetent cell. Specifically, the donor and the recipient may be the same or different and is preferably the same.

Examples of the administration subject can preferably include a mammal and a mammalian cell. Examples of the mammal can more preferably include a human, a mouse, a dog, a rat, a guinea pig, a rabbit, a bird, sheep, a pig, cattle, a horse, a cat, a monkey, and a chimpanzee, particularly preferably a human.

The present CAR is preferably used for ex vivo expression on the cell surface of the immunocompetent cell collected from a cancer patient in cancer treatment. In the case of using a T cell as the immunocompetent cell, examples of the peptide consisting of the transmembrane region and the immunocompetent cell activation signal transduction region fused with the C terminus of the transmembrane region in the present CAR can specifically include a peptide consisting of the amino acid sequence represented by any of SEQ ID NOs: 185 to 187. Examples of the present CAR can specifically include CAR comprising single chain antibody selected from the group consisting of the single chain antibody described above in (1-3), the single chain antibody described above in (2-3), the single chain antibody described above in (1-3'-1), the single chain antibody described above in (1-3'-2), the single chain antibody described above in (1-3'-3), the single chain antibody described above in (2-3'-1), the single chain antibody described above in (2-3'-2), the single chain antibody described above in (2-3'-3), and the single chain antibody described above in (2-3'-4), and a peptide consisting of the amino acid sequence represented by any of SEQ ID NOs: 185 to 187, fused with the C terminus of the single chain antibody.

Specifically, examples of the present CAR can include
CAR comprising the single chain antibody described above in (1-3), and a peptide consisting of the amino acid sequence represented by SEQ ID NO: 185,
CAR comprising the single chain antibody described above in (1-3), and a peptide consisting of the amino acid sequence represented by SEQ ID NO: 186,
CAR comprising the single chain antibody described above in (1-3), and a peptide consisting of the amino acid sequence represented by SEQ ID NO: 187,
CAR comprising the single chain antibody described above in (1-3'-1), and a peptide consisting of the amino acid sequence represented by SEQ ID NO: 185,
CAR comprising the single chain antibody described above in (1-3'-1), and a peptide consisting of the amino acid sequence represented by SEQ ID NO: 186,
CAR comprising the single chain antibody described above in (1-3'-1), and a peptide consisting of the amino acid sequence represented by SEQ ID NO: 187,
CAR comprising the single chain antibody described above in (1-3'-2), and a peptide consisting of the amino acid sequence represented by SEQ ID NO: 185,
CAR comprising the single chain antibody described above in (1-3'-2), and a peptide consisting of the amino acid sequence represented by SEQ ID NO: 186,
CAR comprising the single chain antibody described above in (1-3'-2), and a peptide consisting of the amino acid sequence represented by SEQ ID NO: 187,
CAR comprising the single chain antibody described above in (1-3'-3), and a peptide consisting of the amino acid sequence represented by SEQ ID NO: 185,
CAR comprising the single chain antibody described above in (1-3'-3), and a peptide consisting of the amino acid sequence represented by SEQ ID NO: 186,
CAR comprising the single chain antibody described above in (1-3'-3), and a peptide consisting of the amino acid sequence represented by SEQ ID NO: 187,
CAR comprising the single chain antibody described above in (2-3), and a peptide consisting of the amino acid sequence represented by SEQ ID NO: 185,
CAR comprising the single chain antibody described above in (2-3), and a peptide consisting of the amino acid sequence represented by SEQ ID NO: 186,
CAR comprising the single chain antibody described above in (2-3), and a peptide consisting of the amino acid sequence represented by SEQ ID NO: 187,
CAR comprising the single chain antibody described above in (2-3'-1), and a peptide consisting of the amino acid sequence represented by SEQ ID NO: 185,
CAR comprising the single chain antibody described above in (2-3'-1), and a peptide consisting of the amino acid sequence represented by SEQ ID NO: 186,
CAR comprising the single chain antibody described above in (2-3'-1), and a peptide consisting of the amino acid sequence represented by SEQ ID NO: 187,
CAR comprising the single chain antibody described above in (2-3'-2), and a peptide consisting of the amino acid sequence represented by SEQ ID NO: 185,
CAR comprising the single chain antibody described above in (2-3'-2), and a peptide consisting of the amino acid sequence represented by SEQ ID NO: 186, CAR comprising the single chain antibody described above in (2-3'-2), and a peptide consisting of the amino acid sequence represented by SEQ ID NO: 187,
CAR comprising the single chain antibody described above in (2-3'-3), and a peptide consisting of the amino acid sequence represented by SEQ ID NO: 185,
CAR comprising the single chain antibody described above in (2-3'-3), and a peptide consisting of the amino acid sequence represented by SEQ ID NO: 186,
CAR comprising the single chain antibody described above in (2-3'-3), and a peptide consisting of the amino acid sequence represented by SEQ ID NO: 187,
CAR comprising the single chain antibody described above in (2-3'-4), and a peptide consisting of the amino acid sequence represented by SEQ ID NO: 185,
CAR comprising the single chain antibody described above in (2-3'-4), and a peptide consisting of the amino acid sequence represented by SEQ ID NO: 186, and
CAR comprising the single chain antibody described above in (2-3'-4), and a peptide consisting of the amino acid sequence represented by SEQ ID NO: 187.

The present immunocompetent cell can be any immunocompetent cell expressing CAR. Since CAR usually does not occur naturally, the immunocompetent cell expresses foreign CAR, not endogenous CAR. The present immunocompetent cell preferably further expresses IL-7 and/or CCL19. When the immunocompetent cell is a cell found to not express IL-7 and/or CCL19, for example, a T cell, or when the immunocompetent cell is a cell, other than a T cell, low expressing IL-7 and/or CCL19, the present immunocompetent cell preferably expresses foreign IL-7 and/or CCL19.

The present immunocompetent cell can be prepared by introducing the present vector comprising the present CAR gene, and a vector comprising IL-7 and/or CCL19 gene to an immunocompetent cell. The introduction method can be any method for introducing DNA to mammalian cells. Examples thereof can include a method such as electroporation (Cytotechnology, 3, 133 (1990)), calcium phosphate method (Japanese unexamined Patent Application Publication No. 2-227075), lipofection (Proc. Natl. Acad. Sci. U.S.A., 84, 7413 (1987)), and viral infection method. Examples of such a viral infection method can include a method which involves transfecting a packaging cell such as a GP2-293 cell (manufactured by Takara Bio Inc.), a Plat-GP cell (manufactured by Cosmo Bio Co., Ltd.), a PG13 cell (ATCC CRL-10686), or a PA317 cell (ATCC CRL-9078) with a CAR expression vector (International Publication No. WO 2016/056228) and a packaging plasmid to prepare a recombinant virus, and infecting a T cell with the recombinant virus.

The present immunocompetent cell may be produced by incorporating a nucleotide encoding the present CAR and a nucleotide encoding IL-7 and/or CCL19 into the genome of a cell by use of a gene editing technique known in the art such that the nucleotides are expressible under the control of an appropriate promoter. Examples of the gene editing technique known in the art include a technique using endonuclease such as zinc finger nuclease, TALEN (transcription activator-like effector nuclease), or CRISPR (clustered regularly interspaced short palindromic repeat)-Cas system.

The present immunocompetent cell can be used in combination with an additional anticancer agent. Examples of the additional anticancer agent can include: an alkylating drug such as cyclophosphamide, bendamustine, ifosfamide, and dacarbazine; an antimetabolite such as pentostatin, fludarabine, cladribine, methotrexate, 5-fluorouracil, 6-mercaptopurine, and enocitabine; a molecular targeting drug such as rituximab, cetuximab, and trastuzumab; a kinase inhibitor such as imatinib, gefitinib, erlotinib, afatinib, dasatinib, sunitinib, and trametinib; a proteasome inhibitor such as bortezomib; a calcineurin inhibitory drug such as cyclosporin and tacrolimus; an anticancer antibiotic such as idarubicin and doxorubicin mitomycin C; a vegetable alkaloid such as irinotecan and etoposide; a platinum-containing drug such as cisplatin, oxaliplatin, and carboplatin; a hormone therapeutic such as tamoxifen and bicalutamide; and an immunosuppressive drug such as interferon, nivolumab, and pembrolizumab.

Examples of the method for "using the present immunocompetent cell in combination with the additional anticancer agent" can include a method using treatment with the additional anticancer agent followed by use of the present immunocompetent cell, a method using the present immunocompetent cell and the additional anticancer agent at the same time, and a method using treatment with the present immunocompetent cell followed by use of the additional anticancer agent. Use of the present immunocompetent cell in combination with the additional anticancer agent can further improve a therapeutic effect on a cancer and can also reduce their respective adverse reactions by decreasing their respective numbers of administration or doses.

The present antibody gene is not particularly limited as long as the antibody gene (nucleotide) encodes the present antibody. Examples thereof can include (1-1D) an antibody gene comprising: a H chain CDR1 gene consisting of nucleotide residues 91 to 105 of a H chain V region gene consisting of the nucleotide sequence represented by SEQ ID NO: 111 (gene encoding the H chain CDR1 described above in (1-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 111 (gene encoding the H chain CDR2 described above in (1-1)), or a degenerate codon engineered form of the H chain CDR2 gene; and a H chain CDR3 gene consisting of nucleotide residues 295 to 324 of the H chain V region gene consisting of the nucleotide sequence represented by SEQ ID NO: 111 (gene encoding the H chain CDR3 described above in (1-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 112 (gene encoding the L chain CDR1 described above in (1-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 112 (gene encoding the L chain CDR2 described above in (1-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 112 (gene encoding the L chain CDR3 described above in (1-1)), or a degenerate codon engineered form of the L chain CDR3 gene, (2-1D) an antibody gene comprising: a H chain CDR1 gene consisting of nucleotide residues 91 to 105 of a H chain V region gene consisting of the nucleotide sequence represented by SEQ ID NO: 115 (gene encoding the H chain CDR1 described above in (2-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 115 (gene encoding the H chain CDR2 described above in (2-1)), or a degenerate codon engineered form of the H chain CDR2 gene; and a H chain CDR3 gene consisting of nucleotide residues 295 to 321 of the H chain V region gene consisting of the nucleotide sequence represented by SEQ ID NO: 115 (gene encoding the H chain CDR3 described above in (2-1)), or a degenerate codon engineered form of the H chain CDR3 gene; and a L chain CDR1 gene consisting of nucleotide residues 70 to 117 of a L chain V region gene consisting of the nucleotide sequence represented by SEQ ID NO: 116 (gene encoding the L chain CDR1 described above in (2-1)), or a degenerate codon engineered form of the L chain CDR1 gene; a L chain CDR2 gene consisting of nucleotide residues 163 to 183 of the L chain V region gene consisting of the nucleotide sequence represented by SEQ ID NO: 116 (gene encoding the L chain CDR2 described above in (2-1)), or a degenerate codon engineered form of the L chain CDR2 gene; and a L chain CDR3 gene consisting of nucleotide residues 280 to 306 of the L chain V region gene consisting of the nucleotide sequence represented by SEQ ID NO: 116 (gene encoding the L chain CDR3 described above in (2-1)), or a degenerate codon engineered form of the L chain CDR3 gene, (3-1D) an antibody gene comprising: a H chain CDR1 gene consisting of nucleotide residues 91 to 105 of a H chain V region gene consisting of the nucleotide sequence represented by SEQ ID NO: 119 (gene encoding the H chain CDR1 described above in (3-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 119 (gene encoding the H chain CDR2 described above in (3-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 119 (gene encoding the H chain CDR3 described above in (3-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 120 (gene encoding the L chain CDR1 described above in (3-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 120 (gene encoding the L chain CDR2 described above in (3-1)), or a degenerate codon engineered form of the L chain CDR2 gene; and a L chain CDR3 gene consisting of nucleotide residues 265 to 288 of the L chain V region gene consisting of the nucleotide sequence represented by SEQ ID NO: 120 (gene encoding the L chain CDR3 described above in (3-1)), or a degenerate codon engineered form of the L chain CDR3 gene, (4-1D) an antibody gene comprising: a H chain CDR1 gene consisting of nucleotide residues 91 to 105 of a H chain V region gene consisting of the nucleotide sequence represented by SEQ ID NO: 123 (gene encoding the H chain CDR1 described above in (4-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 123 (gene encoding the H chain CDR2 described above in (4-1)), or a degenerate codon engineered form of the H chain CDR2 gene; and a H chain CDR3 gene consisting of nucleotide residues 298 to 330 of the H chain V region gene consisting of the nucleotide sequence represented by SEQ ID NO: 123 (gene encoding the H chain CDR3 described above in (4-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 124 (gene encoding the L chain CDR1 described above in (4-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 124 (gene encoding the L chain CDR2 described above in (4-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 124 (gene encoding the L chain CDR3 described above in (4-1)), or a degenerate codon engineered form of the L chain CDR3 gene, (5-1D) an antibody gene comprising: a H chain CDR1 gene consisting of nucleotide residues 91 to 105 of a H chain V region gene consisting of the nucleotide sequence represented by SEQ ID NO: 127 (gene encoding the H chain CDR1 described above in (5-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 127 (gene encoding the H chain CDR2 described above in (5-1)), or a degenerate codon engineered form of the H chain CDR2 gene; and a H chain CDR3 gene consisting of nucleotide residues 298 to 321 of the H chain V region gene consisting of the nucleotide sequence represented by SEQ ID NO: 127 (gene encoding the H chain CDR3 described above in (5-1)), or a degenerate codon engineered form of the H chain CDR3 gene; and a L chain CDR1 gene consisting of nucleotide residues 70 to 120 of a L chain V region gene consisting of the nucleotide sequence represented by SEQ ID NO: 128 (gene encoding the L chain CDR1 described above in (5-1)), or a degenerate codon engineered form of the L chain CDR1 gene; a L chain CDR2 gene consisting of nucleotide residues 166 to 186 of the L chain V region gene consisting of the nucleotide sequence represented by SEQ ID NO: 128 (gene encoding the L chain CDR2 described above in (5-1)), or a degenerate codon engineered form of the L chain CDR2 gene; and a L chain CDR3 gene consisting of nucleotide residues 283 to 309 of the L chain V region gene consisting of the nucleotide sequence represented by SEQ ID NO: 128 (gene encoding the L chain CDR3 described above in (5-1)), or a degenerate codon engineered form of the L chain CDR3 gene, (6-1D) an antibody gene comprising: a H chain CDR1 gene consisting of nucleotide residues 91 to 105 of a H chain V region gene consisting of the nucleotide sequence represented by SEQ ID NO: 131 (gene encoding the H chain CDR1 described above in (6-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 131 (gene encoding the H chain CDR2 described above in (6-1)), or a degenerate codon engineered form of the H chain CDR2 gene; and a H chain CDR3 gene consisting of nucleotide residues 295 to 318 of the H chain V region gene consisting of the nucleotide sequence represented by SEQ ID NO: 131 (gene encoding the H chain CDR3 described above in (6-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 132 (gene encoding the L chain CDR1 described above in (6-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 132 (gene encoding the L chain CDR2 described above in (6-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 132 (gene encoding the L chain CDR3 described above in (6-1)), or a degenerate codon engineered form of the L chain CDR3 gene, (7-1D) an antibody gene comprising: a H chain CDR1 gene consisting of nucleotide residues 91 to 105 of a H chain V region gene consisting of the nucleotide sequence represented by SEQ ID NO: 135 (gene encoding the H chain CDR1 described above in (7-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 135 (gene encoding the H chain CDR2 described above in (7-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 135 (gene encoding the H chain CDR3 described above in (7-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 136 (gene encoding the L chain CDR1 described above in (7-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 136 (gene encoding the L chain CDR2 described above in (7-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 136 (gene encoding the L chain CDR3 described above in (7-1)), or a degenerate codon engineered form of the L chain CDR3 gene, (8-1D) an antibody gene comprising: a H chain CDR1 gene consisting of nucleotide residues 91 to 105 of a H chain V region gene consisting of the nucleotide sequence represented by SEQ ID NO: 139 (gene encoding the H chain CDR1 described above in (8-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 139 (gene encoding the H chain CDR2 described above in (8-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 139 (gene encoding the H chain CDR3 described above in (8-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 140 (gene encoding the L chain CDR1 described above in (8-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 140 (gene encoding the L chain CDR2 described above in (8-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 140 (gene encoding the L chain CDR3 described above in (8-1)), or a degenerate codon engineered form of the L chain CDR3 gene, (9-1D) an antibody gene comprising: a H chain CDR1 gene consisting of nucleotide residues 91 to 105 of a H chain V region gene consisting of the nucleotide sequence represented by SEQ ID NO: 143 (gene encoding the H chain CDR1 described above in (9-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 143 (gene encoding the H chain CDR2 described above in (9-1)), or a degenerate codon engineered form of the H chain CDR2 gene; and a H chain CDR3 gene consisting of nucleotide residues 298 to 330 of the H chain V region gene consisting of the nucleotide sequence represented by SEQ ID NO: 143 (gene encoding the H chain CDR3 described above in (9-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 144 (gene encoding the L chain CDR1 described above in (9-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 144 (gene encoding the L chain CDR2 described above in (9-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 144 (gene encoding the L chain CDR3 described above in (9-1)), or a degenerate codon engineered form of the L chain CDR3 gene, (10-1D) an antibody gene comprising: a H chain CDR1 gene consisting of nucleotide residues 91 to 105 of a H chain V region gene consisting of the nucleotide sequence represented by SEQ ID NO: 147 (gene encoding the H chain CDR1 described above in (10-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 147 (gene encoding the H chain CDR2 described above in (10-1)), or a degenerate codon engineered form of the H chain CDR2 gene; and a H chain CDR3 gene consisting of nucleotide residues 295 to 327 of the H chain V region gene consisting of the nucleotide sequence represented by SEQ ID NO: 147 (gene encoding the H chain CDR3 described above in (10-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 148 (gene encoding the L chain CDR1 described above in (10-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 148 (gene encoding the L chain CDR2 described above in (10-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 148 (gene encoding the L chain CDR3 described above in (10-1)), or a degenerate codon engineered form of the L chain CDR3 gene, and (11-1D) an antibody gene comprising: a H chain CDR1 gene consisting of nucleotide residues 91 to 105 of a H chain V region gene consisting of the nucleotide sequence represented by SEQ ID NO: 151 (gene encoding the H chain CDR1 described above in (11-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 151 (gene encoding the H chain CDR2 described above in (11-1)), or a degenerate codon engineered form of the H chain CDR2 gene; and a H chain CDR3 gene consisting of nucleotide residues 295 to 324 of the H chain V region consisting of the nucleotide sequence represented by SEQ ID NO: 151 (gene encoding the H chain CDR3 described above in (11-1)), or a degenerate codon engineered form of the H chain CDR3 gene.

Further examples of the present antibody gene can include (1-2D) an antibody gene comprising a H chain variable region gene consisting of a nucleotide sequence having at least 80% or higher sequence identity to the nucleotide sequence represented by SEQ ID NO: 111 (gene encoding a H chain variable region consisting of an amino acid sequence having at least 80% or higher sequence identity to the amino acid sequence represented by SEQ ID NO: 7), and a L chain variable region gene consisting of a nucleotide sequence having at least 80% or higher sequence identity to the nucleotide sequence represented by SEQ ID NO: 112 (gene encoding a L chain variable region consisting of an amino acid sequence having at least 80% or higher sequence identity to the amino acid sequence represented by SEQ ID NO: 8), (2-2D) an antibody gene comprising a H chain variable region gene consisting of a nucleotide sequence having at least 80% or higher sequence identity to the nucleotide sequence represented by SEQ ID NO: 115 (gene encoding a H chain variable region consisting of an amino acid sequence having at least 80% or higher sequence identity to the amino acid sequence represented by SEQ ID NO: 17), and a L chain variable region gene consisting of a nucleotide sequence having at least 80% or higher sequence identity to the nucleotide sequence represented by SEQ ID NO: 116 (gene encoding a L chain variable region consisting of an amino acid sequence having at least 80% or higher sequence identity to the amino acid sequence represented by SEQ ID NO: 18), (3-2D) an antibody gene comprising a H chain variable region gene consisting of a nucleotide sequence having at least 80% or higher sequence identity to the nucleotide sequence represented by SEQ ID NO: 119 (gene encoding a H chain variable region consisting of an amino acid sequence having at least 80% or higher sequence identity to the amino acid sequence represented by SEQ ID NO: 27), and a L chain variable region gene consisting of a nucleotide sequence having at least 80% or higher sequence identity to the nucleotide sequence represented by SEQ ID NO: 120 (gene encoding a L chain variable region consisting of an amino acid sequence having at least 80% or higher sequence identity to the amino acid sequence represented by SEQ ID NO: 28), (4-2D) an antibody gene comprising a H chain variable region gene consisting of a nucleotide sequence having at least 80% or higher sequence identity to the nucleotide sequence represented by SEQ ID NO: 123 (gene encoding a H chain variable region consisting of an amino acid sequence having at least 80% or higher sequence identity to the amino acid sequence represented by SEQ ID NO: 37), and a L chain variable region gene consisting of a nucleotide sequence having at least 80% or higher sequence identity to the nucleotide sequence represented by SEQ ID NO: 124 (gene encoding a L chain variable region consisting of an amino acid sequence having at least 80% or higher sequence identity to the amino acid sequence represented by SEQ ID NO: 38), (5-2D) an antibody gene comprising a H chain variable region gene consisting of a nucleotide sequence having at least 80% or higher sequence identity to the nucleotide sequence represented by SEQ ID NO: 127 (gene encoding a H chain variable region consisting of an amino acid sequence having at least 80% or higher sequence identity to the amino acid sequence represented by SEQ ID NO: 47), and a L chain variable region gene consisting of a nucleotide sequence having at least 80% or higher sequence identity to the nucleotide sequence represented by SEQ ID NO: 128 (gene encoding a L chain variable region consisting of an amino acid sequence having at least 80% or higher sequence identity to the amino acid sequence represented by SEQ ID NO: 48), (6-2D) an antibody gene comprising a H chain variable region gene consisting of a nucleotide sequence having at least 80% or higher sequence identity to the nucleotide sequence represented by SEQ ID NO: 131 (gene encoding a H chain variable region consisting of an amino acid sequence having at least 80% or higher sequence identity to the amino acid sequence represented by SEQ ID NO: 57), and a L chain variable region gene consisting of a nucleotide sequence having at least 80% or higher sequence identity to the nucleotide sequence represented by SEQ ID NO: 132 (gene encoding a L chain variable region consisting of an amino acid sequence having at least 80% or higher sequence identity to the amino acid sequence represented by SEQ ID NO: 58), (7-2D) an antibody gene comprising a H chain variable region gene consisting of a nucleotide sequence having at least 80% or higher sequence identity to the nucleotide sequence represented by SEQ ID NO: 135 (gene encoding a H chain variable region consisting of an amino acid sequence having at least 80% or higher sequence identity to the amino acid sequence represented by SEQ ID NO: 67), and a L chain variable region gene consisting of a nucleotide sequence having at least 80% or higher sequence identity to the nucleotide sequence represented by SEQ ID NO: 136 (gene encoding a L chain variable region consisting of an amino acid sequence having at least 80% or higher sequence identity to the amino acid sequence represented by SEQ ID NO: 68), (8-2D) an antibody gene comprising a H chain variable region gene consisting of a nucleotide sequence having at least 80% or higher sequence identity to the nucleotide sequence represented by SEQ ID NO: 139 (gene encoding a H chain variable region consisting of an amino acid sequence having at least 80% or higher sequence identity to the amino acid sequence represented by SEQ ID NO: 77), and a L chain variable region gene consisting of a nucleotide sequence having at least 80% or higher sequence identity to the nucleotide sequence represented by SEQ ID NO: 140 (gene encoding a L chain variable region consisting of an amino acid sequence having at least 80% or higher sequence identity to the amino acid sequence represented by SEQ ID NO: 78), (9-2D) an antibody gene comprising a H chain variable region gene consisting of a nucleotide sequence having at least 80% or higher sequence identity to the nucleotide sequence represented by SEQ ID NO: 143 (gene encoding a H chain variable region consisting of an amino acid sequence having at least 80% or higher sequence identity to the amino acid sequence represented by SEQ ID NO: 87), and a L chain variable region gene consisting of a nucleotide sequence having at least 80% or higher sequence identity to the nucleotide sequence represented by SEQ ID NO: 144 (gene encoding a L chain variable region consisting of an amino acid sequence having at least 80% or higher sequence identity to the amino acid sequence represented by SEQ ID NO: 88), (10-2D) an antibody gene comprising a H chain variable region gene consisting of a nucleotide sequence having at least 80% or higher sequence identity to the nucleotide sequence represented by SEQ ID NO: 147 (gene encoding a H chain variable region consisting of an amino acid sequence having at least 80% or higher sequence identity to the amino acid sequence represented by SEQ ID NO: 97), and a L chain variable region gene consisting of a nucleotide sequence having at least 80% or higher sequence identity to the nucleotide sequence represented by SEQ ID NO: 148 (gene encoding a L chain variable region consisting of an amino acid sequence having at least 80% or higher sequence identity to the amino acid sequence represented by SEQ ID NO: 98), and (11-2D) an antibody gene comprising a H chain variable region gene consisting of a nucleotide sequence having at least 80% or higher sequence identity to the nucleotide sequence represented by SEQ ID NO: 151 (gene encoding a H chain variable region consisting of an amino acid sequence having at least 80% or higher sequence identity to the amino acid sequence represented by SEQ ID NO: 107), and a L chain variable region gene consisting of a nucleotide sequence having at least 80% or higher sequence identity to the nucleotide sequence represented by SEQ ID NO: 152 (gene encoding a L chain variable region consisting of an amino acid sequence having at least 80% or higher sequence identity to the amino acid sequence represented by SEQ ID NO: 108).

Particularly, examples of the present antibody gene can specifically include (1-4D) an antibody gene comprising a H chain gene consisting of a nucleotide sequence having at least 80% or higher sequence identity to the nucleotide sequence represented by SEQ ID NO: 113 (gene encoding a H chain consisting of an amino acid sequence having at least 80% or higher sequence identity to the amino acid sequence represented by SEQ ID NO: 9), and a L chain gene consisting of a nucleotide sequence having at least 80% or higher sequence identity to the nucleotide sequence represented by SEQ ID NO: 114 (gene encoding a L chain consisting of an amino acid sequence having at least 80% or higher sequence identity to the amino acid sequence represented by SEQ ID NO: 10), (2-4D) an antibody gene comprising a H chain gene consisting of a nucleotide sequence having at least 80% or higher sequence identity to the nucleotide sequence represented by SEQ ID NO: 117 (gene encoding a H chain consisting of an amino acid sequence having at least 80% or higher sequence identity to the amino acid sequence represented by SEQ ID NO: 19), and a L chain gene consisting of a nucleotide sequence having at least 80% or higher sequence identity to the nucleotide sequence represented by SEQ ID NO: 118 (gene encoding a L chain consisting of an amino acid sequence having at least 80% or higher sequence identity to the amino acid sequence represented by SEQ ID NO: 20), (3-4D) an antibody gene comprising a H chain gene consisting of a nucleotide sequence having at least 80% or higher sequence identity to the nucleotide sequence represented by SEQ ID NO: 121 (gene encoding a H chain consisting of an amino acid sequence having at least 80% or higher sequence identity to the amino acid sequence represented by SEQ ID NO: 29), and a L chain gene consisting of a nucleotide sequence having at least 80% or higher sequence identity to the nucleotide sequence represented by SEQ ID NO: 122 (gene encoding a L chain consisting of an amino acid sequence having at least 80% or higher sequence identity to the amino acid sequence represented by SEQ ID NO: 30), (4-4D) an antibody gene comprising a H chain gene consisting of a nucleotide sequence having at least 80% or higher sequence identity to the nucleotide sequence represented by SEQ ID NO: 125 (gene encoding a H chain consisting of an amino acid sequence having at least 80% or higher sequence identity to the amino acid sequence represented by SEQ ID NO: 39), and a L chain gene consisting of a nucleotide sequence having at least 80% or higher sequence identity to the nucleotide sequence represented by SEQ ID NO: 126 (gene encoding a L chain consisting of an amino acid sequence having at least 80% or higher sequence identity to the amino acid sequence represented by SEQ ID NO: 40), (5-4D) an antibody gene comprising a H chain gene consisting of a nucleotide sequence having at least 80% or higher sequence identity to the nucleotide sequence represented by SEQ ID NO: 129 (gene encoding a H chain consisting of an amino acid sequence having at least 80% or higher sequence identity to the amino acid sequence represented by SEQ ID NO: 49), and a L chain gene consisting of a nucleotide sequence having at least 80% or higher sequence identity to the nucleotide sequence represented by SEQ ID NO: 130 (gene encoding a L chain consisting of an amino acid sequence having at least 80% or higher sequence identity to the amino acid sequence represented by SEQ ID NO: 50), (6-4D) an antibody gene comprising a H chain gene consisting of a nucleotide sequence having at least 80% or higher sequence identity to the nucleotide sequence represented by SEQ ID NO: 133 (gene encoding a H chain consisting of an amino acid sequence having at least 80% or higher sequence identity to the amino acid sequence represented by SEQ ID NO: 59), and a L chain gene consisting of a nucleotide sequence having at least 80% or higher sequence identity to the nucleotide sequence represented by SEQ ID NO: 134 (gene encoding a L chain consisting of an amino acid sequence having at least 80% or higher sequence identity to the amino acid sequence represented by SEQ ID NO: 60), (7-4D) an antibody gene comprising a H chain gene consisting of a nucleotide sequence having at least 80% or higher sequence identity to the nucleotide sequence represented by SEQ ID NO: 137 (gene encoding a H chain consisting of an amino acid sequence having at least 80% or higher sequence identity to the amino acid sequence represented by SEQ ID NO: 69), and a L chain gene consisting of a nucleotide sequence having at least 80% or higher sequence identity to the nucleotide sequence represented by SEQ ID NO: 138 (gene encoding a L chain consisting of an amino acid sequence having at least 80% or higher sequence identity to the amino acid sequence represented by SEQ ID NO: 70), (8-4D) an antibody gene comprising a H chain gene consisting of a nucleotide sequence having at least 80% or higher sequence identity to the nucleotide sequence represented by SEQ ID NO: 141 (gene encoding a H chain consisting of an amino acid sequence having at least 80% or higher sequence identity to the amino acid sequence represented by SEQ ID NO: 79), and a L chain gene consisting of a nucleotide sequence having at least 80% or higher sequence identity to the nucleotide sequence represented by SEQ ID NO: 142 (gene encoding a L chain consisting of an amino acid sequence having at least 80% or higher sequence identity to the amino acid sequence represented by SEQ ID NO: 80), (9-4D) an antibody gene comprising a H chain gene consisting of a nucleotide sequence having at least 80% or higher sequence identity to the nucleotide sequence represented by SEQ ID NO: 145 (gene encoding a H chain consisting of an amino acid sequence having at least 80% or higher sequence identity to the amino acid sequence represented by SEQ ID NO: 89), and a L chain gene consisting of a nucleotide sequence having at least 80% or higher sequence identity to the nucleotide sequence represented by SEQ ID NO: 146 (gene encoding a L chain consisting of an amino acid sequence having at least 80% or higher sequence identity to the amino acid sequence represented by SEQ ID NO: 90), (10-4D) an antibody gene comprising a H chain gene consisting of a nucleotide sequence having at least 80% or higher sequence identity to the nucleotide sequence represented by SEQ ID NO: 149 (gene encoding a H chain consisting of an amino acid sequence having at least 80% or higher sequence identity to the amino acid sequence represented by SEQ ID NO: 99), and a L chain gene consisting of a nucleotide sequence having at least 80% or higher sequence identity to the nucleotide sequence represented by SEQ ID NO: 150 (gene encoding a L chain consisting of an amino acid sequence having at least 80% or higher sequence identity to the amino acid sequence represented by SEQ ID NO: 100), and (11-4D) an antibody gene comprising a H chain gene consisting of a nucleotide sequence having at least 80% or higher sequence identity to the nucleotide sequence represented by SEQ ID NO: 153 (gene encoding a H chain consisting of an amino acid sequence having at least 80% or higher sequence identity to the amino acid sequence represented by SEQ ID NO: 109), and a L chain gene consisting of a nucleotide sequence having at least 80% or higher sequence identity to the nucleotide sequence represented by SEQ ID NO: 154 (gene encoding a L chain consisting of an amino acid sequence having at least 80% or higher sequence identity to the amino acid sequence represented by SEQ ID NO: 110).

The present CAR gene is not particularly limited as long as the gene (nucleotide) encodes the present CAR. Examples thereof can specifically include (1-3D) a CAR gene comprising a gene encoding the single chain antibody described above in (1-3), or a degenerate codon engineered form of the gene, (2-3D) a CAR gene comprising a gene encoding the single chain antibody described above in (2-3), or a degenerate codon engineered form of the gene, (3-3D) a CAR gene comprising a gene encoding the single chain antibody described above in (3-3), or a degenerate codon engineered form of the gene, (4-3D) a CAR gene comprising a gene encoding the single chain antibody described above in (4-3), or a degenerate codon engineered form of the gene, (5-3D) a CAR gene comprising a gene encoding the single chain antibody described above in (5-3), or a degenerate codon engineered form of the gene, (6-3D) a CAR gene comprising a gene encoding the single chain antibody described above in (6-3), or a degenerate codon engineered form of the gene, (7-3D) a CAR gene comprising a gene encoding the single chain antibody described above in (7-3), or a degenerate codon engineered form of the gene, (8-3D) a CAR gene comprising a gene encoding the single chain antibody described above in (8-3), or a degenerate codon engineered form of the gene, (9-3D) a CAR gene comprising a gene encoding the single chain antibody described above in (9-3), or a degenerate codon engineered form of the gene,
(10-3D) a CAR gene comprising a gene encoding the single chain antibody described above in (10-3), or a degenerate codon engineered form of the gene,
(11-3D) a CAR gene comprising a gene encoding the single chain antibody described above in (11-3), or a degenerate codon engineered form of the gene,
(1-3'-1D) a CAR gene comprising a gene encoding the single chain antibody described above in (1-3'-1), or a degenerate codon engineered form of the gene,
(1-3'-2D) a CAR gene comprising a gene encoding the single chain antibody described above in (1-3'-2), or a degenerate codon engineered form of the gene,
(1-3'-3D) a CAR gene comprising a gene encoding the single chain antibody described above in (1-3'-3), or a degenerate codon engineered form of the gene,
(2-3'-1D) a CAR gene comprising a gene encoding the single chain antibody described above in (2-3'-1), or a degenerate codon engineered form of the gene,
(2-3'-2D) a CAR gene comprising a gene encoding the single chain antibody described above in (2-3'-2), or a degenerate codon engineered form of the gene,
(2-3'-3D) a CAR gene comprising a gene encoding the single chain antibody described above in (2-3'-3), or a degenerate codon engineered form of the gene, and
(2-3'-4D) a CAR gene comprising a gene encoding the single chain antibody described above in (2-3'-4), or a degenerate codon engineered form of the gene.

In the present specification, the phrase "at least 80% or higher identity" means that the identity is 80% or higher, preferably 85% or higher, more preferably 88% or higher, further preferably 90% or higher, still further preferably 93% or higher, particularly preferably 95% or higher, particularly more preferably 98% or higher, most preferably 100%.

In the present specification, the term "identity" means the degree of similarity between polypeptide or polynucleotide sequences (this degree is determined by matching a query sequence to another sequence, preferably of the same type (nucleic acid or protein sequence) Examples of a preferred computer program method for calculating and determining the "identity" include, but are not limited to, GCG BLAST (Basic Local Alignment Search Tool) (Altschul et al., J. Mol. Biol. 1990, 215: 403-410; Altschul et al., Nucleic Acids Res. 1997, 25: 3389-3402; and Devereux et al., Nucleic Acid Res. 1984, 12: 387), BLASTN 2.0 (Gish W., 1996-2002), FASTA (Pearson and Lipman, Proc. Natl. Acad. Sci. USA 1988, 85: 2444-2448), and GCG GelMerge which determines and aligns a pair of the longest overlapping contigs (Wibur and Lipman, SIAM J. Appl. Math. 1984, 44: 557-567; and Needleman and Wunsch, J. Mol. Biol. 1970, 48: 443-453).

In the present specification, the "amino acid sequence having at least 80% or higher sequence identity to the amino acid sequence represented by SEQ ID NO: X" is, in other words, an "amino acid sequence derived from the amino acid sequence represented by SEQ ID NO: X by the deletion, substitution, insertion, and/or addition of 0, 1 or several amino acid residues" and has functions equivalent to those of the amino acid sequence represented by SEQ ID NO: X. In this context, the "amino acid sequence derived by the deletion, substitution, insertion, and/or addition of 1 or several amino acid residues" means an amino acid sequence in which amino acid residues have been deleted, substituted, inserted, and/or added, for example, within the range of 1 to 30 residues, preferably within the range of 1 to 20 residues, more preferably within the range of 1 to 15 residues, further preferably within the range of 1 to 10 residues, further preferably within the range of 1 to 5 residues, further preferably within the range of 1 to 3 residues, further preferably within the range of 1 or 2 residues. The mutation treatment of these amino acid residues can be performed by an arbitrary method known to those skilled in the art such as chemical synthesis, a gene engineering approach, or mutagenesis.

The promoter in the present vector can be any region that starts the transcription of mRNA encoded by the present antibody gene located downstream of the promoter. The promoter usually comprises a transcription start site (TSS).

The type of the promoter or the vector in the present vector can be appropriately selected according to the type of a host cell (or a host organism) to which the present vector is introduced.

The host cell can express the present antibody by the transcription of the present antibody gene, or can express the present CAR by the transcription of mRNA of the present CAR gene. In the case of introducing a "vector comprising the present antibody gene" as the present vector, a yeast, a mammalian cell, an insect cell, or a plant cell given below can be used as the host cell. In the case of introducing a "vector comprising the present CAR gene" as the present vector, the immunocompetent cell described above can be used as the host cell.

In the case of using a yeast (e.g., *Saccharomyces cerevisiae* and *Schizosaccharomyces pombe*) as the host cell, examples of the present vector can include a vector such as YEP13 (ATCC37115), YEp24 (ATCC37051), and YCp50 (ATCC37419), and a vector derived from the vector. Examples of the promoter can include glycolysis gene (e.g., hexose kinase gene) promoter, PHO5 promoter, PGK promoter, GAP promoter, ADH promoter, gal1 promoter, gal10 promoter, heat shock protein promoter, MFα1 promoter, and CUP1 promoter.

In the case of using a mammalian cell (e.g., a human-derived Namalwa cell, a monkey-derived COS cell, a Chinese hamster ovary-derived CHO cell, and a human- or mouse-derived T cell) as the host cell and using a vector comprising the antibody gene as the present vector, examples of the present vector can include a vector such as pcDNAI, pcDM8 (manufactured by Funakoshi Co., Ltd.), pAGE107 (Japanese unexamined Patent Application Publication No. 3-22979; and Cytotechnology, 3, 133, (1990)), pAS3-3 (Japanese unexamined Patent Application Publication No. 2-227075), pCDM8 (Nature, 329, 840, (1987)), pcDNAI/Amp (manufactured by Invitrogen Corp.), pREP4 (manufactured by Invitrogen Corp.), pAGE103 (J. Biochemistry, 101, 1307 (1987)), and pAGE210, and a vector derived from the vector. On the other hand, in the case of using a mammalian cell (e.g., the human-derived immunocompetent cell described above) as the host cell and using a vector comprising the CAR gene as the present vector, examples of the present vector can include a retrovirus vector such as a pMSGV vector (Tamada k et al., Clin Cancer Res 18: 6436-6445 (2002)) and a pMSCV vector (manufactured by Takara Bio Inc.), and a vector derived from the vector.

Examples of the promoter in the present vector can include cytomegalovirus (CMV) IE (immediate early) gene promoter, SV40 early promoter, retrovirus promoter, metallothionein promoter, heat shock promoter, SRα promoter, NFAT promoter, and HIF promoter.

In the case of using an insect cell (e.g., a Sf9 cell and a Sf21 cell which are *Spodoptera frugiperda* ovarian cells, and a High5 cell which is a *Trichoplusia ni* ovarian cell) as the host cell, examples of the present vector can include a transfer vector for use in recombinant baculovirus preparation methods, specifically, a vector such as pVL1392, pVL1393, and pBlueBacIII (all manufactured by Invitrogen Corp.), and a vector derived from the vector. Examples of the promoter can include polyhedrin promoter and p10 promoter.

In the case of using a plant cell (e.g., tobacco, potato, tomato, carrot, soybean, rapeseed, alfalfa, rice, wheat, and barley cells) as the host cell, examples of the expression vector can include a vector such as Ti plasmid and tobacco mosaic virus vector, and a vector derived from the vector. Examples of the promoter can include cauliflower mosaic virus (CaMV) 35S promoter and rice actin 1 promoter.

The present vector preferably further comprises the nucleotide sequences of an enhancer region and a ribosome binding site (RBS) for further enhancing gene expression efficiency, and further comprises a drug resistance gene (e.g., spectinomycin resistance gene, chloramphenicol resistance gene, tetracycline resistance gene, kanamycin resistance gene, ampicillin resistance gene, puromycin resistance gene, hygromycin resistance gene, blasticidin resistance gene, and geneticin resistance gene) appropriate for the type of the host cell for screening for the present host cell. The enhancer region is usually arranged upstream of the promoter, and RBS is usually arranged between the promoter and the present gene. The nucleotide sequence of the present antibody gene to be incorporated into the present vector may be subjected to the optimization of a codon sequence according to the host cell for expression. The present vector can be prepared by a method known in the art using a gene recombination technique.

The present host cell can be obtained by introducing the present vector to the host cell (transfecting the host cell therewith) by a method appropriate for the type of the host cell.

In the case of using the yeast described above as the host cell, the method for introducing the present vector to the yeast can be any method for introducing DNA to the yeast. Examples thereof can include a method such as electroporation (Methods Enzymol., 194, 182 (1990)), spheroplast method (Proc. Natl. Acad. Sci. U.S.A, 84, 1929 (1978)), and lithium acetate method (J. Bacteriology, 153, 163 (1983)).

In the case of using the mammalian cell described above as the host cell, the method for introducing the present vector to the mammalian cell can be any method for introducing DNA to the mammalian cell. Examples thereof can include a method such as electroporation (Cytotechnology, 3, 133 (1990)), calcium phosphate method (Japanese unexamined Patent Application Publication No. 2-227075), lipofection (Proc. Natl. Acad. Sci. U.S.A., 84, 7413 (1987)), and viral infection method, as mentioned above. Examples of such a viral infection method can include a method which involves transfecting a packaging cell such as a GP2-293 cell (manufactured by Takara Bio Inc.), a Plat-GP cell (manufactured by Cosmo Bio Co., Ltd.), a PG13 cell (ATCC CRL-10686), or a PA317 cell (ATCC CRL-9078) with a CAR expression vector (International Publication No. WO 2016/056228) and a packaging plasmid to prepare a recombinant virus, and infecting a T cell with the recombinant virus, as mentioned above.

In the case of using the insect cell described above as the host cell, examples of the method for introducing the present vector to the insect cell can include a method which involves cotransfecting the insect cell with the present vector (transfer vector) and baculovirus-derived genomic DNA to prepare a recombinant baculovirus, according to a method described in "Current Protocols in Molecular Biology", "Baculovirus Expression Vectors, A Laboratory Manual, W. H. Freeman and Company, New York (1992)", "Bio/Technology, 6, 47 (1988)", etc. Examples of such a cotransfection method can include a method such as calcium phosphate method (Japanese unexamined Patent Application Publication No. 2-227075) and lipofection (Proc. Natl. Acad. Sci. U.S.A., 84, 7413 (1987).

In the case of using the plant cell described above as the host cell, examples of the method for introducing the present vector to the plant cell can include a method such as a method using *Agrobacterium* (Japanese unexamined Patent Application Publication Nos. 59-140885 and 60-70080), electroporation (Japanese unexamined Patent Application Publication No. 60-251887), and a method using a particle gun (gene gun) (Japanese Patent Nos. 2606856 and 2517813).

The present antibody can be obtained by culturing the present host cell obtained by the method mentioned above in a culture solution appropriate for the host cell.

A transgenic animal, such as a mouse, cattle, a goat, sheep, a chicken, or a pig, in which the present antibody gene (the present vector) has been incorporated is prepared by use of a transgenic animal preparation technique, and an antibody derived from the present antibody gene can also be produced in a large amount from the blood, milk, or the like of the transgenic animal.

Nonhuman animals (e.g., mice and rats) are immunized with a substance comprising a human-derived GPC3 polypeptide consisting of the amino acid sequence represented by SEQ ID NO: 155 (GPC3 polypeptide antigen). A phage library of scFv genes is prepared by a phage display method. The present scFv can be obtained by a biopanning method using the GPC3 polypeptide antigen and/or a cell line expressing the GPC3 polypeptide antigen (preferably a cell line expressing no endogenous GPC3), and further, preferably, a competitor C-terminal polypeptide of GPC3 consisting of the amino acid sequence represented by SEQ ID NO: 159. From the nonhuman animals thus immunized with the antigen, antibody-producing hybridomas are prepared by use of a cell fusion technique. A culture supernatant containing the present antibody can also be obtained through screening by ELISA using a plate in which the antigen has been immobilized on a solid phase. The present antibody can be separated and purified from the culture supernatant by use of an antibody purification technique known in the art.

The present detection method can be any method comprising the step of detecting GPC3 localized on a cell membrane (anchored on a cell membrane) in a sample (e.g., blood, a tissue, and urine) using the present antibody. Specific examples of the detection method can include immunofluorescent staining, Western blotting, and ELISA using the present antibody.

The present kit for detection is a kit comprising the present antibody or a labeled form thereof and is limited by the purpose of "detecting GPC3". The kit usually comprises components generally used in this kind of kit, for example, a carrier, a pH buffering agent, and a stabilizer as well as an attached document such as a manual and an instruction for detecting GPC3.

The organism species of GPC3 to be detected in the present detection method or the present kit for detection may be a nonhuman animal such as a mouse or a rat and is usually a human.

Examples of the labeling material for the labeled form of the present antibody can include: an enzyme such as peroxidase (e.g., horseradish peroxidase [HRP]), alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase and acetylcholinesterase; a fluorescent material such as fluorescein isothiocyanate, phycobiliprotein, rare earth metal chelates, dansyl chloride and tetramethylrhodamine isothiocyanate; a fluorescence protein such as green fluorescence protein (GFP), cyan fluorescence protein (CFP), blue fluorescence protein (BFP), yellow fluorescence protein (YFP), red fluorescence protein (RFP) and luciferase; a radioisotope such as $^3$H, $^{14}$C, $^{125}$I and $^{131}$I; biotin; avidin; and a chemiluminescence material.

References, such as scientific literatures, patents, and patent applications, cited herein are incorporated herein by reference in their entirety to the same extent as if each individual reference was specifically described. The present application claims the priority based on Japanese Patent Application No. 2017-001732 (filed on Jan. 10, 2017), the contents of which are incorporated herein by reference in their entirety.

Hereinafter, the present invention will be described more specifically with reference to Examples. However, the technical scope of the present invention is not limited by these examples.

Example 1

1. Preparation of Novel Anti-GPC3 Antibody Recognizing N-Terminal Polypeptide of Human GPC3

SUMMARY

SKG/Jcl mice were used as animals to be immunized for preparing an anti-human GPC3 antibody, and full-length human GPC3 protein was used as an immunizing antigen. The SKG/Jcl mice were autoimmune disease model mice that spontaneously develop rheumatoid arthritis and are known to produce antibodies in response even to self-components depending on aging or a rearing environment. Meanwhile, GPC3 is highly homologous between humans and mice and is usually less likely to cause antibody production even by the immunization of normal mice. Therefore, the SKG/Jcl mice were used as animals to be immunized. A scFv phage library was prepared from cDNA derived from B cells of the mice immunized with GPC3, and an anti-human GPC3 antibody was isolated by the application of the phage display method.

Although the antiserum of immunized mice contains many types of antibodies, it is necessary to select mice producing antibodies having specificity for the N-terminal polypeptide of GPC3 by excluding mice producing antibodies low specific for GPC3 or antibodies recognizing the C-terminal polypeptide of GPC3. Accordingly, mouse individuals that exhibited the production of an antibody specifically binding to the N-terminal polypeptide of GPC3 were selected by use of ELISA and FCM. Specifically, cDNA was synthesized by reverse transcription reaction from total RNA of the B cells derived from the immunized mice, and antibody genes were amplified to prepare an antibody gene library. A scFv phage library was constructed from the antibody gene library, and E. coli was infected with the library so that E. coli expressed scFv, followed by biopanning using recombinant GPC3, the GPC3-expressing cell line, and the C-terminal polypeptide of GPC3 to enrich phages expressing the target scFv, i.e., an antibody against the N-terminal polypeptide of GPC3. In order to further analyze the obtained scFv for binding specificity for GPC3 in cells, i.e., GPC3 localized on (bound to) a cell membrane (membrane-bound GPC3) via a GPI (glycosylphosphatidylinositol) anchor, verification was made by use of cell based-ELISA and FCM. Furthermore, the nucleotide sequences of H chain and L chain variable regions of clones having binding specificity were sequenced, and the nucleotide sequences of the anti-GPC3 antibodies produced by the B cells derived from the immunized mice were determined on the basis of these sequences. Finally, the mammalian display method which involved expressing the N-terminal polypeptide fragment and the C-terminal polypeptide fragment of GPC3 on cell surface was used to confirm that the epitope for the scFv was the N-terminal polypeptide fragment of GPC3. Hereinafter, detailed methods and results will be shown.

1-1 Material and Method

[Cell Culture]

A JHH7 cell line, a HepG2 cell line, and a SK-Hep-1 cell line forced to express full-length human GPC3 (hereinafter, also referred to as a "GPC3-expressing cell line") were used as human GPC3-expressing cells to perform the biopanning and screening of an anti-GPC3 antibody. The JHH7 cell line is a GPC3-expressing cell line derived from hepatocellular carcinoma, and the cells constitutively express GPC3 bound to a cell membrane (membrane-bound GPC3) via a GPI (glycosylphosphatidylinositol) anchor. On the other hand, the HepG2 cell line is a GPC3-expressing cell line derived from hepatocellular carcinoma, as in the JHH7 cell line, but is a cell line in which the expression of secretory GPC3 that is not bound to a cell membrane is dominant over membrane-bound GPC3. The Sk-Hep-1 cell line is a hepatocellular carcinoma-derived cell line expressing no GPC3. Hence, a cell line expressing only membrane-bound full-length GPC3 or membrane-bound GPC3 having a partial length deficient in a portion of exons can be prepared by forced expression.

The culture of 4 types of cell lines (JHH7 cell line, HepG2 cell line, GPC3-expressing cell line, and human embryonic kidney epithelium-derived 293T cell line) was performed under conditions of 37° C. and 5% CO 2 in a DMEM culture solution (manufactured by Sigma-Aldrich Co. LLC) containing 10% FBS (manufactured by Gibco/Thermo Fisher Scientific Inc.) and 1% penicillin-streptomycin (manufactured by Gibco/Thermo Fisher Scientific Inc.) (hereinafter, simply referred to as a "DMEM culture solution"). The culture of a CHO-K1 cell line was performed under conditions of 37° C. and 5% CO 2 in a Ham's F12 culture solution (manufactured by Sigma-Aldrich Co. LLC) containing 10% FBS (manufactured by Gibco/Thermo Fisher Scientific Inc.).

[Immunizing Antigen]

C-terminally 6×His-tagged (SEQ ID NO: 190) recombinant GPC3 (manufactured by R & D Systems Inc.) was adjusted to 0.1 mg/mL with PBS and mixed with an artificial adjuvant TiterMax Gold (manufactured by TiterMax USA, Inc.) or CFA (Freund's Adjuvant Complete) (F5881, manufactured by Sigma-Aldrich Co. LLC) in equal amounts to prepare an emulsion, which was then used as an initial immunizing antigen. Recombinant GPC3 was adjusted to a concentration from 10 to 100 µg/mL with PBS and used as the second or later immunizing antigens.

[Preparation of GPC3-Expressing Cell Line]

A gene encoding full-length human GPC3 consisting of the amino acid sequence represented by SEQ ID NO: 157 (full-length human GPC3 gene consisting of the nucleotide sequence represented by SEQ ID NO: 160) was inserted to a pcDNA3.1 vector (manufactured by Thermo Fisher Scientific Inc.) to prepare a GPC3 expression vector. A SK-Hep-1 cell line was transfected with the GPC3 expression vector according to a standard method and then cultured in a DMEM culture solution containing G418 (manufactured by Roche Diagnostics K.K.) to establish a SK-Hep-1 cell line stably expressing full-length GPC3 (GPC3-expressing cell line).

[Immunization of Mouse]

SKG/Jcl mice (CLEA Japan, Inc., 8-week-old female, SPF) were used as animals to be immunized, and immunized through footpads with recombinant GPC3 a total of 4 times on 1-week intervals. On 5 weeks from the start of immunization, blood was collected, and serum was prepared according to a standard method and used as a specimen for the confirmation of an antibody titer.

[Serum Antibody Titer of Antiserum Using ELISA]

In order to confirm the response of the immunized mice to produce an anti-GPC3 antibody, a serum antibody titer was measured by use of antigen-immobilized ELISA. 0.5 or 2 µg/mL recombinant GPC3 was added at 50 µL/well to a 96-well microplate (manufactured by Nalge Nunc International), and the plate was incubated at room temperature for 1 hour or at 4° C. for 12 hours. Then, 2% Block ACE (manufactured by DS Pharma Biomedical Co., Ltd.) was added at 200 µL/well to perform blocking treatment. The serum derived from the GPC3-immunized mice was serially diluted from 100-fold to 16500-fold with 0.1% Block ACE/PBS solution. Each diluted serum sample was added at 50 µL/well, and the plate was incubated at room temperature for 2 hours to perform antigen-antibody reaction treatment. After washing of the wells with a Tween 20-containing PBS (PBST) solution, goat anti-mouse IgG (manufactured by Jackson ImmunoResearch Laboratories Inc.) conjugated with 2 µg/mL peroxidase was added thereto, and the plate was incubated at room temperature for 2 hours to perform secondary antibody reaction treatment. After washing of the well five times with a PBST solution, moisture was removed, and a TMB substrate (manufactured by Thermo Fisher Scientific Inc.) was then added at 50 µL/well to perform color reaction. 15 minutes later, the color reaction was terminated by the addition of 0.18 M sulfuric acid at 50 µL/well, followed by the measurement of absorbance at 450 nm and 540 nm using a plate reader (manufactured by Bio-Rad Laboratories, Inc.). Quantification was performed using a corrected value obtained by subtracting the measurement value of 540 nm from the measurement value of 450 nm.

[Specificity of Antibody in Antiserum Using FCM]

In order to further confirm the specific binding activity of the antiserum against membrane-bound GPC3 as to the immunized mice, the mouse serum diluted 100-fold and $5\times10^3$ cells of the GPC3-expressing cell line were mixed and incubated for 30 minutes on ice. A FACS buffer (1% BSA/PBS solution) was added thereto, and the mixture was centrifuged to remove a supernatant. Then, 100 µL of 1 µg/mL goat anti-mouse IgG (H+L) Alexa Fluor 488 (manufactured by Thermo Fisher Scientific Inc.) was added as a secondary antibody, and the mixture was incubated for 30 minutes on ice to perform secondary antibody reaction treatment. The detection of Alexa Fluor 488 and the measurement of a fluorescence level were performed using a flow cytometer (FACSCanto) (manufactured by BD Biosciences).

[Preparation of scFv Phage Library]

B cells-derived total RNA was extracted according to a standard method as to the mice shown to produce an antibody binding to membrane-bound GPC3 by the method described above in the section [Flow cytometer]. RT-PCR with the total RNA as a template was performed according to a standard method to prepare cDNA. Antibody H chain and L chain variable region genes were amplified by PCR. A nucleotide sequence encoding a fusion protein of scFv having the H chain and L chain variable regions linked via a flexible linker, and coat protein g3p (cp3) of fibrous bacteriophage M13 was inserted to the multicloning site of a pTZ19R phagemid vector to prepare a scFv expression vector. The scFv library size was calculated from the transformation efficiency of an *E. coli* DH12S strain (manufactured by Invitrogen Corp.). The transformed DH12S strain was infected with a helper phage M13K07 (manufactured by Invitrogen Corp.) to prepare a phage library expressing scFv.

[Biopanning and Cloning of Phage scFv]

The biopanning of phage scFv using a combination of recombinant GPC3 immobilized on Dynabeads His-Tag (SEQ ID NO: 190) Isolation & Pulldown magnetic beads (manufactured by VERITAS Corp.) via 6×His tag, and the GPC3-expressing cell line as a bait was performed according to the method described in a document such as "J Mol Biol. 1991 Dec. 5; 222 (3): 581-97", "J Med Virol. 2007 June; 79 (6): 852-62", "Proc Natl Acad Sci USA. 2008 May 20; 105 (20): 7287-92", or "JOURNAL OF VIROLOGY, April 2004, p. 3325-3332 Vol. 78, No. 7". In each round (step) of biopanning consisting of types of series (A to E series) (see FIG. 1), an aliquot of polyclonal phage antibodies was sampled. In order to confirm the binding specificity of scFv, antigen-immobilized ELISA was performed according to the method described above in the section [Serum antibody titer of antiserum using ELISA] (method using the culture supernatant of *E. coli* containing a phage instead of the serum), while cell-based ELISA was performed according to the method described below in the section [Screening of scFv by cell-based ELISA]. Each step of this biopanning was devised so as not to select a scFv phage binding to the same portion as the C-terminal epitope of GPC3 recognized by existing antibodies, by binding in advance the existing anti-GPC3 antibodies GC33 (manufactured by Chugai Pharmaceutical Co., Ltd.) and GC199 (manufactured by Chugai Pharmaceutical Co., Ltd.) to the bait. Specifically, this competition method enables selective panning of a novel antibody recognizing a GPC3 epitope different from that for the existing anti-GPC3 antibodies. *E. coli* DH12S was transformed with the phages enriched by biopanning and inoculated to an LB agarose agar medium to separate single colonies. The *E. coli* was further cultured in a small-scale LB liquid medium, followed by the extraction and purification of plasmids. The purified plasmids were subjected to DNA sequencing to determine the nucleotide sequences of scFv H chain and L chain variable regions.

[Screening of scFv by FCM]

100 µL of the culture supernatant in which scFv phages were secreted was added to a GPC3-expressing cell line ($5\times10^3$ cells per sample) and mixed therewith, and the mixture was then incubated for 30 minutes on ice. A FACS buffer (1% BSA/PBS solution) was added thereto, and the mixture was centrifuged and washed. Then, 1 µg/mL anti-mouse antibody-Alexa 488 (manufactured by Thermo Fisher Scientific Inc.) was added thereto as a secondary antibody, and the mixture was incubated for 30 minutes on ice. Then, the fluorescent staining of the cells was measured using a flow cytometer (FACSCanto, manufactured by BD Biosciences).

[Screening of scFv by Cell-Based ELISA]

After removal of a DMEM culture solution from a 96-well microplate in which $2\times10^5$ GPC3-expressing cells were attached per well, 2% BSA-PBS solution was added for the purpose of preventing the nonspecific binding of scFv to the cells or the plate, and the plate was incubated for minutes on ice. Then, 100 μL of the culture supernatant of E. coli in which scFv phages were secreted was added to each well, and the plate was incubated for 45 minutes on ice. Then, 5 μg/mL rabbit anti-cp3 antibody (manufactured by Medical & Biological Laboratories Co., Ltd.) against cp3 fused on the C-terminal side of scFv was added at 100 μL per well, and the plate was further incubated for 45 minutes on ice. A HRP-labeled anti-rabbit IgG antibody (manufactured by Medical & Biological Laboratories Co., Ltd.) diluted 5000-fold was added at 100 μL per well as a tertiary antibody for anti-cp3 antibody detection, and the plate was incubated for 45 minutes on ice. Then, o-phenylenediamine (OPD) and hydrogen peroxide were added as substrates of HRP for color development. Quantification was performed using a numeric value obtained by subtracting absorbance at 620 nm as a background from absorbance at 492 nm. When cell-based ELISA was carried out using an antibody already converted to an IgG type antibody, not scFv, a HRP-labeled anti-mouse IgG antibody (manufactured by Medical & Biological Laboratories Co., Ltd.) diluted 2000-fold was used as a secondary antibody for the detection of the IgG type antibody instead of the anti-cp3 antibody and the HRP-labeled anti-rabbit IgG antibody among the conditions described above.

[Determination of Variable Region Gene Sequences of scFv]

The variable region gene sequences of phage scFv binding to membrane-bound GPC3 were decoded in a sequencer (CEQ2000XL, manufactured by Beckman Coulter, Inc.) using a T7 primer (primer consisting of the nucleotide sequence represented by SEQ ID NO: 176), which is a universal primer, and a cp3R primer (primer consisting of the nucleotide sequence represented by SEQ ID NO: 177) as a forward primer for H chain V region ($V_H$) decoding and a reverse primer for L chain V region ($V_L$) decoding, respectively.

[Preparation of Cell Line for Use in Antibody Epitope Mapping]

In order to identify an epitope for the cloned scFv, the mammalian display method was applied. A gene consisting of human GPC3 exons 1 to 7 and encoding a GPC3 N-terminal fragment (polypeptide consisting of the amino acid sequence represented by SEQ ID NO: 155), and a gene consisting of human GPC3 exons 8 and 9 and encoding a GPC3 C-terminal fragment (polypeptide consisting of the amino acid sequence represented by SEQ ID NO: 156) were amplified by PCR and each inserted to the multicloning site (MSC) of a pDisplay expression vector (manufactured by Thermo Fisher Scientific Inc.). The pDisplay expression vector is an expression vector capable of fusing a transmembrane domain of platelet-derived growth factor receptor (PDGFR) to the C terminus of the target protein and displaying the fusion product on the cell surface of arbitrary mammalian cells. Also, the pDisplay expression vector is constituted so as to add a HA tag to the N terminus of the target protein and to add a myc tag to the C terminus of the PDGFR. The pDisplay expression vector for expressing the GPC3 N-terminal fragment or the GPC3 C-terminal fragment was gene-transferred to a SK-Hep-1 cell line or a 293T cell line, and a cell line expressing the GPC3 N-terminal fragment or the GPC3 C-terminal fragment on the cell surface (GPC3 N-terminal fragment-expressing cell line and GPC3 C-terminal fragment-expressing cell line) was isolated and used in the epitope mapping of scFv.

[Antibody Epitope Mapping by FCM]

The GPC3 N-terminal fragment-expressing cell line, the GPC3 C-terminal fragment-expressing cell line, and the GPC3-expressing cell line ($5\times10^3$ cells each per sample) were each mixed with 100 μL of the culture supernatant in which scFv phages were secreted, and the mixture was incubated for 30 minutes on ice. A FACS buffer (1% BSA/PBS solution) was added thereto, and the mixture was centrifuged and washed. Then, 1 μg/mL anti-mouse antibody-Alexa 488 (manufactured by Thermo Fisher Scientific Inc.) was added thereto as a secondary antibody, and the mixture was incubated for 30 minutes on ice. Then, the fluorescent staining of the cells was measured using a flow cytometer (FACSCanto, manufactured by BD Biosciences).

[Construction of Recombinant IgG Expression Vector]

In order to convert scFv to IgG, an expression vector of Mammalian PowerExpress system (manufactured by Toyobo Co., Ltd.) was used. A nucleotide sequence encoding a fusion protein of the H chain variable region of scFv and a mouse IgG2a H chain-derived constant region was inserted to MSC of a pEH1.1 vector (pEH1.1-H). Also, a nucleotide sequence encoding a fusion protein of the L chain variable region of scFv and a mouse IgG2a L chain-derived constant region was inserted to MSC of a pELX2.2 vector (pEH2.2-L). Then, a polynucleotide fragment from EF1α promoter to the L chain gene was excised from pEH2.2-L with restriction enzymes (BglII and SalI) and ligated with pEH1.1-H treated with restriction enzymes (BglII and SalI) to construct a vector for coexpressing the antibody H chain and L chain.

[Expression of Recombinant IgG]

32.6 μg of the antibody H chain and L chain coexpression vector prepared by the method described above in [Construction of recombinant IgG expression vector] was diluted with 1.6 mL of opti-MEM (manufactured by Gibco/Thermo Fisher Scientific Inc.) and mixed with 65 μL of Transficient Transfection Reagent (manufactured by Medical & Biological Laboratories Co., Ltd.) diluted with 1.6 mL of opti-MEM, and the mixture was incubated at room temperature for 10 minutes. Then, the mixture was mixed with CHO-K1 cells ($1\times10^7$ cells) suspended in 10 mL of a DMEM culture solution, followed by culture. 4 hours later, a serum-free medium (Free Style expression CHO media [manufactured by Gibco/Thermo Fisher Scientific Inc.]) was added thereto, and the mixture was further cultured for 4 to 6 days to recover a culture supernatant containing a recombinant antibody.

[Affinity Purification of Antibody]

An empty column (manufactured by Bio-Rad Laboratories, Inc.) was packed with Protein G Sepharose 4 Fast Flow (manufactured by GE Healthcare Japan Corp.) or Bipo Resin Protein L (manufactured by Protein Express) at 1 mL bed volume. Then, the column resin was washed with PBS in an amount of 10 times the bed volume. The culture supernatant filtered through a 0.22 micron filter was added to the column so that the antibody was entrapped to protein G or protein L within the column. Then, the column was washed with PBS in an amount of 10 times the bed volume to wash off nonspecifically adsorbed contaminants. The antibody was eluted using a 100 mM glycine-HCl (pH 2.7) solution, and pH of the eluate was neutralized with 1 M Tris-HCl (pH 8.5). Absorbance at 280 nm was measured with an absorbance meter nanoDrop (manufactured by Thermo Fisher Scientific Inc.), and the antibody concentration was calculated. Expression vectors were also designed and prepared by the same method as above as to the GC33 antibody and the GC199 antibody used as competitive antibodies.

1-2 Results

[Antiserum Evaluation of Immunized Mouse]

Blood was collected from SKG/Jcl mice immunized four times with recombinant GPC3, and the production of an antibody against GPC3 in serum was confirmed. As a result, an antibody having binding activity against GPC3 was detected by experiments of ELIS on recombinant GPC3 and FCM on GPC3-expressing cells. Two mice having a particularly high antibody titer (individual Nos. 1413 #2 and 1413 #3) among the mice were used as sources for the preparation of an antibody library.

[Construction of Phage Library]

The number of members in a scFv library estimated by calculation from transformation efficiency was $5.8 \times 10^7$ for mouse 1413 #2 and $4.3 \times 10^8$ for mouse 1413 #3. The immunoglobulin library prepared in this Example was a library prepared from the mice found to produce antibodies in response to the target antigen by immunization with the antigen GPC3. Therefore, a feature of this library is the high possibility of containing the target antibody gene even if the library size is small. Another advantageous feature thereof is that the library contains an antibody that forms a correct conformation in vivo, as compared with a random synthetic antibody library.

[Classification of Clone by Sequence Analysis of Monoclonal scFv]

The DNA sequence analysis of picked up monoclonal scFv was conducted to perform clone classification excluding overlap. As a result, candidate clones were identified as 7 types from D series of the mouse 1413 #2 library, 5 types from E series thereof, 3 types from D series of the mouse 1413 #3 library, and 9 types from E series thereof. The nucleotide sequences of heavy chain and light chain variable regions of these candidate clones were analyzed to exclude overlapping identical clones. As a result, a total of 18 types of scFv clones, i.e., 9 types of scFv clones derived from the mouse 1413 #2 library, and 9 types of scFv clones derived from the mouse 1413 #3 library, were identified.

[Epitope Mapping Analysis of Anti-GPC3 scFv Clone]

Figure 2:
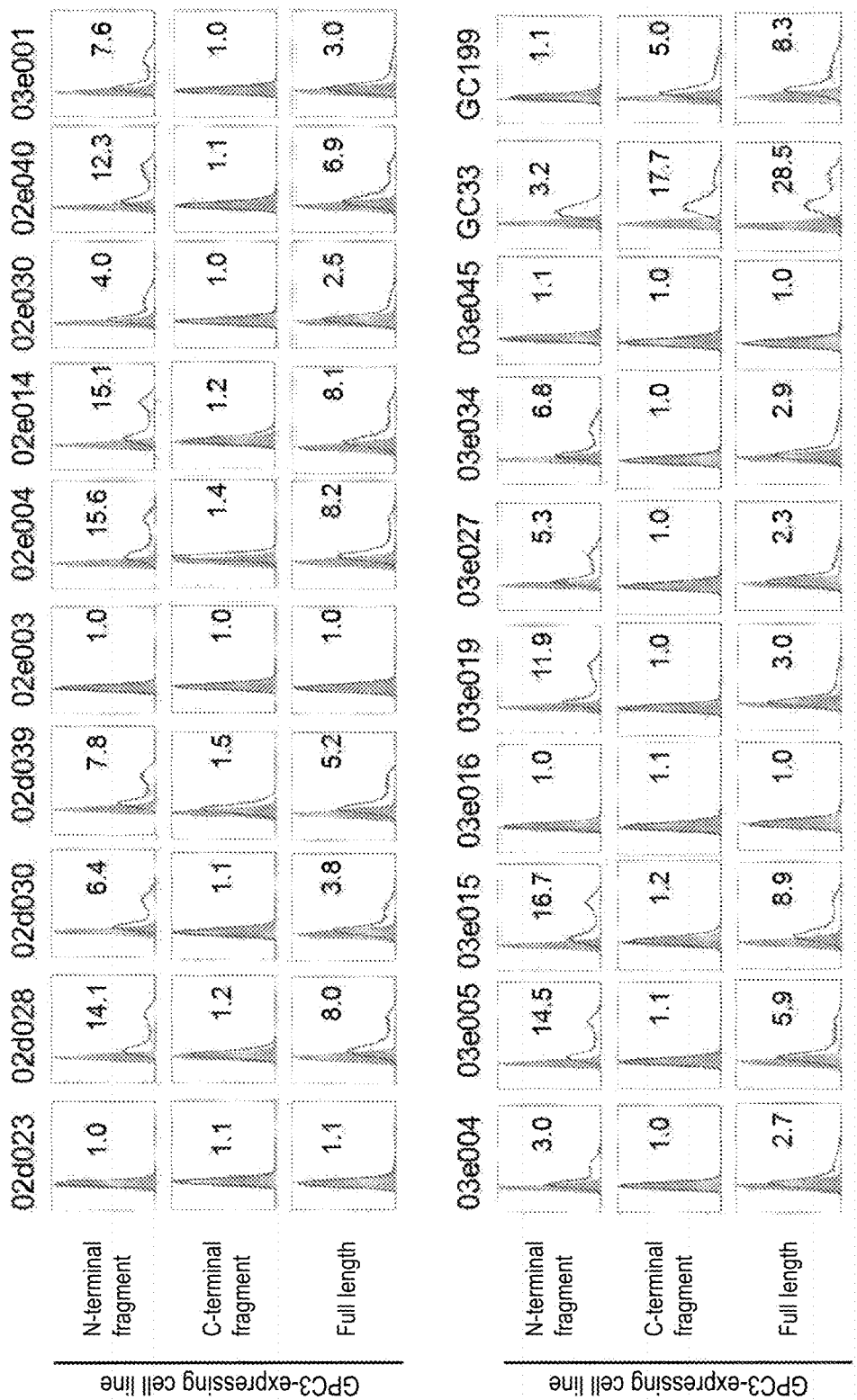
FIG. 2 is a diagram showing results of performing flow cytometry (FCM) using 18 types of anti-GPC3 scFv clones (TF1413-02d023, 02d028, 02d030, 02d039, 02e003, 02e004, 02e014, 02e030, 02e040, 03e001, 03e004, 03e005, 03e015, 03e016, 03e019, 03e027, 03e034, and 03e045) and existing anti-GPC3 antibodies (GC33 and GC199), and 3 types of cell lines (GPC3 N-terminal fragment-expressing cell line, GPC3 C-terminal fragment-expressing cell line, and GPC3 [full-length]-expressing cell line). The numeric values in the diagram are indicated by relative values when the fluorescence intensity of a cell line expressing no GPC3 (SK-Hep-1 cell line) was defined as 1 in FCM.

18 types of scFv clones identified according to the method described above in the section [Classification of clone by sequence analysis of monoclonal scFv] were used to analyze binding to each GPC3 by FCM using 3 types of cell lines (GPC3 N-terminal fragment-expressing cell line, GPC3 C-terminal fragment-expressing cell line, and GPC3-expressing cell line). As a result, among the 18 types of scFv clones, 14 types (TF1413-02d028, 02d030, 02d039, 02e004, 02e014, 02e030, 02e040, 03e001, 03e004, 03e005, 03e015, 03e019, 03e027, and 03e034) bound to full-length GPC3 and the GPC3 N-terminal fragment (polypeptide consisting of the amino acid sequence represented by SEQ ID NO: 155), but did not bind to the GPC3 C-terminal fragment (polypeptide consisting of the amino acid sequence represented by SEQ ID NO: 156) (see FIG. 2). On the other hand, the existing anti-GPC3 antibodies GC33 (manufactured by Chugai Pharmaceutical Co., Ltd.) and GC199 (manufactured by Chugai Pharmaceutical Co., Ltd.) bound to full-length GPC3 and the GPC3 C-terminal fragment, but did not bind to the GPC3 N-terminal fragment.

From these results, the 14 types of novel scFv clones described above recognizing a GPC3 N-terminal epitope different from a GPC3 C-terminal epitope for the existing anti-GPC3 antibodies (GC33 and GC199) were identified.

Among the 14 types of scFv clones thus identified, top 11 scFv clones (TF1413-02d028, 02d039, 02e004, 02e014, 02e030, 02e040, 03e001, 03e004, 03e005, 03e015, and 03e034) having particularly high binding strength were selected. Table 1 shows the correspondence of SEQ ID NOs to the H chain and L chain V regions of these 11 types of scFv clones. Table 2 shows the correspondence of SEQ ID NOs to the H chain CDR1 to CDR3 of these 11 types of scFv clones. Table 3 shows the correspondence of SEQ ID NOs to the L chain CDR1 to CDR3 of these 11 types of scFv clones.

TABLE 1

| scFv clone name and V region | | SEQ ID NO |
|---|---|---|
| TF1413-02d028 | H chain V region | 7 |
| TF1413-02d039 | H chain V region | 17 |
| TF1413-02e004 | H chain V region | 27 |
| TF1413-02e014 | H chain V region | 37 |
| TF1413-02e030 | H chain V region | 47 |
| TF1413-02e040 | H chain V region | 57 |
| TF1413-03e001 | H chain V region | 67 |
| TF1413-03e004 | H chain V region | 77 |
| TF1413-03e005 | H chain V region | 87 |
| TF1413-03e015 | H chain V region | 97 |
| TF1413-03e034 | H chain V region | 107 |
| TF1413-02d028 | L chain V region | 8 |
| TF1413-02d039 | L chain V region | 18 |
| TF1413-02e004 | L chain V region | 28 |
| TF1413-02e014 | L chain V region | 38 |
| TF1413-02e030 | L chain V region | 48 |
| TF1413-02e040 | L chain V region | 58 |
| TF1413-03e001 | L chain V region | 68 |
| TF1413-03e004 | L chain V region | 78 |
| TF1413-03e005 | L chain V region | 88 |
| TF1413-03e015 | L chain V region | 98 |
| TF1413-03e034 | L chain V region | 108 |

TABLE 2

| Clone name and CDR | | SEQ ID NO |
|---|---|---|
| TF1413-02d028 | H chain CDR1 | 1 |
| | H chain CDR2 | 2 |
| | H chain CDR3 | 3 |
| TF1413-02d039 | H chain CDR1 | 11 |
| | H chain CDR2 | 12 |
| | H chain CDR3 | 13 |
| TF1413-02e004 | H chain CDR1 | 21 |
| | H chain CDR2 | 22 |
| | H chain CDR3 | 23 |
| TF1413-02e014 | H chain CDR1 | 31 |
| | H chain CDR2 | 32 |
| | H chain CDR3 | 33 |
| TF1413-02e030 | H chain CDR1 | 41 |
| | H chain CDR2 | 42 |
| | H chain CDR3 | 43 |
| TF1413-02e040 | H chain CDR1 | 51 |
| | H chain CDR2 | 52 |
| | H chain CDR3 | 53 |
| TF1413-03e001 | H chain CDR1 | 61 |
| | H chain CDR2 | 62 |
| | H chain CDR3 | 63 |
| TF1413-03e004 | H chain CDR1 | 71 |
| | H chain CDR2 | 72 |
| | H chain CDR3 | 73 |
| TF1413-03e005 | H chain CDR1 | 81 |
| | H chain CDR2 | 82 |
| | H chain CDR3 | 83 |
| TF1413-03e015 | H chain CDR1 | 91 |
| | H chain CDR2 | 92 |
| | H chain CDR3 | 93 |

TABLE 2-continued

| Clone name and CDR | | SEQ ID NO |
|---|---|---|
| TF1413-03e034 | H chain CDR1 | 101 |
| | H chain CDR2 | 102 |
| | H chain CDR3 | 103 |

TABLE 3

| Clone name and CDR | | SEQ ID NO |
|---|---|---|
| TF1413-02d028 | L chain CDR1 | 4 |
| | L chain CDR2 | 5 |
| | L chain CDR3 | 6 |
| TF1413-02d039 | L chain CDR1 | 14 |
| | L chain CDR2 | 15 |
| | L chain CDR3 | 16 |
| TF1413-02e004 | L chain CDR1 | 24 |
| | L chain CDR2 | 25 |
| | L chain CDR3 | 26 |
| TF1413-02e014 | L chain CDR1 | 34 |
| | L chain CDR2 | 35 |
| | L chain CDR3 | 36 |
| TF1413-02e030 | L chain CDR1 | 44 |
| | L chain CDR2 | 45 |
| | L chain CDR3 | 46 |
| TF1413-02e040 | L chain CDR1 | 54 |
| | L chain CDR2 | 55 |
| | L chain CDR3 | 56 |
| TF1413-03e001 | L chain CDR1 | 64 |
| | L chain CDR2 | 65 |
| | L chain CDR3 | 66 |
| TF1413-03e004 | L chain CDR1 | 74 |
| | L chain CDR2 | 75 |
| | L chain CDR3 | 76 |
| TF1413-03e005 | L chain CDR1 | 84 |
| | L chain CDR2 | 85 |
| | L chain CDR3 | 86 |
| TF1413-03e015 | L chain CDR1 | 94 |
| | L chain CDR2 | 95 |
| | L chain CDR3 | 96 |
| TF1413-03e034 | L chain CDR1 | 104 |
| | L chain CDR2 | 105 |
| | L chain CDR3 | 106 |

[Conversion of Anti-GPC3 scFv Antibody to IgG and its ability to bind]

Figure 3:
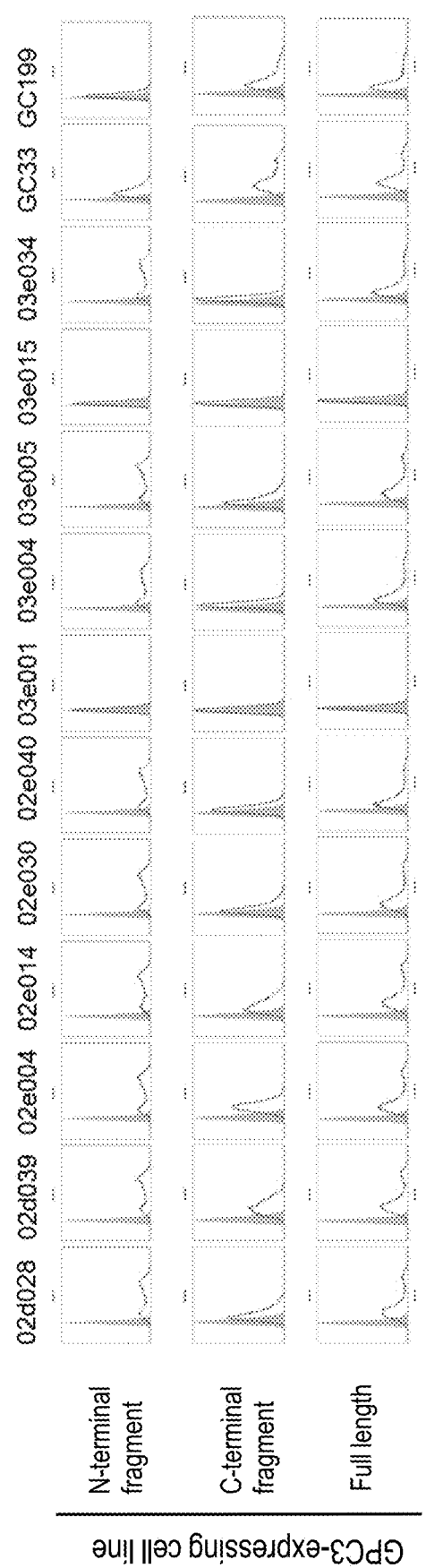
FIG. 3 is a diagram showing results of performing FCM using IgG antibodies prepared from 11 types of scFv clones (TF1413-02d028, 02d039, 02e004, 02e014, 02e030, 02e040, 03e001, 03e004, 03e005, 03e015, and 03e034) and existing anti-GPC3 antibodies (GC33 and GC199), and 3 types of cell lines (GPC3 N-terminal fragment-expressing cell line, GPC3 C-terminal fragment-expressing cell line, and GPC3 [full-length]-expressing cell line).

The H chain and L chain variable regions of the 11 types of scFv clones selected as described above were bound to mouse IgG constant regions, and full-length recombinant antibodies were expressed using a vector for recombinant IgG expression and affinity-purified. The ability of these IgG antibodies to bind to the GPC3 N-terminal fragment was analyzed using the GPC3 N-terminal fragment-expressing cell line. As a result, 9 types of IgG clones (TF1413-02d028, 02d039, 02e004, 02e014, 02e030, 02e040, 03e004, 03e005, and 03e034) maintained binding activity against the GPC3 N-terminal fragment, whereas the remaining two types of IgG clones (TF1413-03e001 and 03e015) lacked binding activity against the GPC3 N-terminal fragment (see FIG. 3). The 9 types of IgG clones described above did not bind to the GPC3 C-terminal fragment (see FIG. 3).

These results indicate that among the 11 types of scFv clones, 9 types (TF1413-02d028, 02d039, 02e004, 02e014, 02e030, 02e040, 03e004, 03e005, and 03e034) are convertible to IgG type. Table 4 shows the correspondence of SEQ ID NOs to the H chains and the L chains of the 11 types of IgG clones.

TABLE 4

| IgG clone name and region | | SEQ ID NO |
|---|---|---|
| TF1413-02d028 | H chain | 9 |
| TF1413-02d039 | H chain | 19 |
| TF1413-02e004 | H chain | 29 |
| TF1413-02e014 | H chain | 39 |
| TF1413-02e030 | H chain | 49 |
| TF1413-02e040 | H chain | 59 |
| TF1413-03e001 | H chain | 69 |
| TF1413-03e004 | H chain | 79 |
| TF1413-03e005 | H chain | 89 |
| TF1413-03e015 | H chain | 99 |
| TF1413-03e034 | H chain | 109 |
| TF1413-02d028 | L chain | 10 |
| TF1413-02d039 | L chain | 20 |
| TF1413-02e004 | L chain | 30 |
| TF1413-02e014 | L chain | 40 |
| TF1413-02e030 | L chain | 50 |
| TF1413-02e040 | L chain | 60 |
| TF1413-03e001 | L chain | 70 |
| TF1413-03e004 | L chain | 80 |
| TF1413-03e005 | L chain | 90 |
| TF1413-03e015 | L chain | 100 |
| TF1413-03e034 | L chain | 110 |

Example 2

2. Binding Activity of Novel Anti-GPC3 Antibody Against GPC3 Treated with EDTA (Ethylenediaminetetraacetic Acid), Trypsin or Collagenase

[Preparation of Cell Treated with EDTA or Trypsin]

A SK-Hep-1 cell line forced to express GPC3 was cultured in two T-75 flasks. The culture supernatant of each flask was aspirated, and the flask was washed with 3 mL of PBS. Then, 3 mL of 0.02% EDTA/PBS solution (hereinafter, simply referred to as "EDTA") or 0.05% trypsin solution (hereinafter, simply referred to as "trypsin") was added to each flask. Each flask was incubated at 37° C. for 5 minutes (EDTA) or 2 minutes and 30 seconds (trypsin) to dissociate the cells from the flask. Then, 7 mL of a DMEM culture solution was added to each flask. After pipetting, the cell suspension was recovered into each 50 mL conical tube. Each flask was further washed with 10 mL of a DMEM culture solution. Then, the recovered washes were also recovered into the 50 mL conical tube containing each cell suspension, followed by centrifugation (1,500 rpm, 4° C., 4 min). After aspiration of the supernatant from each conical tube, 10 mL of a DMEM culture solution was added to the pellet, and the number of cells dissociated with EDTA or trypsin was counted.

The cells treated with EDTA or trypsin were adjusted to $2 \times 10^3$ cells/tube and subjected to FACS (EC800) analysis. The FACS analysis employed 3 types of antibodies (fluorescently APC-labeled anti-mouse IgG antibody [5 μg/tube; manufactured by BioLegend, Inc.], GC33 antibody [1.0 μg/tube; manufactured by Medical & Biological Laboratories Co., Ltd. Life Science], and scFv clone [TF1413-02d028] antibody described above [1.0 μg/tube]).

[Preparation of cell treated with collagenase]

Figure 4:
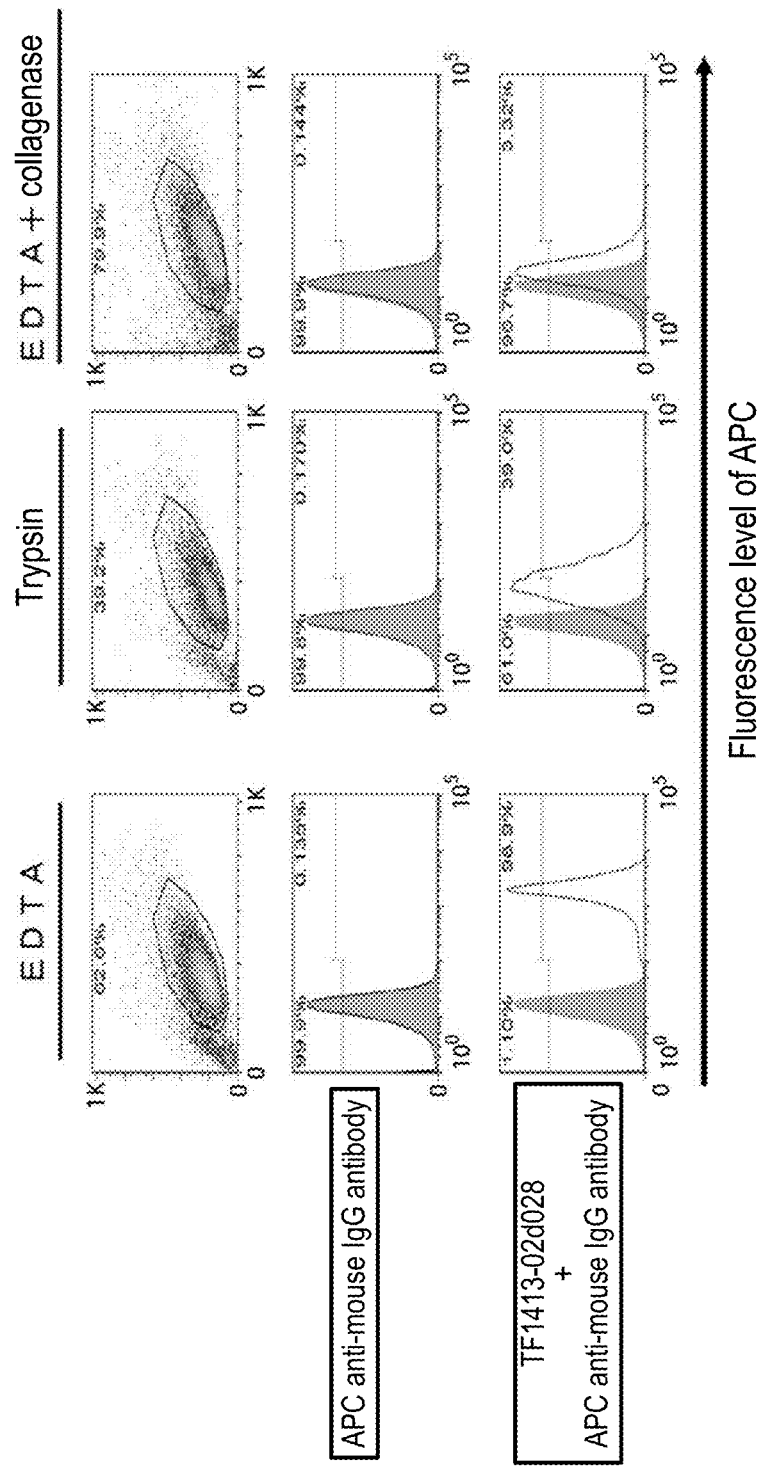
FIG. 4 is a diagram showing results of performing FACS (fluorescence activated cell sorting) using a GPC3-expressing cell line treated with 3 types of methods (EDTA, trypsin, and "EDTA+collagenase"), 3 types of antibody combinations (anti-mouse IgG antibody labeled with APC [hereinafter, also referred to as "APC ant-mouse IgG antibody"], and a combination of the APC anti-mouse IgG antibody and a scFv clone [TF1413-02d028] antibody).

$1 \times 10^6$ cells dissociated with EDTA as described above were placed in a 50 mL conical tube and centrifuged (1,500 rpm, 4° C., 4 min), and the supernatant was aspirated to prepare a cell mass (pellet). 5 mL of a collagenase P solution was added to the pellet, and the mixture was incubated at 37° C. for 30 minutes to prepare a cell suspension. Then, the cell suspension was passed through a 100 μm cell strainer while washed with 30 mL of a DMEM culture solution. The cell suspension was passed again through a 100 μm cell strainer and centrifuged (300 g, 4° C., 10 min), and the supernatant was aspirated. The pellet was washed by the addition of 20 mL of PBS and then centrifuged (300 g, 4° C., 5 min), and the supernatant was aspirated. The cells were suspended by the addition of 5 mL of a DMEM culture solution. Then, the number of cells was counted, and $2 \times 10^3$ cells/tube were analyzed by FACS (EC800). The FACS analysis employed 3 types of antibodies (fluorescently APC-labeled anti-mouse IgG antibody [5 µg/tube; manufactured by BioLegend, Inc.], GC33 antibody [1.0 µg/tube; manufactured by Medical & Biological Laboratories Co., Ltd. Life Science], and scFv clone [TF1413-02d028] antibody described above [1.0 µg/tube]), as in the cells treated with EDTA or trypsin. The results are shown in FIG. 4. In FIG. 4, the right peak on the abscissa represents that the GC33 antibody or the scFv clone [TF1413-02d028] antibody bound to the GPC3 protein.

[Results]

As shown in FIG. 4, the binding activity of the antibody of the present invention (TF1413-02d028) against the GPC3 protein treated with trypsin or collagenase was markedly decreased. These results indicate that the antibody of the present invention specifically recognizes the conformation of the GPC3 protein, suggesting that the antibody of the present invention has high specificity in vivo.

Example 3

3. Development of GPC3 CAR-T Cell Using Novel Anti-GPC3 Antibody

SUMMARY

GPC3 is a cell surface molecule, the expression of which is not observed in human adult tissues except for placenta, but is observed in tissues of various cancers such as hepatocellular carcinoma, melanoma, ovarian clear cell adenocarcinoma, and lung squamous cell carcinoma. Thus, GPC3 is capable of serving as a target molecule in CAR-T cell therapy exploiting a chimeric antigen receptor (CAR). Accordingly, GPC3 CAR-T cells were prepared using 11 types of scFv clones prepared in Example 1 and analyzed for cancer cytotoxic activity and the ability to produce interferon γ (IFN-γ).

[Preparation of GPC3 CAR Vector]

scFv having a $V_H$-linker-$V_L$ sequence was designed as to 11 types of scFv clones (TF1413-02d028, 02d039, 02e004, 02e014, 02e030, 02e040, 03e001, 03e004, 03e005, 03e015, and 03e034) prepared in Example 1, on the basis of their respective amino acid sequences of $V_H$ and $V_L$ (see Table 5). The linker used consisted of 15 amino acid residues with 3 repeats of a polypeptide "GGGGS" (SEQ ID NO: 191). A human immunoglobulin H chain-derived signal sequence consisting of the amino acid sequence represented by SEQ ID NO: 188 was added to the N terminus of $V_H$.

TABLE 5

SEQ ID NO: 165: TF1413-02d028-derived scFv
QVQLKESGPELEKPGASVKISCKASGYSFTGYNMNWVKQSNGKSLEWIGNIDPYYGGTSYNQKF
KGKATLTVDKSSSTAYMQLKSLTSEDSAVYYCARGDYRAYYFDYWGQGTTLTVSGGGGSGGGGS
GGGGSDIQMTQSPKFMSTSVGDRVSITCKASQNVRTAVAWYQQKPGQSPKALIYLASNRHTGVP
DRFTGSGSGTDFTLTISNVQSEDLADYFCLQHWNYPLTFGAGTKLELKR SEQ ID NO: 166: TF1413-02d039-derived scFv
EVKLVESGGGLVKPGGSLKLSCAASGFAFSSYDMSWVRQTPEKRLEWVAYISSGGGSTYYPDTV
KGRFTISRDNAKNTLYLQMSSLKSEDTAMYYCARRGLRRAMDYWGQGTSVTVSGGGGSGGGGSG
GGGSDVVMTQTPLSLPVSLGDQASISCRSSQSLVHSNGNTYLHWYLQKPGQSPKLLIYKVSNRF
SGVPDRFSGSGSGTDFTLKISRVEAEDLGVYFCSQSTHVPLTFGAGTKLELKR SEQ ID NO: 167: TF1413-02e004-derived scFv
QVQLQQSGAELVKPGAPVKLSCKASGYTFTSYWMNWVKQRPGRGRGLEWIGRIDPSDSETHYNQ
KFKDEATLTVDKSSSTAYIQLSSLTSEDSAVYYCARGYYAMDYWGQGTSVTVSGGGGSGGGGSG
GGGSDIVLTQSPKFMSTSVGDRVSITCKASQDVSTAVAWYQQKPGQSPKLLIYSASYRYTGVPD
RFTGSGSGTDFTFTISSVQAEDLAVYYCQQHYSTPTFGGGTKLEIKR SEQ ID NO: 168: TF1413-02e014-derived scFv
QVQLKQSGAELVRSGASVKLSCTASGFNIKDYYMHWVKQRPEQGLEWIGWIDPENGDTEYAPKF
QGKATMTADTSSNTAYLQLSSLTSEDTAVYYCNAGYYDYDGYAMDYWGQGTSVTVSGGGGSGGG
GSGGGGSDIVLTQSPKFMSTSVGDRVSITCKASQDVGTAVAWYQQKPGQSPKLLIYWASTRHTG
VPDRFTGSGSGTDFTLTISNVQSEDLADYFCQQYSSYPLTFGGGTKLEIKR SEQ ID NO: 169: TF1413-02e030-derived scFv
EVQLQQSGAELVRPGALVKLSCKASGFNIKDYYMHWVKQRPEQGLEWIGWIDPENGNTIYDPKF
QGKASITADTSSNTAYLQLSSLTSEDTAVYYCAISTMITTLDYWGQGTTLTVSGGGGSGGGGSG
GGGSDIQMTQSPSSLAMSVGQKVTMSCKSSQSLLNSSNQKNYLAWYQQKPGQSPKLLVYFASTR
ESGVPDRFIGSGSGTDFTLTISSVQAEDLADYFCQQHYSTPLTFGAGTKLELKR SEQ ID NO: 170: TF1413-02e040-derived scFv
EVMLVESGPELVKPGASMKISCKASGYSFTGYTMNWVKQSHGKNLEWIGLINPYNGGTSYNQNF
KGKATLTVDKSSSTAYMELLSLTSEDSAVYYCARGYYGRFDYWGQGTTLTVSGGGGSGGGGSGG
GGSDILLTQSPKFMSTSVGDRVSITCKASQNVRTAVAWYQQKPGQSPKALIYLASNRHTGVPDR
FTGSGSGTDFTLTISNVQSEDLADYFCLQHWNYPLTFGAGTKLELKR TABLE 5-continued SEQ ID NO: 171: TF1413-03e001-derived scFv
QVQLKQSGPELVKPGASVKISCKASGYSFTGYYMHWVKQSHVKSLEWIGRINPYNGATSYNQNF
KDKASLTVDKSSSTAYMELHSLTSEDSAVYYCARNYGYFDYWGQGTTLTVSGGGGSGGGGSGGG GSDIKMTQSPKFMSTSVGDRVSVTCEASQNVDNNVVWYQQKPGQSPKALIYSASYRYSGVPDRF
TGSGSGTDFTLTISNVQSEDLAEYFCQQYNSYPLTFGAGTKLEIKR SEQ ID NO: 172: TF1413-03e004-derived scFv
QVQLKQSGAELVKPGAPVKLSCKASGYTFTSYWMNWVKQRPGRGLEWIGRIDPSDSETHYNQKF
KDKATLTVDKSSSTAYIQLSSLTSEDSAVYYCARGYYGSNYWGQGTTLTVSGGGGSGGGGSGGG GSDIKMTQSPKFMSTSVGDRVSVTCKASQNVGTNVAWYQQKPGQSPKALIYSASYRYSGVPDRF
TGSGSGTDFTLTISNVQSEDLAEYFCQQYNSYPLTFGAGTKLELKR SEQ ID NO: 173: TF1413-03e005-derived scFv
QVQLKESGAELVRSGASVKLSCTASGFNIKDYYMHWVKQRPEQGLEWIGWIDPENGDTEYAPKF
QGKATMTADTSSNTAYLQLSSLTSEDTAVYYCNAFYYDYDGYAMDYWGQGTSVTVSGGGGSGGG GSGGGGSDVVMTQTPSSLSASLGERVSLTCRASQEISGYLSWLQQKPDGTIKRLIYAASTLDSG
VPKRFSGSRSGSDYSLTISSLESEDFADYYCLQYASYPLTFGAGTKLELKR SEQ ID NO: 174: TF1413-03e015-derived scFv
EVQLQQSGPELVKPGASMKISCKASGYSFTGYTMNWVKQSHGKNLEWIGLINPYNGGTSYNQKF
KGKATLTVDKSSSTAYMELLSLTSEDSAVYYCARGDYYPPYAMDYWGQGTSVTVSGGGGSGGGG SGGGGSDIVMSQSPKFMSTSVGDRVSVTCKASQNVGTNVAWYQQKPGQSPKPLIYSASYRYSGV
PDRFTGSGSGTDFTLTISNVQSEDLAEYFCQQYNRYPLTFGVGTKLEIKR SEQ ID NO: 175: TF1413-03e034-derived scFv
EVQLQQSGPELEKPGASVKISCKASGYSFTGYNMNWVKQSNGKSLEWIGNIDPYYGGTSYNQKF
KGKATLTVDKSSSTAYMQLKSLTSEDSAVYYCARGNYGYYAMDYWGQGTSVTVSGGGGSGGGGS GGGGSDIVMSQSPKFMSTSVGDRVSITCKASQNVRTAVAWYQQKPGQSPKALIYLASNRHTGVP
DRFTGSGSGTDFTLTISNVQSEDLADYFCLQHWNYPLTFGAGTKLELKR In the tables, the linker is boxed in a double line, $V_H$ is underlined with a single line, and $V_L$ is underlined with a double line.

A nucleotide sequence encoding each anti-GPC3 scFv of Table 5 was synthesized by optimization for human codons and inserted to a CAR expression vector. The CAR gene used had a gene encoding a fusion peptide (peptide consisting of the amino acid sequence represented by SEQ ID NO: 185) consisting of a human CD8-derived transmembrane region and a human CD28/4-1BB/CD3 zeta-derived immunocompetent cell activation signal transduction region, a 2A self-cleaving sequence, human IL-7 gene, a 2A self-cleaving sequence, human CCL19 gene, a 2A self-cleaving sequence, and HSV-TK gene, downstream of the scFv gene, and the whole was incorporated into a MSGV1 retrovirus vector (see International Publication No. WO 2016/056228).

[Preparation of GPC3 CAR-T Cell]

The GPC3 CAR vectors derived from the 11 types of scFv clones described above were each transiently introduced to GP2 packaging cells to prepare retrovirus vectors. T cells were infected with these vectors for gene transfer to induce GPC3 CAR-T cells. The ratio of GPC3 CAR-expressing cells to the gene-transferred T cells varied from 5.3 to 39.2%. Accordingly, the following function assay was carried out using GPC3 CAR-T cells derived from 5 types of scFv clones (TF1413-02d028, TF1413-02d039, TF1413-02e014, TF1413-02e030, and TF1413-03e005) that exhibited 25% or more of the ratio.

[Damaging Activity of GPC3 CAR-T Cell Against GPC3-Expressing Cell Line]

Figure 5:
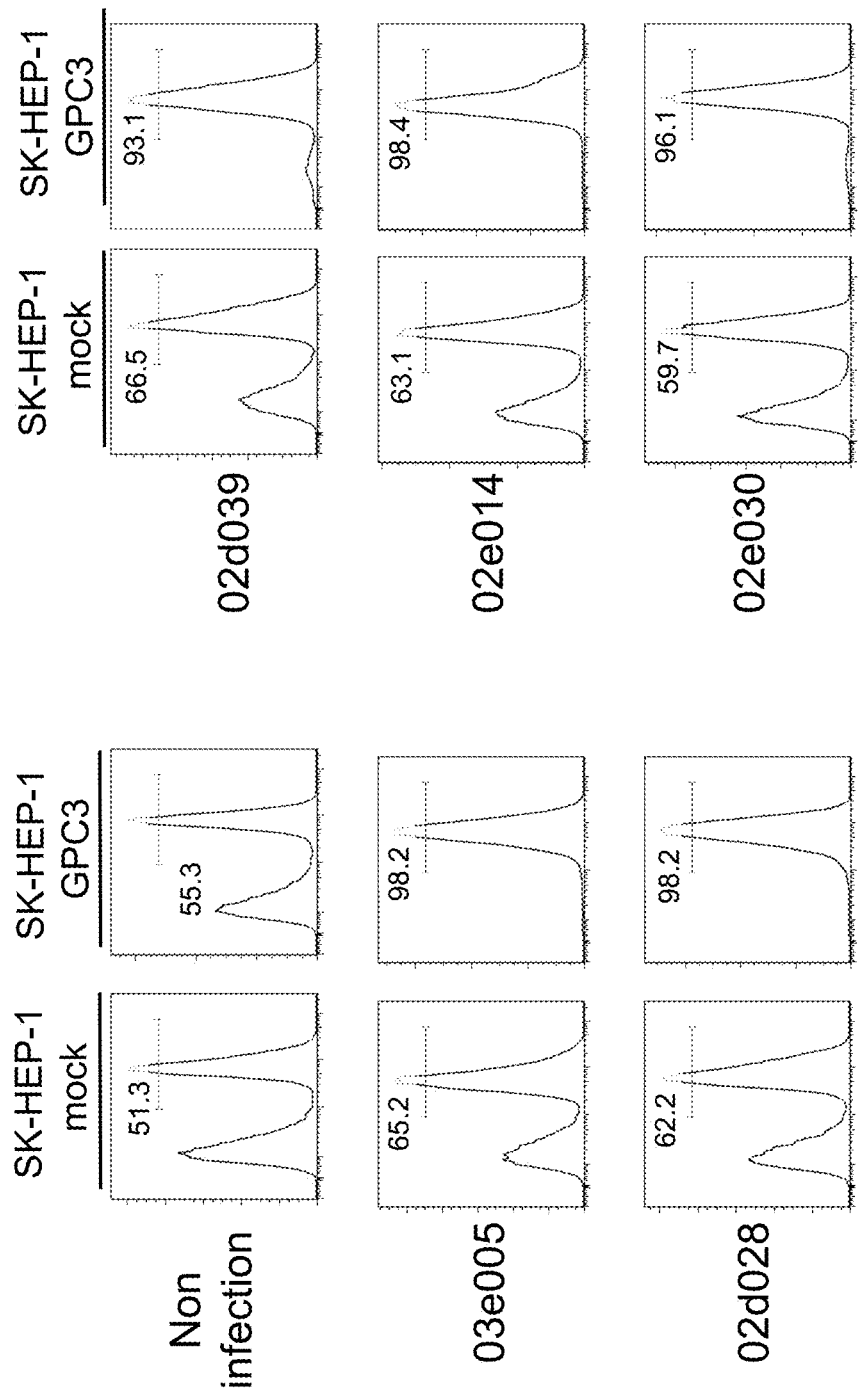
FIG. 5 is a diagram showing results of analyzing GPC3 CAR-T cells (T cells expressing CAR of scFv recognizing GPC3) derived from 5 types of scFv clones (TF1413-02d028, TF1413-02d039, TF1413-02e014, TF1413-02e030, and TF1413-03e005) for cytotoxic activity against a Sk-HEP-1 GPC3 cell line. In each graph, the right peak depicts CD45-positive cells (GPC3 CAR-T cells), and the left peak depicts CD45-negative cells (residual cancer cells [Sk-HEP-1 GPC3 cells]). The ordinate of each graph depicts the number of cells. The numeric value in each graph depicts the ratio (%) of the number of CD45-positive cells to the total number of cells (CD45-positive cells and CD45-negative cells). T cells expressing no GPC3 CAR ("Non infection" in the diagram) were used as a control.
Figure 6:
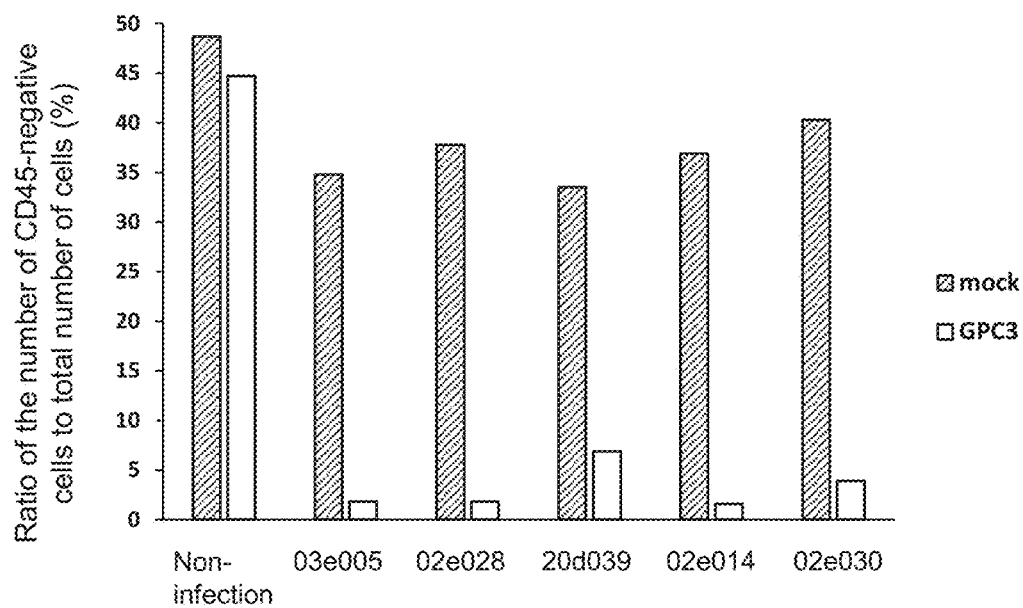
FIG. 6 is a graph showing the ratio of CD45-negative cells in FIG. 5 (FIG. 6A) and the number of CD45-negative cells (FIG. 6B). In a pair of bar graphs, the left bar graph depicts "mock" (Sk-HEP-1 mock cell line), and the right bar graph depicts "GPC3" (Sk-HEP-1 GPC3 cell line).
Figure 6:
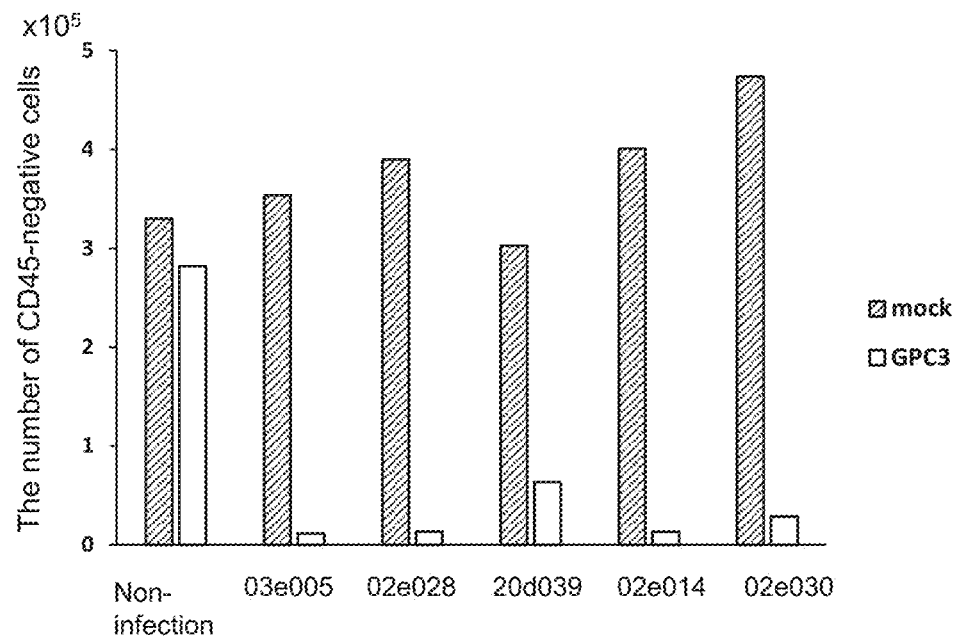

In order to study the damaging activity of the GPC3 CAR-T cells against cancer cells, coculture assay was carried out using the GPC3 CAR-T cells and a GPC3-expressing cell line, i.e., a hepatocellular carcinoma-derived cell line Sk-HEP-1 caused to express GPC3 (Sk-HEP-1 GPC3 cell line), or a cell line expressing no GPC3 (Sk-HEP-1 mock cell line). The GPC3 CAR-T cells were mixed with the target cancer cells (Sk-HEP-1 GPC3 cell line or Sk-HEP-1 mock cell line) at a ratio of 1:1 ($1\times10^3$ cells/well) and cultured in a 24-well plate. 48 hours later, the cells were recovered, stained with an anti-CD45 antibody, and analyzed by FCM with CD45-positive cells as GPC3 CAR-T cells and CD45-negative cells as residual cancer cells [Sk-HEP-1 GPC3 cells]. As a result, all the GPC3 CAR-T cells derived from the 5 types of scFv clones described above almost completely damaged the Sk-HEP-1 GPC3 cells, but did not exhibit damaging activity against the Sk-HEP-1 mock cells (see FIGS. 5 and 6). In the case of using cells uninfected with the virus vector (non-gene-transferred cells ["Non infection" in FIGS. 5 and 6]) as a negative control for the GPC3 CAR-T cells, these cells exhibited damaging activity neither against the Sk-HEP-1 GPC3 cells nor against the Sk-HEP-1 mock cells.

From these results, the GPC3CAR-T cells derived from the selected 5 types of anti-GPC3 scFv clones (TF1413-02d028, TF1413-02d039, TF1413-02e014, TF1413-02e030, and TF1413-03e005) were shown to specifically exert cytotoxic activity against cancer cells expressing GPC3.

[Ability of GPC3 CAR-T Cell to Produce IFN-γ by Recognizing GPC3-Expressing Cell]

Figure 7:
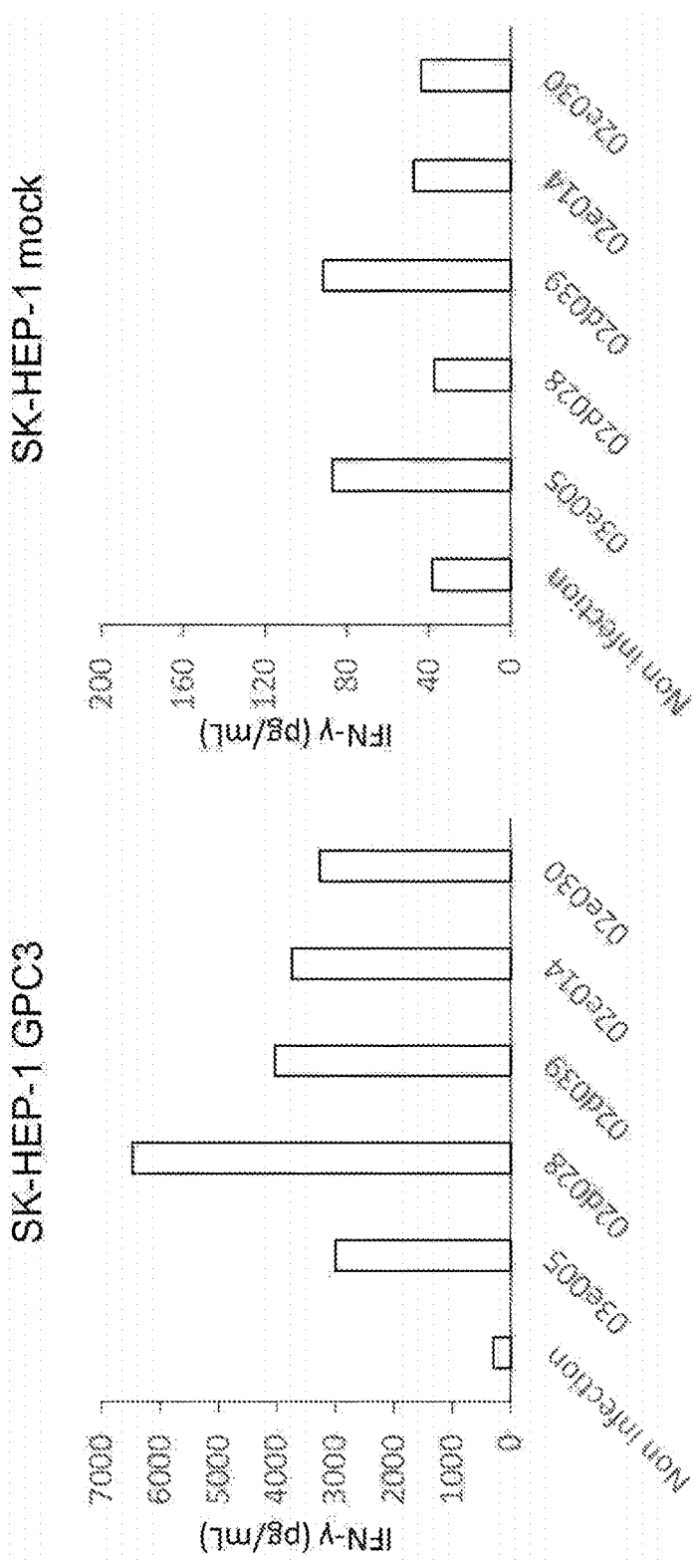
FIG. 7 is a diagram showing results of analyzing GPC3 CAR-T cells derived from 5 types of scFv clones (TF1413-02d028, TF1413-02d039, TF1413-02e014, TF1413-02e030, and TF1413-03e005) for the ability to produce IFN-γ against a Sk-HEP-1 GPC3 cell line. T cells expressing no GPC3 CAR ("Non infection" in the diagram) were used as a control.

In addition to the damaging activity against GPC3-expressing (positive) cancer cells, the ability of the GPC3 CAR-T cells to produce IFN-γ was analyzed. The GPC3 CAR-T cells were mixed with the target cancer cells (Sk- HEP-1 GPC3 cell line or Sk-HEP-1 mock cell line) at a ratio of 1:1 (1×10³ cells/well) and cultured for 48 hours in a 24-well plate, and the concentration of IFN-γ produced into the culture supernatant was measured by ELISA. As a result, all the GPC3 CAR-T cells derived from the 5 types of scFv clones described above exhibited the ability to produce IFN-γ in a manner dependent on the expression of GPC3. Particularly, the GPC3 CAR-T cells derived from clone TF1413-02d028 exhibited the highest ability to produce IFN-γ (see FIG. 7).

Example 4

4. Preparation of Humanized Antibody scFv humanized antibodies were designed on the basis of two types of scFv clones (TF1413-02d028 and 02d039) prepared in Example 1 (see Table 6). The linker used consisted of 15 amino acid residues with 3 repeats of a polypeptide "GGGGS" (SEQ ID NO: 191). A human immunoglobulin H chain-derived signal sequence consisting of the amino acid sequence represented by SEQ ID NO: 188 was added to the N terminus of V$_H$.

TABLE 6

```
SEQ ID NO: 178: #5 VH1-15-VL1 (TF1413-02d028-derived scFv humanized antibody 1)
QVQLVQSGAEVKKPGASVKVSCKASGYSFTGYNMNWVRQAPGQGLEWIGNIDPYYGGTSYNQKFKGRATLTVDT
STSTAYMELRSLRSDDTAVYYCARGDYRAYYFDYWGQGTTVTVSSGGGGSGGGGSGGGGSDIQMTQSPSSLSAS
VGDRVTITCKASQNVRTAVAWYQQKPGKAPKALIYLASNRHTGVPSRFSGSGSGTDFTKTISSPSRFSGSGSGT
DFTKTISSLQPEDFATYYCLQHWNYPLTFGGGTKVEIK SEQ ID NO: 179: #5 VH2-15-VL1 (TF1413-02d028-derived scFv humanized antibody 2)
QVQLVQSGAEVKKPGASVKVSCKASGYSFTGYNMNWVRQAPGQGLEWIGNIDPYYGGTSYNQKFKGRVTLTVDT
STSTAYMELRSLRSDDTAVYYCARGDYRAYYDFYWGQGTTVTVSSGGGGSGGGGSGGGGSDIQMTQSPSSLSAS
VGDRVTITCKASQNVRTAVAWYQQKPGKAPKALIYLASNRHTGVPSRFSGSGSGTDFTLTISSLQPEDFATYYC
LQHWNYPLTFGGGTKVEIK SEQ ID NO: 180: #5 VH3-15-VL1 (TF1413-02d028-derived scFv humanized antibody 3)
QVQLVQSGAEVKKPGASVKVSCKASGYTFTGYNMNWVRQAPGQGLEWIGNIDPYYGGTSYNQKFKGRVTLTVDT
STSTAYMELRSLRSDDTAVYYCARGDYRAYYFDYWGQGTTVTVSSGGGGSGGGGSGGGGSDIQMTQSPSSLSAS
VGDRVTITCKASQNVRTAVAWYQQKPGKAPKALIYLASNRHTGVPSRFSGSGSGTDFTLTISSLQPDFATYYCL
QHWNYPLTFGGGTKVEIK SEQ ID NO: 181: #6 VH1-15-VL1 (TF1413-02d039-derived scFv humanized antibody 1)
EVQLVESGGGLVQPGGSLRLSCAASGFAFSSYDMSWVQAPGKGLEWVAYISSGGGSTYYPDTVKGRFTISRDNA
KNSLYLQMNSLRAEDTAVYYCARRGLRRAMDYWGQGTMVTVSSGGGGSGGGGSGGGGSDIVMTQSPLSLPVTPG
EPASISCRSSQSLVHSNTYLHWYLQKPGQSPQLLIYKVSNRFSGVPDRFSGSGSGTDFTLKISRVEAEDVGVYY
CSQSTHVPLTFGGGTKVEIK SEQ ID NO: 182: #6 VH1-15-VL2 (TF1413-02d039-derived scFv humanized antibody 2)
EVQLVESGGGLVQPGGSLRLSCAASGFAFSSYDMSWVRQAPGKGLEWVAYISSGGGSTYYPDTVKGRFTISRDN
AKNSLYLQMNSLRAEDTAVYYCARRGLRRAMDYWGQGTMVTVSSGGGGSGGGGSGGGGSDIVMTQSPLSLPVTP
GEPASISCRSSQSLVHSSGNTYLHWYLQKPGQSPQLLIYKVSNRFSGVPDRFSGSGSGTDFTLKISRVE AEDV
GVYYCSQSTHVPLTFGGGTKVEIK SEQ ID NO: 183: #6 VH2-15-VL1 (TF1413-02d039-derived scFv humanized antibody 3)
EVQLVESGGGLVQPGGSLRLSCAASGFAFSSYDMSWVRQAPGKRLEWVAYISSGGGSTYYPDTVKGRFTISRDN
AKNSLYLQMNSLRAEDTAVYYCARRGLRRAMDYWGQGTMVTVSSGGGGSGGGGSGGGGSDIVMTQSPLSLPVTP
GEPASISCRSSQSLVHSNGNTYLHWYLQKPGQSPQLLIYKVSNRFSGVPDRFSGSGSGTDFTLKISRVE AEDV
GVYYCSQSTHVPLTFGGGTKVEIK SEQ ID NO: 184: #6 VH2-15-VL2 (TF1413-02d039-derived scFv humanized antibody 4)
EVQLVESGGGLVQPGGSLRLSCAASGFAFSSYDMSWVRQAPGKRLEWVAYISSGGGSTYYPDTVKGRFTISRDN
AKNSLYLQMNSLRAEDTAVYYCARRGLRRAMDYWGQGTMVTVSSGGGGSGGGGSGGGGSDIVMTQSPLSLPVTP
GEPASISCRSSQSLVHSSGNTYLHWYLQKPGQSPQLLIYKVSNRFSGVPDRFSGSGSGTDFTLKISRVE AEDV
GVYYCSQSTHVPLTFGGGTKVEIK
```

In the tables, the linker is boxed in a double line, $V_H$ is underlined with a single line, and $V_L$ is underlined with a double line.

INDUSTRIAL APPLICABILITY

The present invention contributes to the field of cancer immunotherapy.

The invention claimed is:

1. An antibody specifically binding to a human GPC3 (glypican-3)-derived polypeptide consisting of the amino acid sequence represented by SEQ ID NO: 155, wherein the antibody
   (1-1) comprises a heavy chain complementarity determining region (CDR) 1 consisting of the amino acid sequence represented by SEQ ID NO: 1, a heavy chain CDR2 consisting of the amino acid sequence represented by SEQ ID NO: 2, and a heavy chain CDR3 consisting of the amino acid sequence represented by SEQ ID NO: 3, and
   a light chain CDR1 consisting of the amino acid sequence represented by SEQ ID NO: 4, a light chain CDR2 consisting of the amino acid sequence represented by SEQ ID NO: 5, and a light chain CDR3 consisting of the amino acid sequence represented by SEQ ID NO: 6.

2. The antibody according to claim 1, wherein the antibody
   (1-2) comprises a heavy chain variable region consisting of an amino acid sequence having at least 80% or higher sequence identity to the amino acid sequence represented by SEQ ID NO: 7, and a light chain variable region consisting of an amino acid sequence having at least 80% or higher sequence identity to the amino acid sequence represented by SEQ ID NO: 8.

3. The antibody according to claim 1, wherein the antibody
   (1-3) comprises a heavy chain consisting of an amino acid sequence having at least 80% or higher sequence identity to the amino acid sequence represented by SEQ ID NO: 9, and a light chain consisting of an amino acid sequence having at least 80% or higher sequence identity to the amino acid sequence represented by SEQ ID NO: 10.

4. A chimeric antigen receptor (CAR) comprising the antibody according to claim 1, a transmembrane region fused with a carboxyl terminus of the antibody, and an immunocompetent cell activation signal transduction region fused with a carboxyl terminus of the transmembrane region.

5. An immunocompetent cell expressing the CAR according to claim 4.

6. The immunocompetent cell according to claim 5, further expressing interleukin 7 (IL-7) and chemokine ligand 19 (CCL19).

7. A method for treating cancer, comprising administering the immunocompetent cell according to claim 5 to a cancer patient, wherein the cancer is GPC3 expressing hepatocellular carcinoma.

8. A nucleotide encoding the antibody according to claim 1.

9. A vector comprising a promoter and the nucleotide according to claim 8 operably linked to downstream of the promoter.

10. A host cell in which the vector according to claim 9 has been introduced.

11. A nucleotide encoding the CAR according to claim 4.

12. A vector comprising a promoter and the nucleotide according to claim 11 operably linked to downstream of the promoter.

13. A host cell in which the vector according to claim 12 has been introduced.

14. A method for detecting GPC3 (glypican-3), comprising a step of detecting GPC3 using the antibody according to claim 1.

15. A kit for the detection of GPC3 (glypican-3), comprising the antibody according to claim 1, or a labeled form thereof.

* * * * *